United States Patent
Bettenga

(10) Patent No.: US 11,653,937 B2
(45) Date of Patent: May 23, 2023

(54) SYSTEMS AND METHODS FOR ALIGNING SURGICAL DEVICES

(71) Applicant: Mason James Bettenga, Memphis, TN (US)

(72) Inventor: Mason James Bettenga, Memphis, TN (US)

(*) Notice: Subject to any disclaimer, the term of this patent is extended or adjusted under 35 U.S.C. 154(b) by 372 days.

(21) Appl. No.: 17/159,418

(22) Filed: Jan. 27, 2021

(65) Prior Publication Data

US 2021/0228220 A1 Jul. 29, 2021

Related U.S. Application Data

(60) Provisional application No. 62/966,576, filed on Jan. 28, 2020.

(51) Int. Cl.
*A61B 17/17* (2006.01)
*A61B 34/20* (2016.01)
*A61B 90/00* (2016.01)
*A61B 17/00* (2006.01)

(52) U.S. Cl.
CPC ...... *A61B 17/1707* (2013.01); *A61B 17/1717* (2013.01); *A61B 34/20* (2016.02); *A61B 90/37* (2016.02); *A61B 90/39* (2016.02); *A61B 2017/00455* (2013.01); *A61B 2034/2051* (2016.02); *A61B 2034/2055* (2016.02); *A61B 2560/0475* (2013.01)

(58) Field of Classification Search
CPC ........... A61B 5/06; A61B 5/066; A61B 34/30; A61B 34/20; A61B 34/10; A61B 1/2676; A61B 17/17; A61B 17/1707; A61B 17/1717; A61B 90/00; A61B 90/37
See application file for complete search history.

(56) References Cited

U.S. PATENT DOCUMENTS

| | | |
|---|---|---|
| 4,621,628 A | 11/1986 | Brudermann |
| 5,049,151 A | 9/1991 | Durham |
| 5,127,913 A | 7/1992 | Thomas |
| 5,411,503 A | 5/1995 | Hollstien |
| 5,417,688 A | 5/1995 | Elstrom |
| 5,540,691 A | 7/1996 | Elstrom |
| 5,584,838 A | 12/1996 | Rona |

(Continued)

FOREIGN PATENT DOCUMENTS

| | | |
|---|---|---|
| KR | 10-2010-0061444 A | 6/2010 |
| WO | 2009/109371 A2 | 9/2009 |
| WO | 2012/033823 A1 | 3/2012 |

*Primary Examiner* — Christopher J Beccia

(57) ABSTRACT

A system for targeting a feature on a surgical device, includes a shape sensing element coupled to an interrogator and operable to provide information to related to said portion's position in a reference frame in communication with the targeted feature. The interrogator is operable to poll the shape sensing element for information related to said portion's position in the reference frame. A surgical tool is coupled to the targeting system in communication with the shape sensing element. The data processor is operable to communicate with the interrogator to output position information of the portion of the shape sensing element with respect to a calibrated position, defined as the position of the portion of the shape sensing element in the reference frame when the guide axis is aligned to the targeted feature. A display provides the user visual information comparing the position of the tool to the targeted feature.

32 Claims, 38 Drawing Sheets

(56) References Cited

U.S. PATENT DOCUMENTS

| | | |
|---|---|---|
| 5,707,375 A | 1/1998 | Durham |
| 6,074,394 A | 6/2000 | Krause |
| 6,162,228 A | 12/2000 | Durham |
| 6,503,249 B1 | 1/2003 | Krause |
| 6,697,664 B2 | 3/2004 | Kienzle |
| 7,060,075 B2 | 6/2006 | Govari |
| 7,066,943 B2 | 6/2006 | Zirkle |
| 7,488,328 B2 | 2/2009 | Gotfried |
| 7,686,818 B2 | 3/2010 | Simon |
| 7,720,322 B2 | 5/2010 | Prisco |
| 7,727,240 B1 | 6/2010 | Benton |
| 7,753,913 B2 | 7/2010 | Szaklelyhidi, Jr. |
| 7,772,541 B2 | 8/2010 | Froggatt |
| 7,781,724 B2 | 8/2010 | Childers |
| 7,785,330 B2 | 8/2010 | Sherman |
| 7,813,599 B2 | 10/2010 | Moore |
| 8,116,601 B2 | 2/2012 | Prisco |
| 8,265,431 B2 | 9/2012 | Childers |
| 8,273,092 B2 | 9/2012 | Sasing |
| 8,382,759 B2 | 2/2013 | Tuma |
| 8,491,660 B2 | 7/2013 | Kaiser |
| 8,500,746 B2 | 8/2013 | Fernandez |
| 8,623,023 B2 | 1/2014 | Ritchey |
| 8,689,801 B2 | 4/2014 | Ritchey |
| 8,746,076 B2 | 6/2014 | Rogge |
| 8,784,425 B2 | 7/2014 | Ritchey |
| 8,814,868 B2 | 8/2014 | Janna |
| 9,050,131 B2 | 6/2015 | Van Vorhis |
| 9,308,004 B2 | 4/2016 | Giersch |
| 9,526,441 B2 | 12/2016 | Wilhelm |
| 9,554,812 B2 | 1/2017 | Inkpen |
| 9,585,722 B2 | 3/2017 | Ritchey |
| 9,924,956 B2 | 3/2018 | Baumgartner |
| 10,588,644 B2 | 3/2020 | Karg |
| 10,663,290 B1 | 5/2020 | Tongue |
| 2005/0080427 A1 | 4/2005 | Govari |
| 2013/0281884 A1 | 10/2013 | Mullaney |
| 2016/0058321 A1 | 3/2016 | Ritchey |

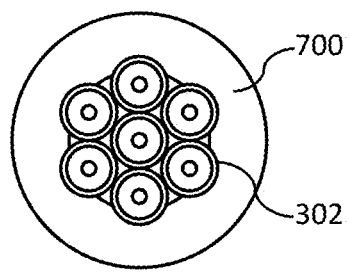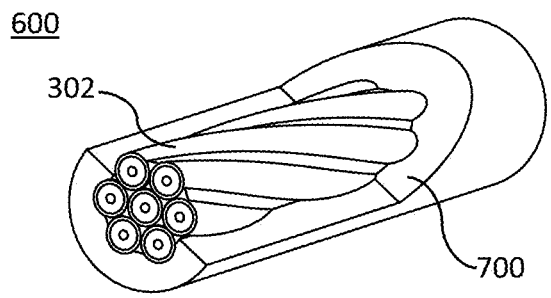
FIG. 6
Section B-B
FIG. 7A
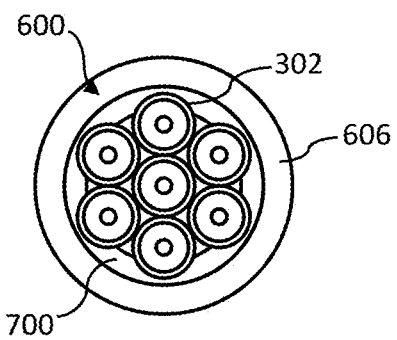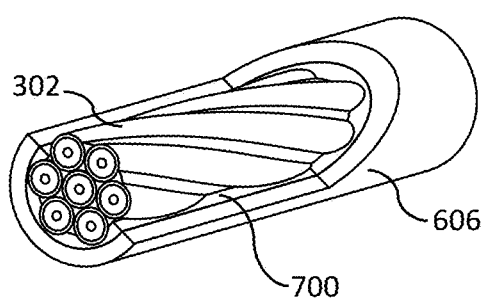
FIG. 6
Section C-C
FIG. 7B Section D-D

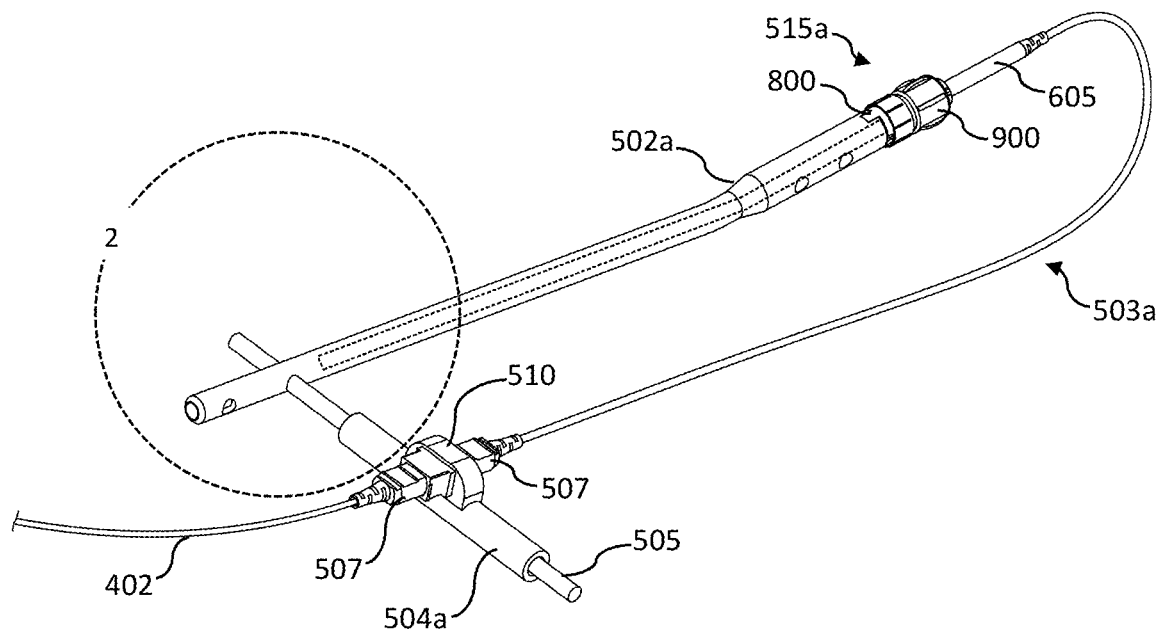
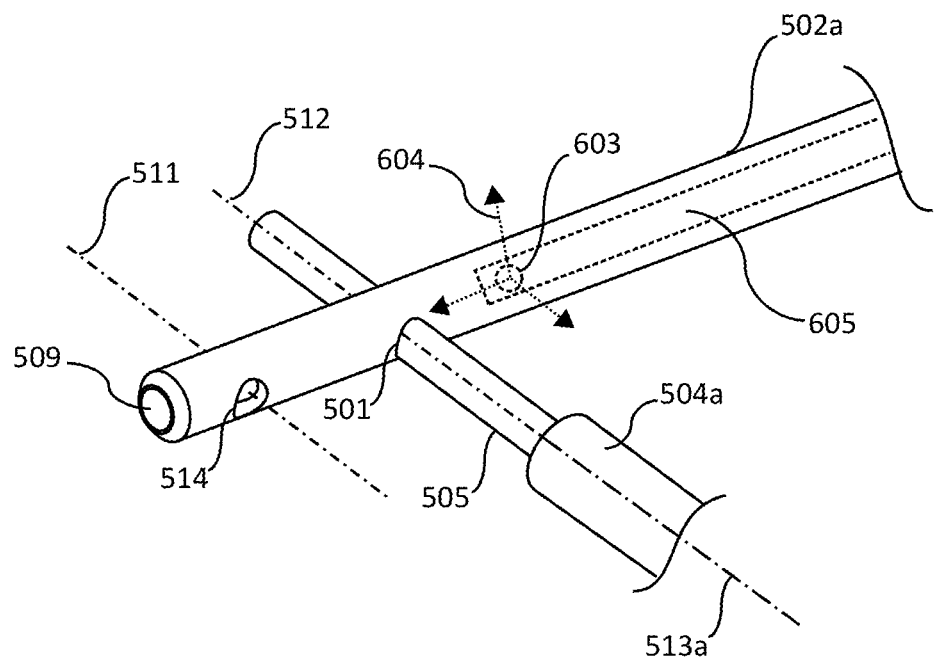
Detail 2
FIG. 11

Detail 3

Detail 4

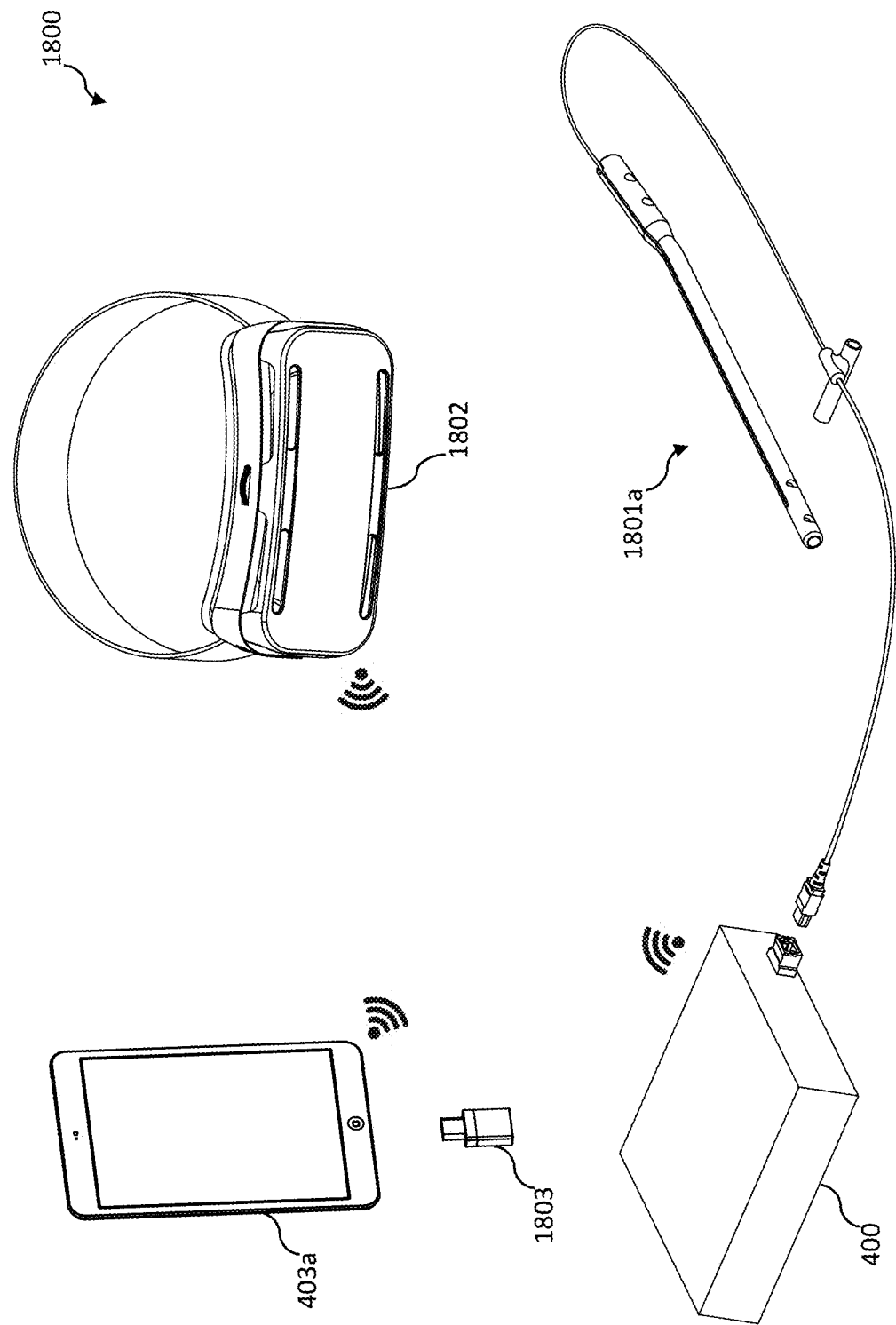

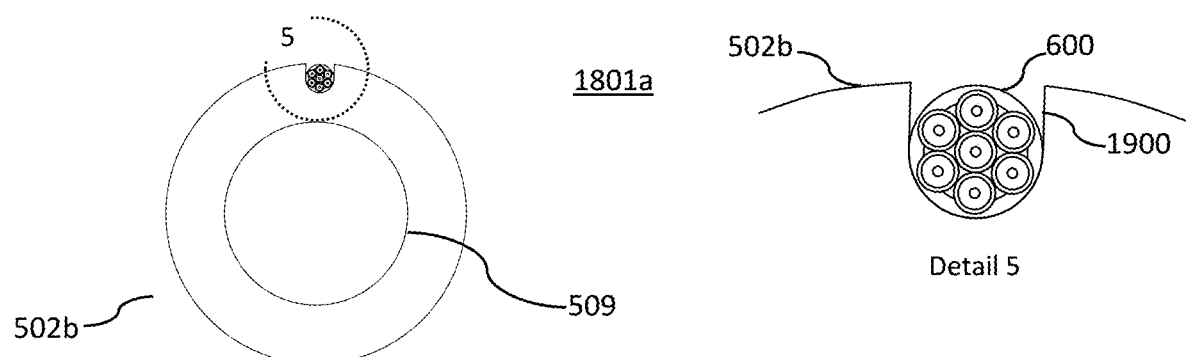
FIG. 19B
Section E-E
FIG. 20A
Detail 5
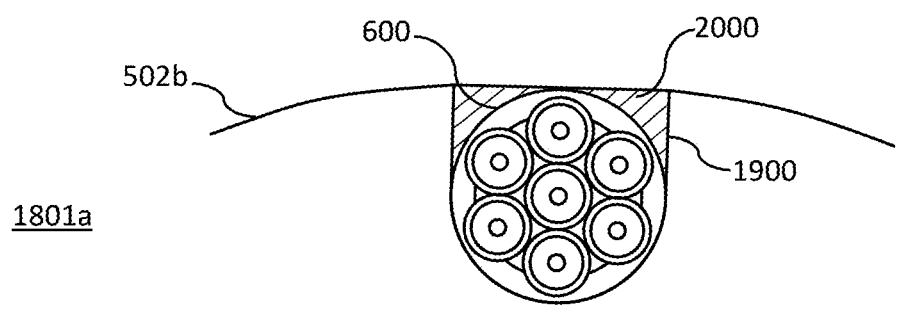
FIG. 20B
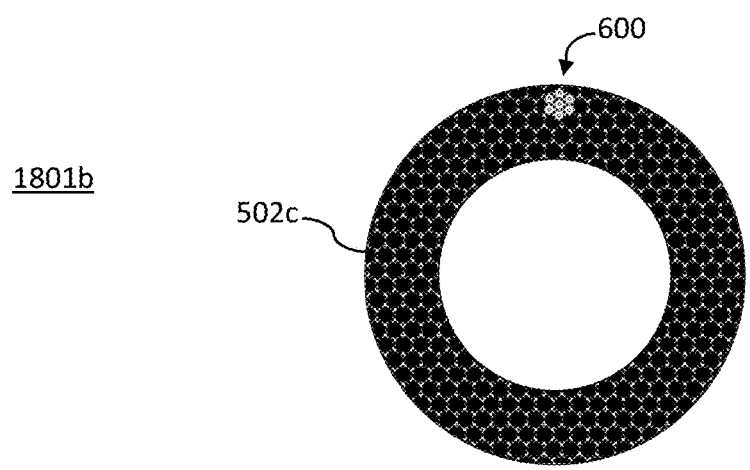
FIG. 20C Detail 6

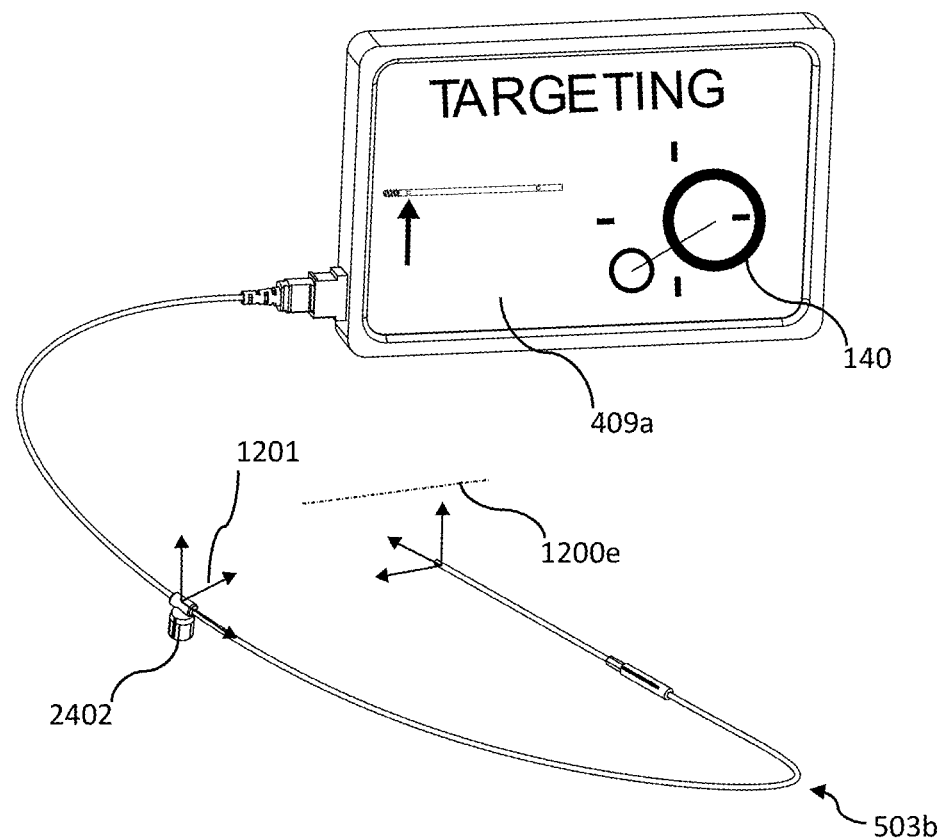
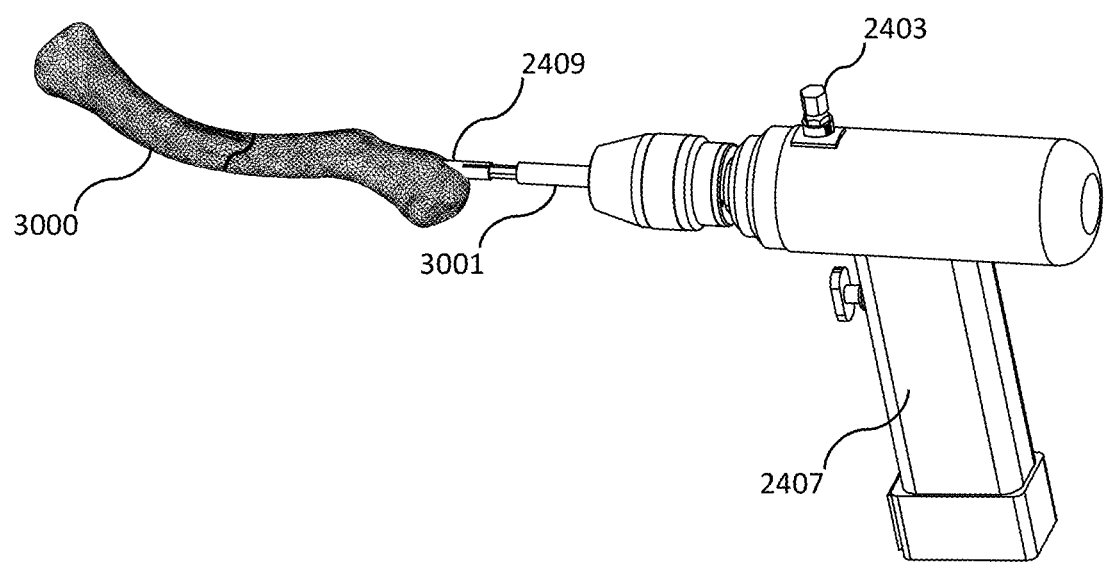
FIG. 30

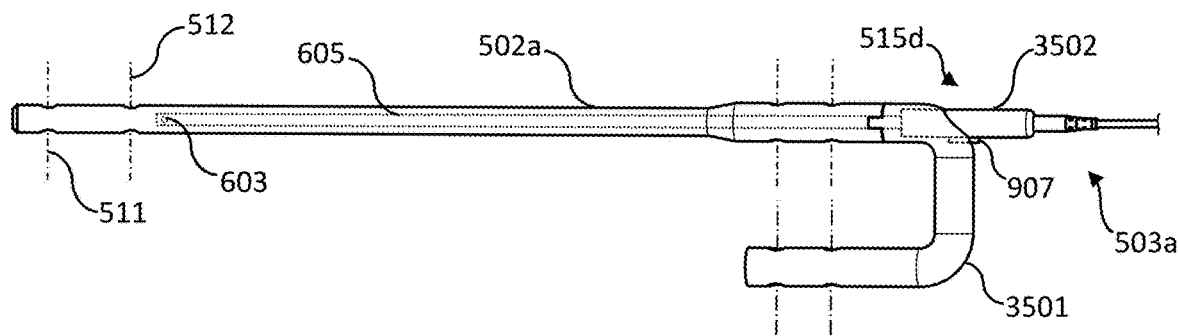
FIG. 36B
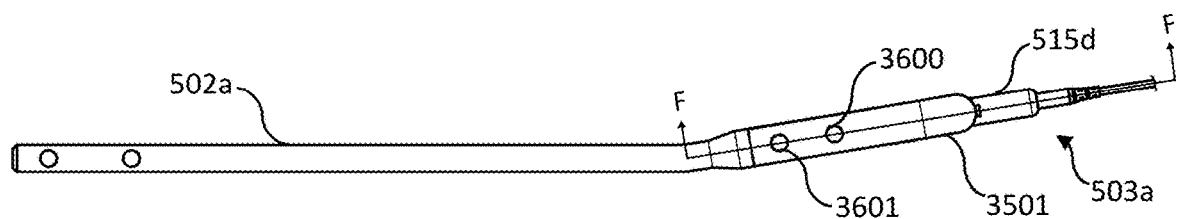
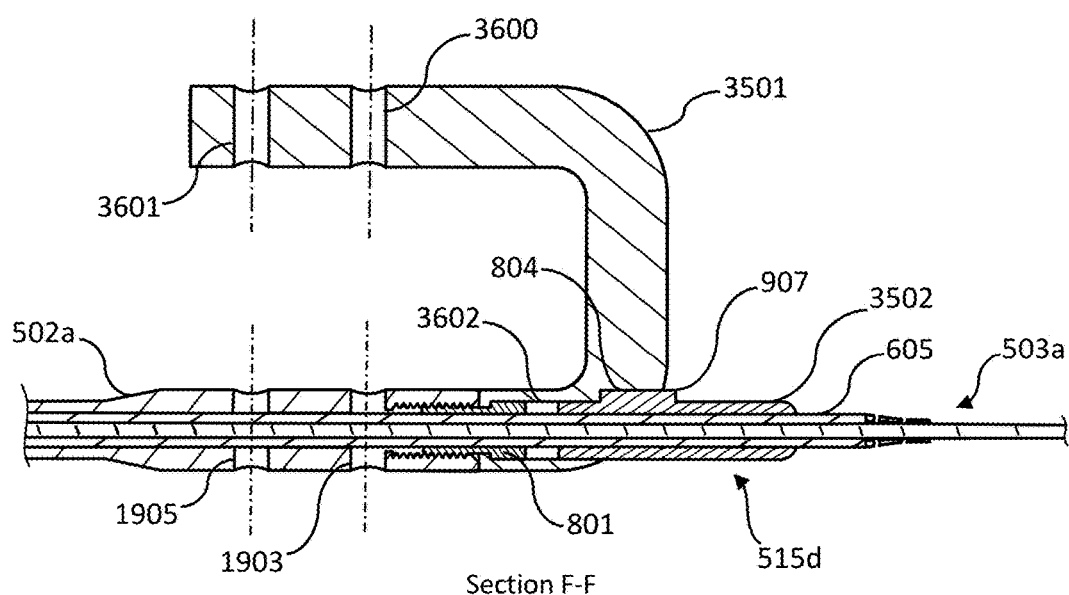
Section F-F
FIG. 36C

SYSTEMS AND METHODS FOR ALIGNING SURGICAL DEVICES

CROSS REFERENCE TO RELATED APPLICATIONS

This application claims priority to U.S. Provisional App. No. 62/966,576 filed Jan. 28, 2020, titled SYSTEMS AND METHODS FOR ALIGNING SURGICAL DEVICES, herein incorporated by reference in its entirety for all purposes.

FIELD OF THE INVENTION

The present invention relates to devices and methods for orthopedic tissue reconstruction procedures requiring the alignment of a surgical tool to a hidden feature on a surgical device.

BACKGROUND

In the field of orthopedic surgery, intramedullary rods, or 'nails', are a common means of providing stable, weight-bearing fixation during the healing period of a fractured bone. The intramedullary space is prepared in a reaming process, and a rod is introduced either from the proximal end of the bone or the distal, depending on the particular anatomy and pathology. Intramedullary nail introduction occurs through an entrance hole formed in a first segment of the fractured bone and is then advanced through the prepared canal, crossing the fracture line, and subsequently advanced through the canal of a second bone segment. Bi-cortical fixation of both the proximal and distal segments of the bone to the ends of the nail is accomplished by drilling through both cortical walls of the bone to form a hole colinear with a hole transverse to the long axis of the implant. A screw is then inserted securing the position of the nail in the bone fragment. The process is repeated for the remaining fixation holes located on both sides of a fracture enabling a weight-bearing reduction of the fracture for healing.

Fixation holes on the nail nearest the point of entry into the first bone segment are generally targeted using an outrigger style insertion handle connected to features in the proximal end of the implanted device. The handle comprises apertures colinear with each of the fixation holes the in the proximal end of the nail, and a drill may be advanced through the guide apertures and targeted hole with good reliability. However, targeting the fixation holes in the nail located in the second bone segment can be challenging due to a deflection of the distal end of the nail relative to the proximal end that may occur when placed in the bone. These deflections may be caused by anatomical inconsistencies commonly found in a population and vary due to conditions of rod length or elastic modulus, bone curvature, or other factors. It is generally accepted that targeting the distal fixation holes with an outrigger style drill guide is not reliable, and various solutions have been proposed.

One method of distal targeting relies on an iterative approach using an intra-operative x-ray machine, commonly known as a C-arm, combined with a radio-opaque reference pin. Several images are taken while the surgeon manually aligns the pin to the distal fixation hole in the intramedullary rod, and when the surgeon is confident that the drill axis has been identified, an attempt to drill through the cortex along the centerline of the targeted hole is made. If multiple unsuccessful attempts are made, the cortical bone intended to provide structural support may be rendered insufficient and necessitate exchanging the rod for an alternate implant having fixation screws in other locations. A second problem encountered using this method is the elevated level of radiation exposure experienced by the surgical staff and the patient. Often, lead vests are worn to minimize the radiation exposure, with the extra weight of the vest contributing to fatigue.

Other methods employ the use of magnetic field sensors interacting with a magnetic field enabled to calculate the position of the flux sensor with respect to the field. One example, described in U.S. Pat. No. 8,623,023 B2, couples a drill guide to a magnetic field generator moveable outside the bone which perturbs an array of small coils placed inside the lumen of the nail located in a known position and orientation (pose) relative to the targeted hole. The position of the drill guide-field generator assembly with respect to the sensor can be calculated by the interpretation of the signals generated by the sensor in response to the unique pose in the magnetic field, which is then related to the pose of the guide to the targeted hole by further calculation. A second example described in U.S. Pat. No. 7,060,075 B2 employs similar phenomena by placing wired or wireless magnetic field sensors disposed temporarily in the lumen of the nail or integrated with the body of the nail. Various examples of position sensing by placing a magnetic source inside the lumen of the nail in a known location to a targeted hole while a moveable drill guide coupled to a magnetic flux sensor have also been well described. U.S. Pat. Nos. 5,127,913 and 7,785,330 B3 illustrate examples of permanent magnets coupled in rigid communication with a target while a moveable sensor-drill guide assembly operates to relate the position of the sensor with respect to the magnetic source to the position of the drill guide with respect to the targeted feature. In another example, U.S. Pat. No. 5,584,838 describes an apparatus which places a magnetic field generating coil inside the nail in conjunction with the targeted feature while a sensor array coupled to a moveable drill guide.

Though electromagnetic position sensing removes the radiation exposure to the patient and surgical staff, the method presents its own limitations. Metallic objects such as instrumentation or the surgical table located within the magnetic field volume can significantly influence the purity of the data collected by the sensor and contribute to inaccurate positional calculation. Field generation equipment can be large and cumbersome when attached directly to the drill guide, and the latency between movement of field and the updated position on the display can be high. In contrast, magnetic field sources placed within or bonded to the implant are limited in size causing the flux volume to be compact, limiting the sensitivity of the system to minor changes in position of the guide which affects the accuracy of the tool-target alignment.

Other systems and methods have been developed to track the position of a non-visible feature by detecting the deflection of the distal end of the nail, while tracking the proximal end using a secondary navigation system. U.S. Pat. No. 8,382,759 describes a fiducial marker coupled to the proximal end of an intramedullary nail and tracked by an optical navigation system in a coordinate system. A deformation detection device comprising a shape-sensing fiber optic cable is placed in the lumen to provide a measurement of the deflection of the target feature from a first, resting position in the reference frame to a second, deflected position with respect to the tracked fiducial. The deflected position can then be determined in the coordinate system and targeted by a surgical tool tracked in the same reference frame by the navigation system. U.S. Pat. App. Publ. No. 2013/0281884 A1 (filed 23 Apr. 2013) presents a similar method where the proximal end of the intramedullary nail is tracked using a surgical navigation system, however, the deformation detection device placed in the lumen employs electrically powered linear strain sensors. The combination of tracking systems presents the problem of compounding errors which impacts accuracy, as well as the increased cost of providing two measurement systems to track and align a guide to a feature.

Therefore, a clear need exists for a system which improves the process for the targeting of non-visible features during surgical procedures.

BRIEF SUMMARY OF THE INVENTION

In one embodiment of the invention a system for targeting a feature on a surgical device is provided, comprising a shape sensing element, having a plurality of nodes dispersed therein, coupled to an interrogator and is operable to provide information to the interrogator related to the position and orientation of each node in a coordinate system. A first node is coupled in communication with a surgical tool having a tool axis, and a second node is coupled in communication with a targeted feature having a target axis, such that the position and orientation of the first node in the coordinate system defines a tool reference frame and the position and orientation of the second node in the coordinate system defines a target reference frame. The interrogator is operable to provide an interrogation signal to and receive a modified signal from the shape sensing element to generate interrogation information related to the position and orientation of the nodes in the coordinate system. Additionally, a data processor may receive and interpret the interrogation information received from said interrogator to determine the position and orientation information of the nodes in the coordinate system, compare the pose of a tool datum definable in the tool reference frame with respect to at least one target datum definable in the target reference frame, and provide the comparison to the user on a display, wherein pose of the tool datum with respect to the target datum is related to the pose of the tool axis with respect to the target axis.

Also in one embodiment, the shape sensing element may comprise an optical fiber having a plurality of waveguides or "cores", or a plurality of single-core optical fibers arranged in a bundle and the interrogation information comprises light signals transmitted to and reflected from a plurality of strain-sensing elements such as Fiber Bragg Gratings (FBGs) or natural irregularities dispersed in the cores of the shape sensing element.

Also in one embodiment, the shape sensing element may be removably coupled to the target feature or the position of the second node with respect to the target feature may be adjustable. Also in one embodiment, the surgical tool may be removably coupled in communication with the first node of the shape sensing element, or the display may be coupled to the surgical tool.

Also in one embodiment, a calibration file containing information related to the position of the target datum in the target reference frame, wherein the calibration file is provided as digital information stored on a portable memory device connectable to the data processor, or as digital information accessible by the data processor via a network data connection, or a combination thereof.

In another aspect of the invention, a medical apparatus is provided, comprising: a surgical device having at least one target feature, wherein the at least one target feature has a first end and a second end and a target axis therebetween, and a shape sensing element having a first end and a second end and a plurality of nodes dispersed therein, the first end connectable to an interrogator, wherein the shape sensing element is operable to receive an interrogation signal from the interrogator and return a modified signal to the interrogator related to the position and orientation of each node in a coordinate system, wherein a first node is coupled in communication with a surgical tool and least a second node is coupled in communication with the at least one target feature, wherein the surgical tool comprises a first end and a second end and a tool axis therebetween, the position and orientation of the first node in the coordinate system defines a tool reference frame and the position and orientation of the at least second node in the coordinate system defines a target reference frame, a tool datum is definable in the tool reference frame and at least one target datum is definable in the target reference frame, and the pose of the tool datum with respect to the at least one target datum is related to the pose of the tool axis with respect to the target axis of the at least one target feature. Also in one embodiment, the origin of the coordinate system defines the first node.

Also disclosed herein is a method of aligning a tool to a target feature on a surgical device, comprising the steps: a) coupling a first node of a shape sensing element in communication with a surgical tool, the surgical tool having a first tool end and a second tool end and a tool axis therebetween, the shape sensing element having a first element end and a second element end and a plurality of nodes therebetween, the first element end coupled to an interrogator, the interrogator operable to poll the shape sensing element for information related to the position and orientation of each node in a coordinate system and transmit the information to a data processor, the data processor operable to interpret the information and compare the pose of the first node with respect to at least a second node in a coordinate system, wherein the position and orientation of the first node in the coordinate system defines a tool reference frame, wherein a tool datum is definable in the tool reference frame, b) coupling a second node of the shape sensing element in communication with at least one target feature on a surgical device, the at least one target feature having a first feature end and a second feature end and a target axis therebetween, wherein the position and orientation of the second node in the coordinate system defines a target reference frame, wherein a target datum is definable in the target reference frame, and c) providing information to the user comparing the pose of the tool axis with respect to the target axis, wherein the pose of the tool datum with respect to the target datum is related to the pose of the tool axis with respect to the target axis.

Also in one embodiment, the invention further comprises a calibration file comprising information relating to the pose of the target datum in the target reference frame, wherein the calibration file is provided as digital information stored on a portable memory device, or as digital information accessible via a network data connection, or a combination thereof.

BRIEF DESCRIPTION OF THE DRAWINGS

The foregoing and other objects, features, and advantages will be apparent from the following more elaborate description of the embodiments, as illustrated in the accompanying drawings in which like reference characters refer to the same parts throughout the different views. The drawings are not necessarily to scale, emphasis instead being placed upon illustrating the principles of the embodiments. For a detailed description of example embodiments, reference will now be made to the accompanying drawings in which:

FIG. 7A illustrates front and section views of a portion of the shape sensing element of FIG. 5, according to an embodiment of the present invention;

FIG. 7B illustrates front and section views of a portion of the shape sensing element of FIG. 5, according to an embodiment of the present invention;

FIG. 11 illustrates an exemplary step of coupling the targeting sensor of FIG. 5 to an intramedullary nail, according to an embodiment of the present invention;

FIG. 18 is a perspective view of a targeting system for aligning a tool to a feature on a surgical device comprising a shape sensing element, according to a second embodiment of the present invention;

FIG. 20A illustrates a section view of the targeting sensor of FIG. 19A integrated onto an intramedullary nail, in accordance with the disclosure;

FIG. 20B illustrates a section view of an alternate means of bonding the shape sensing element of FIG. 19A to an intramedullary nail, according to an embodiment of the present invention;

FIG. 20C illustrates a section view of an alternate means of bonding the shape sensing element of FIG. 19A to a composite intramedullary nail, according to an embodiment of the present invention;

FIG. 30 illustrates the nail implantation step of a surgical procedure employing the targeting system of FIG. 24, according to an embodiment of the present invention;

FIGS. 36A-36C are assembly top, side, front and section views, respectively, of the assembly of FIG. 35, in accordance with the disclosure;

DETAILED DESCRIPTION

Figure 1:
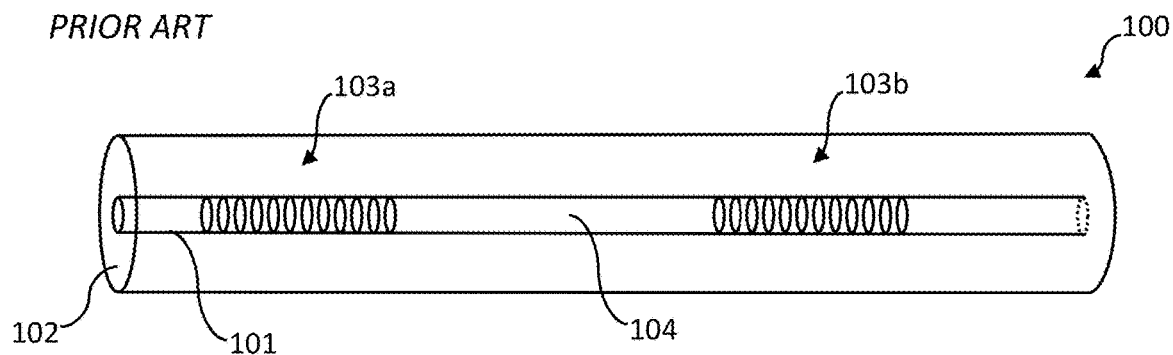
FIG. 1 is a perspective view of an example of a known optical fiber having multiple Fiber Bragg Grating sensors disposed in a single core, in accordance with the disclosure.

While the invention is amenable to various modifications, permutations, and alternative forms, specific embodiments have been shown by way of example in the drawings and are described in detail below. The intention, however, is not to limit the invention to the embodiments described. The invention is intended to cover all modifications, equivalents, and alternatives falling within the scope of the invention as defined by the appended claims.

The inventor provides a system for aligning a surgical tool to a feature on an orthopedic device by employing a shape-sensing cable in a novel manner. One commercially available technology capable of providing a dynamic reconstruction of the shape of a cable in a coordinate system comprises a single optical fiber or a collection of optical fibers coupled to an interrogator and data processing unit. Sets of optical strain sensors disposed within multiple cores of a single fiber, or the cores of a bundle of single-core fibers, which transmit and selectively reflect light provided by the interrogator, are interpreted to generate 3-dimensional position and orientation data of nodes along its length in a coordinate system. A brief discussion of the general concepts of fiber optic shape sensing (FOSS) is now provided to help illustrate various implementations of the present invention.

FIG. 1 illustrates the basic construction of an single-core optical fiber 100. A light conducting core 101 is shown formed in the interior of a cladding 102. As a light signal propagates along core 101, particular wavelengths are scattered by random imperfections or reflected at a defined sensor point by formed features, known as Fiber Bragg Gratings (FBGs), while other wavelengths pass unaffected. Changes in pressure, strain, or temperature can change the refractive index of the sensor point thereby altering the wavelength reflected back to the source, generally known as the Bragg wavelength. Core 101 is shown having a first strain sensor 103a separated from a second strain sensor 103b by a tether 104 which has no signal changing properties. A protective coating 105 (not shown for clarity) is generally bonded to the outer surface of cladding 102.

Figure 2:
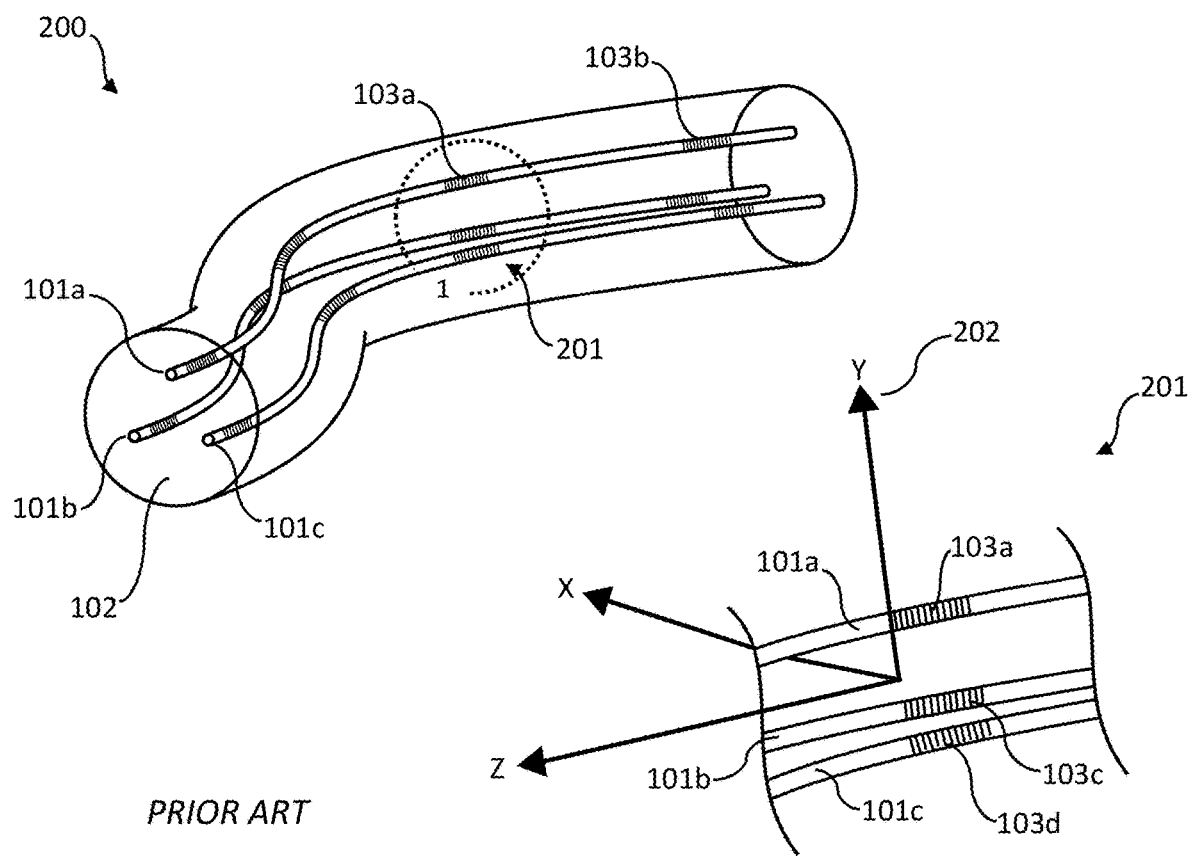
FIG. 2 is a perspective view of one example of a known multicore shape-sensing optical fiber, in accordance with the disclosure.

An example of a multicore optical fiber 200 having a first core 101a, a second core 101b, and a third core 101c formed in a common cladding 102 and dispersed evenly from the central axis of the fiber as shown in FIG. 2. As a portion of the fiber experiences a bending force, a measurable strain field develops such that some areas of a cross section may be tension while others are in compression, depending on the direction of the bend. A set of strain sensors 103a, 103c, 103d form a node 201 having a reference frame 202 which has a calculable position and orientation with respect to a neighboring node when the strain data from each sensor is interpreted. As the number of nodes increases in a length of shape-sensing cable, the tether portion reduces in length and the positional resolution improves. Fully distributed FBGs provide a scheme for continuous measurement along the cable and are well described.

Figure 3A:
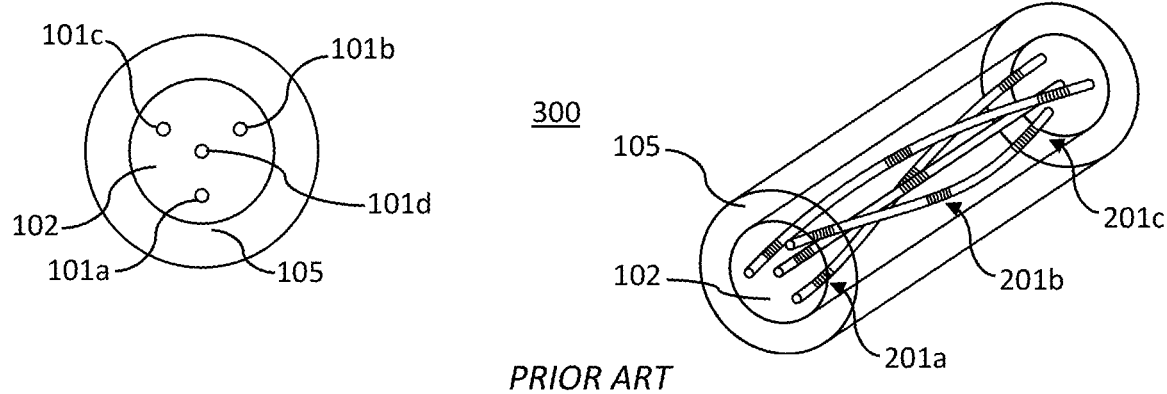
FIGS. 3A-3C each are front and perspective views, respectively, of examples of known configurations of the components of a shape-sensing element, in accordance with the disclosure.
Figure 3B:
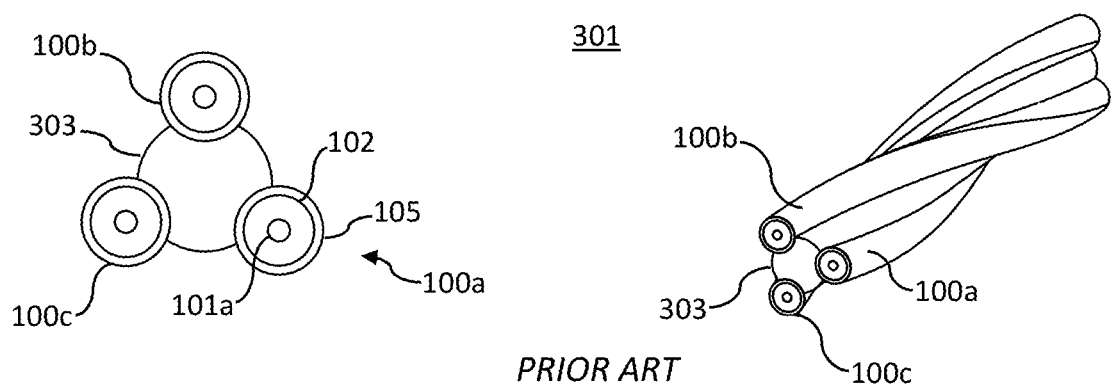
Figure 3C:
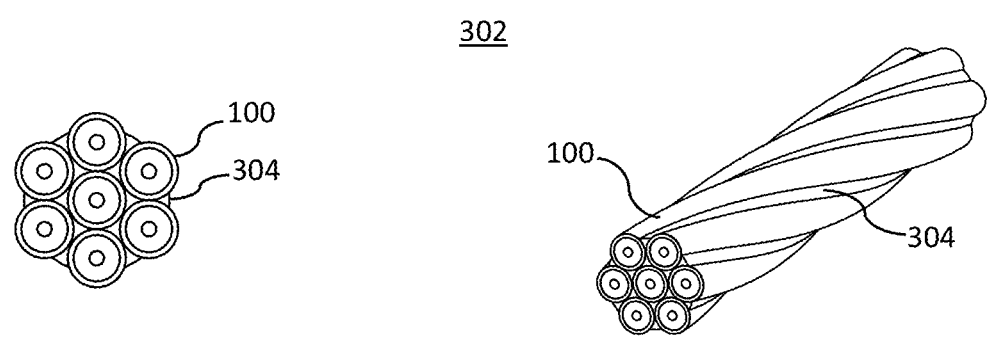

Various configurations of the cores of the shape sensing element have been described to improve positional resolution, accuracy, and the sensitivity to twist around the central axis of the cable with relevant examples shown in FIGS. 3A-3C. FIG. 3A shows a multi-core optical fiber 300 having several cores dispersed in a common cladding. Cores 101a-101c are dispersed in a helical pattern around a fourth core 101d which is placed colinear with the central axis of the fiber with coating 105 bonded to the outer surface of cladding 102. Sets of FBG strain sensors arranged within the cores form nodes 201a-201c at intervals along the length of the cable. FIG. 3B shows a shape sensing element 301 comprising three single-core optical fibers 100a-100c bonded to the outer surface of a central element 303 and arranged in a helical pattern about the central axis of the cable. In another configuration, several single-core optical fibers 100 are twisted together in a helical pattern an bonded together using an adhesive 304 to form a multi-fiber bundle 302 shown in FIG. 3C. One advantage of the multifiber bundle approach is the ability to arrange the FBG sensors in various configurations where an improvement in accuracy and sensitivity for a given number of sensors may be realized.

Figure 4:
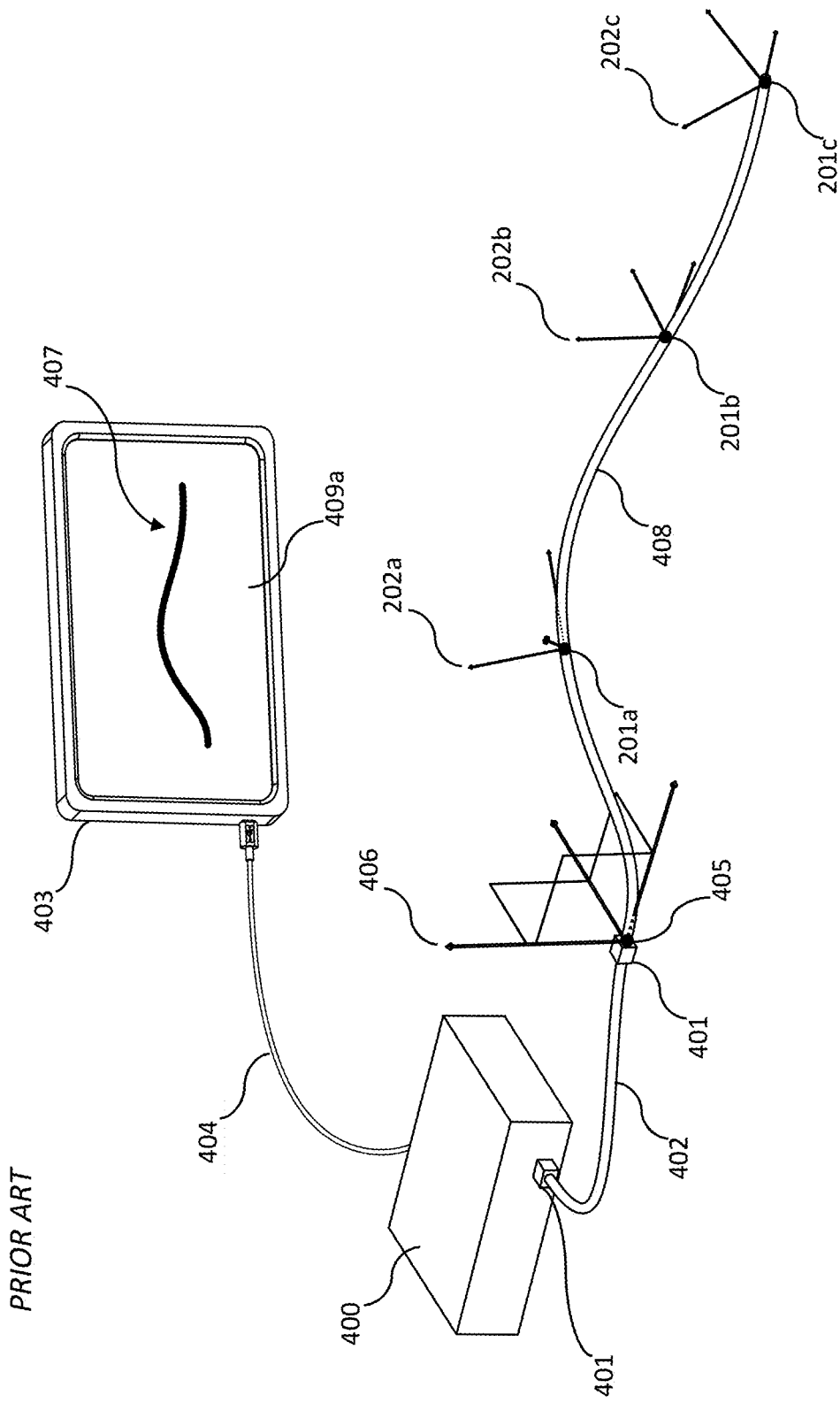
FIG. 4 illustrates an example of a known fiber optic shape sensing system, in accordance with the disclosure.

FIG. 4 shows the major components of a commercially available fiber optic shape-sensing system which can be deployed to quantify the dynamic changes in shape of an object coupled to the shape-sensing element or track the position of objects connected to various nodes in real time within a coordinate frame. An interrogator 400 is connected to a patch cable 402 through a multicore coupler 401 at the first end, while a second multicore coupler 401 at the second end of patch cable 402 connects to a shape sensing element 408. Patch cable 402 comprises an equivalent number of cores as shape sensing element 408, though it does not contain any strain sensors and operates to transmit light signals over a length of cable where shape-sensing is not required. Thus, interrogator 400 may be placed at a distance, such as outside a sterile field in an operating theater, from the first shape-sensing node and allowing the limited number of nodes to be concentrated in the length of cable where shape-sensing is desired to maximize accuracy and sensitivity.

Interrogator 400 is a data acquisition component that provides an outbound interrogation signal in the form of a light signal to each core, in either a multicore fiber or multifiber bundle, and receives an inbound interrogation signal reflected light back from the FBGs or other reflective elements embedded in the core for interpretation. Various techniques of interrogation are available to generate the data necessary to calculate a shape reconstruction 407, with non-limiting examples being Wavelength Division Multiplexing (WDM), Optical Frequency Domain Reflectometry (OFDR), and Optical Time Domain Reflectometry (OTDR). The first end of shape sensing element 408, connected to patch cable 402, has a base reference frame 406 associated with a base node 405. Base reference frame 406 may be a Cartesian coordinate system in which the position and orientation of all other nodes of the shape sensing element may be defined. For illustration purposes, a first calculated node 201a has a position ($X_1$, $Y_1$, $Z_1$) and an orientation defined by a first calculated reference frame 202a. A second node 201b and third node 201c downstream from node 201a have a unique coordinate positions ($X_2$, $Y_2$, $Z_2$ and $X_3$, $Y_3$, $Z_3$, respectively) in base reference frame 406 with a reference frame 202b and a reference frame 202c, respectively, defining their orientations. A data connection cable 404 may provide a power source and a data connection to transfer the information collected by interrogator 400 to the data processing equipment in a control unit 403 where shape reconstruction 407 is calculated and rendered as an image provided to the user on a display 409a.

The present invention is now described in enabling detail in the following examples, which may represent more than one embodiment. Although one or more of these embodiments may be preferred, the examples disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Figure 5:
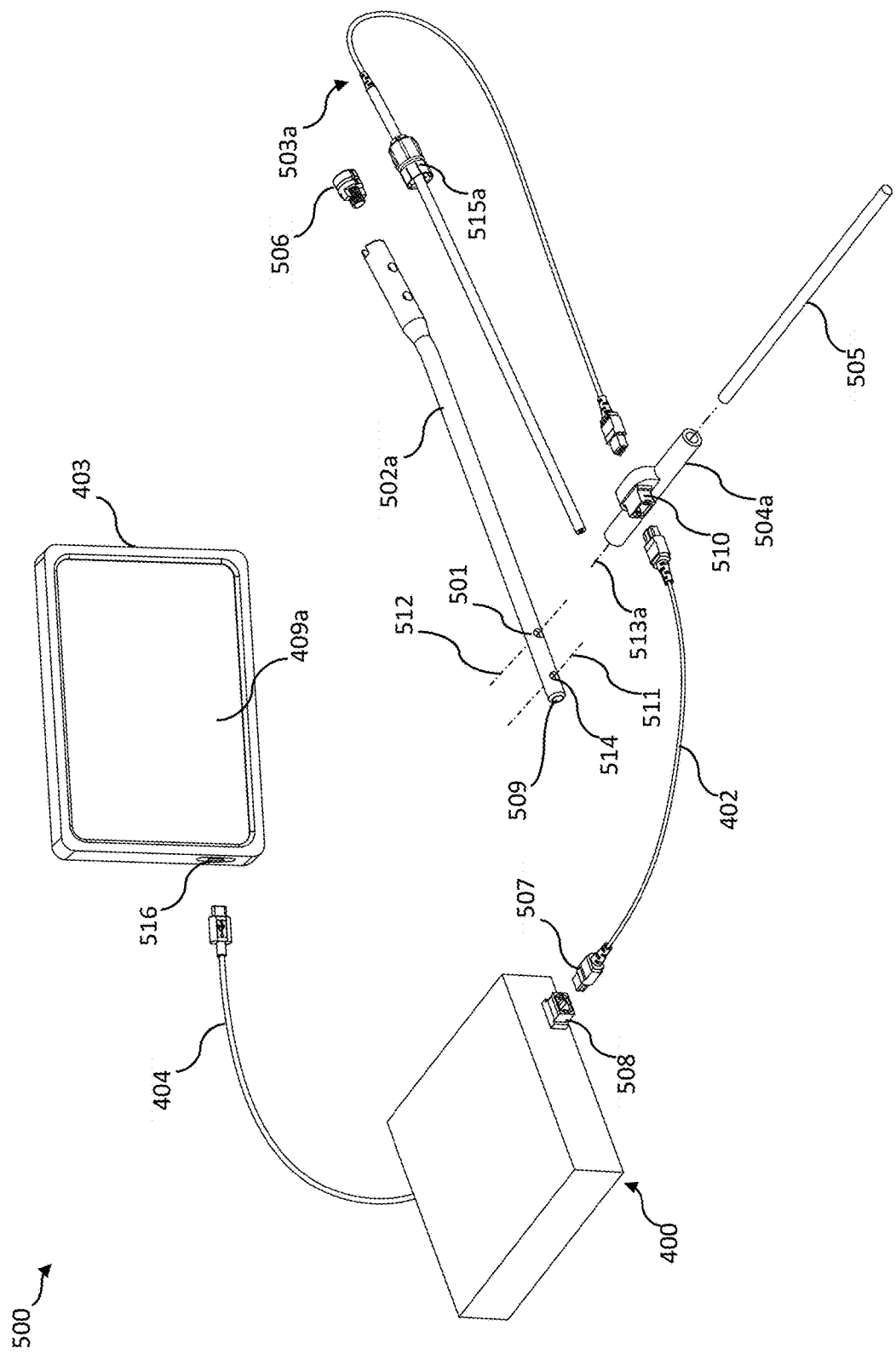
FIG. 5 is a perspective view of a targeting system for aligning a tool to a feature on a surgical device comprising a shape sensing element, according to an embodiment of the present invention.

Referring now to FIG. 5, one embodiment of a targeting system 500 is shown in perspective view, and is designed to provide the user a means of aligning a surgical tool to a distal fixation hole 501 having a target axis 512, and a distal fixation hole 514 having a target axis 511, in an intramedullary nail 502a having a central lumen 509. In this example, targeting system 500 comprises a targeting sensor 503a, control unit 403 connectable to interrogator 400 by data connection cable 404, and a drill guide 504a connectable to both patch cable 402 and targeting sensor 503a. In this embodiment, display 409a is a touchscreen monitor integrated with control unit 403 operating as a graphical user interface (GUI) to the system's software, and for visual presentation of information to the user during the surgical procedure, having a screen of sufficient size enabling the user to view the data when placed outside of the sterile field. A port 516 provided with control unit 403 may supply power to interrogator 400 as well as a data link for the transfer of interrogated information or commands between the two components via data connection cable 404. Several types of powered, data connection devices are currently available which may include, but are not limited to universal serial bus (USB), serial-ATA (SATA), or peripheral component interface (PCI). Non-powered, signal-only connection may also be used in certain configurations where interrogator 400 and control unit 403 are provided with separate power sources. Patch cable 402 is operationally connected to interrogator 400 using commercially available MPO/MTO multicore fiber optic connectors. A male multicore connector 507 is affixed at both ends of patch cable 402 connectable to a female multicore connector 508 supplied on interrogator 400 at the first end, and a multicore fiber coupler 510 affixed to drill guide 504a, having a tool axis 513a, at the second end such that light signals provided by the interrogator are transmissible through patch cable 402 are made available to targeting sensor 503a for interrogation. Targeting system 500 further comprises a implant adapter 506 and a positioning coupler 515a, enabling the user to removably couple a node of targeting sensor 503a at a fixed location with respect to distal fixation holes 501 and 514 in lumen 509, and a calibration pin 505 to mechanically align the tool axis with either target axis during a feature registration process. Once the registration is complete, the user may decouple targeting sensor 503a from intramedullary nail 502a for implantation, and then recouple with the node returned to the calibrated position in lumen 509 for hole targeting and drilling.

Figure 6A:
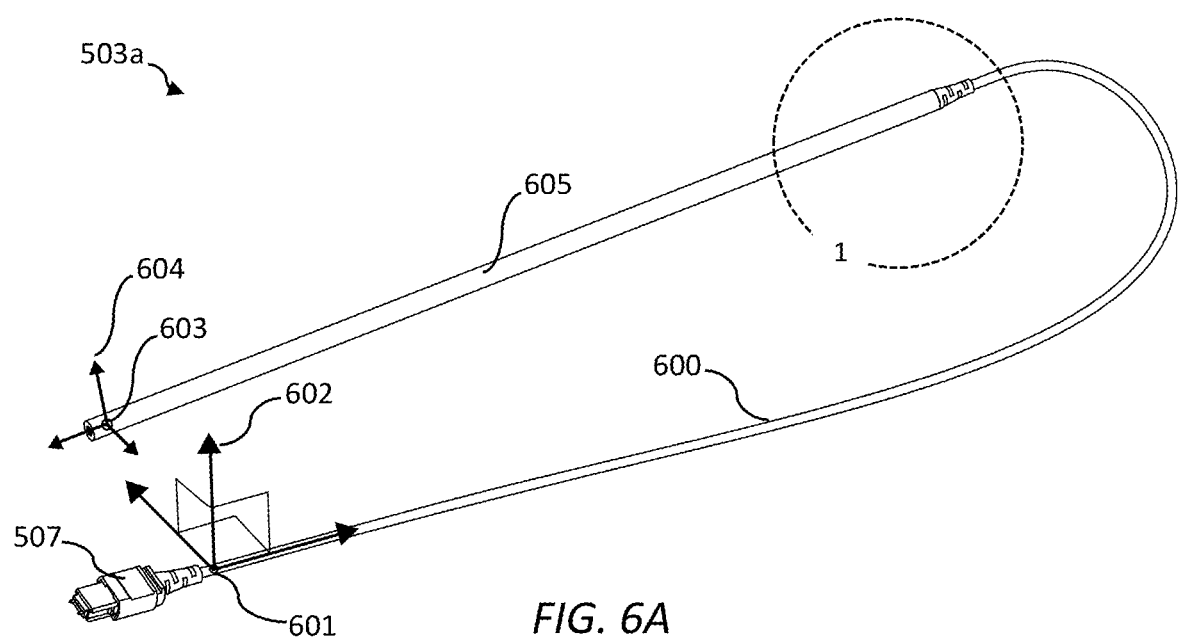
FIGS. 6A-6B are perspective and front views, respectively, of the shape sensing element of FIG. 5, according to an embodiment of the present invention.
Figure 6B:
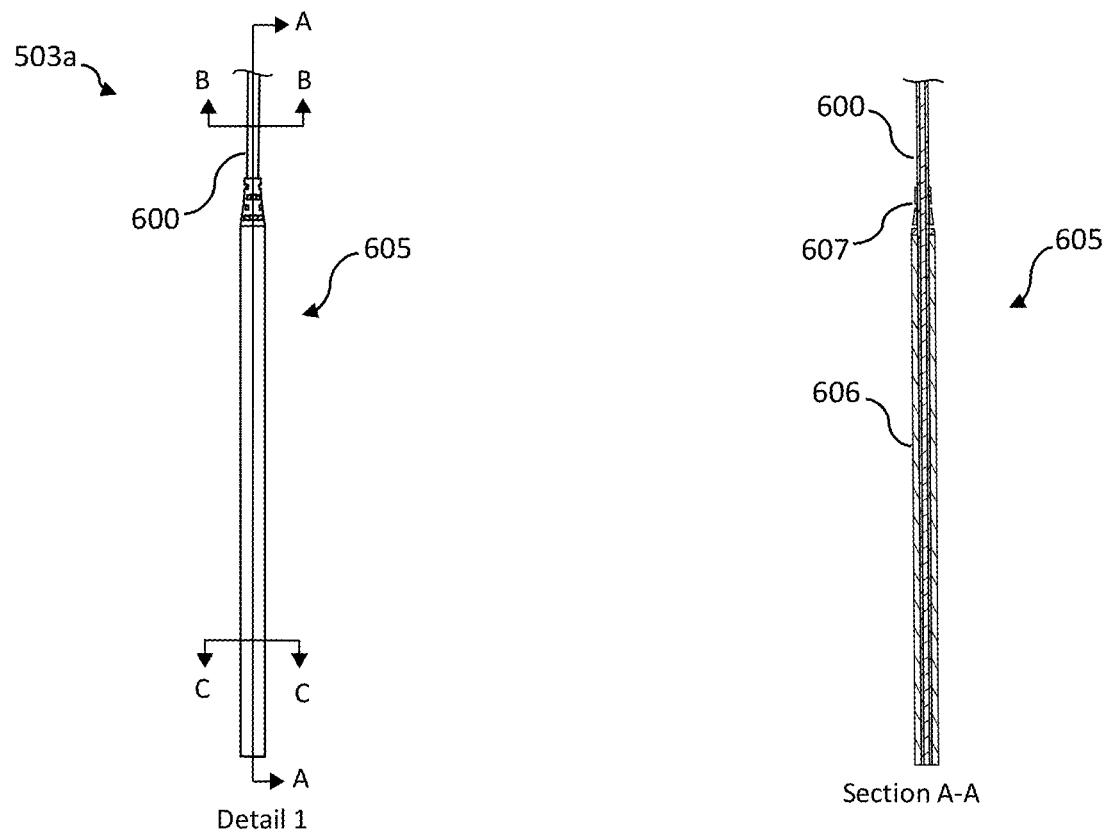

FIGS. 6A-6B illustrate perspective, detail, and section views of targeting sensor 503a in accordance with the disclosure. Targeting sensor 503a is designed to link the position and orientation, or "pose" of a surgical tool rigidly coupled to a base node 601 at the first end of a shape sensing cable 600, having a base reference frame 602, to the pose of one or more targeted features rigidly and removably coupled to a target node 603 near the second end of shape sensing cable 600, having a target reference frame 604. In this embodiment, shape sensing cable 600 employs a length of multi-fiber bundle 302 (illustrated in FIGS. 7A-7B) approximately double the length of the selected nail and connectable to patch cable 402 via a male multicore connector 507 affixed at the first end, with a portion extending through the center of a probe 605 where target node 603 is located. Shape sensing cable 600 is provided operable to receive light signals from interrogator 400 and reflect light information from the plurality of FBG sensor point in each core of multi-fiber bundle 302 to enable the localization of target reference frame 604, and datums defined therein, in base reference frame 602. Probe 605 is designed as a portion of shape sensing cable 600 introduced into lumen 509 to place target node 603 in a fixed location substantially close to but without obscuring distal fixation hole 501 of intramedullary nail 502a. A sleeve 606 encapsulates shape sensing cable 600 from target node 603 towards base node 601 having a length extending from the proximal end of intramedullary nail 502a to enable the engagement of mechanisms for removably securing probe 605 to features formed in the proximal end of intramedullary nail 502a. Sleeve 606 is an elastically deformable tube designed to add rigidity and protect shape sensing cable 600 and may be constructed using a variety of biocompatible materials with examples including but not limited to alloys of stainless steel, alloys titanium, nitinol or zirconium. Shape sensing cable 600 may be secured in the interior of sleeve 606 using an adhesive, a crimp, or an interference fit. Sleeve 606 may also be formed by over-moulding shape sensing cable 600 with biocompatible thermoplastics such as polyether-ether-ketone (PEEK), thermoset plastics such as polyurethane, or composites of high strength fiber and a thermoset or thermoplastic matrix. A stress relief 607 is affixed to targeting sensor 503a at the proximal end of probe 605 to provide mechanical support and promote a smooth radius of curvature of the extending portion of shape sensing cable 600.

FIGS. 7A-7B are section views of shape sensing cable 600 and probe 605, respectively, where their components may be further appreciated. As shown in FIG. 7A, shape sensing cable 600 may be constructed with multi-fiber bundle 302 as the shape sensing core of the cable, and a flexible coating 700 bonded to add strength and stiffness to the cable for protection and handling properties. Examples of suitable biocompatible materials in coating 700 may include, but are not limited to medical grades of polyvinylchloride, polyethylene, PEEK, polycarbonate, polyetherimide, polysulfone, polypropylene, or polyurethane. FIG. 7B shows a cross-section of a portion of shape sensing cable 600 that is encapsulated in sleeve 606 to form the structure of probe 605.

Figure 8A:
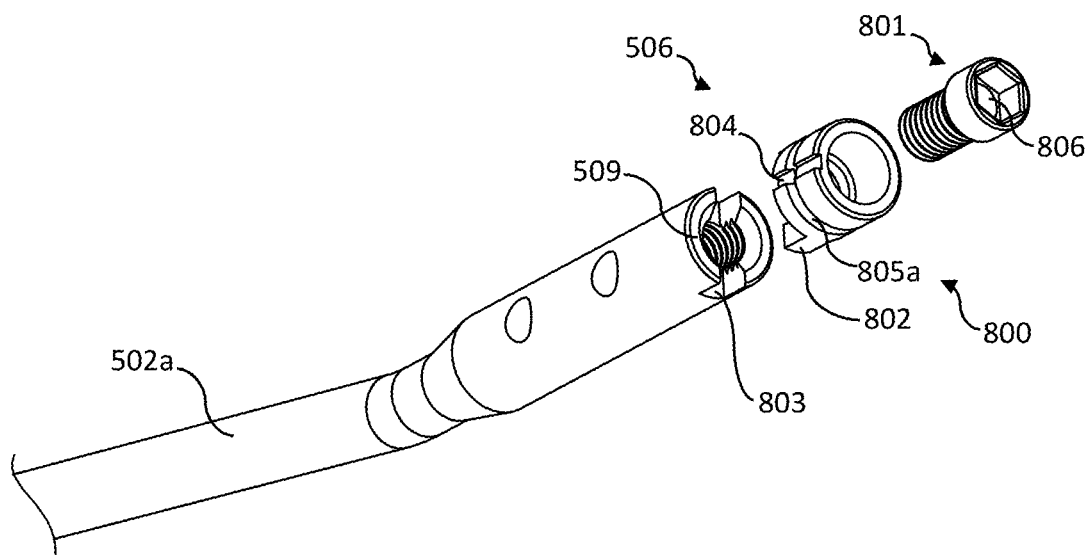
FIGS. 8A-8B are exploded and assembly views, respectively, of the implant adapter and intramedullary nail of FIG. 1, according to an embodiment of the present invention.
Figure 8B:
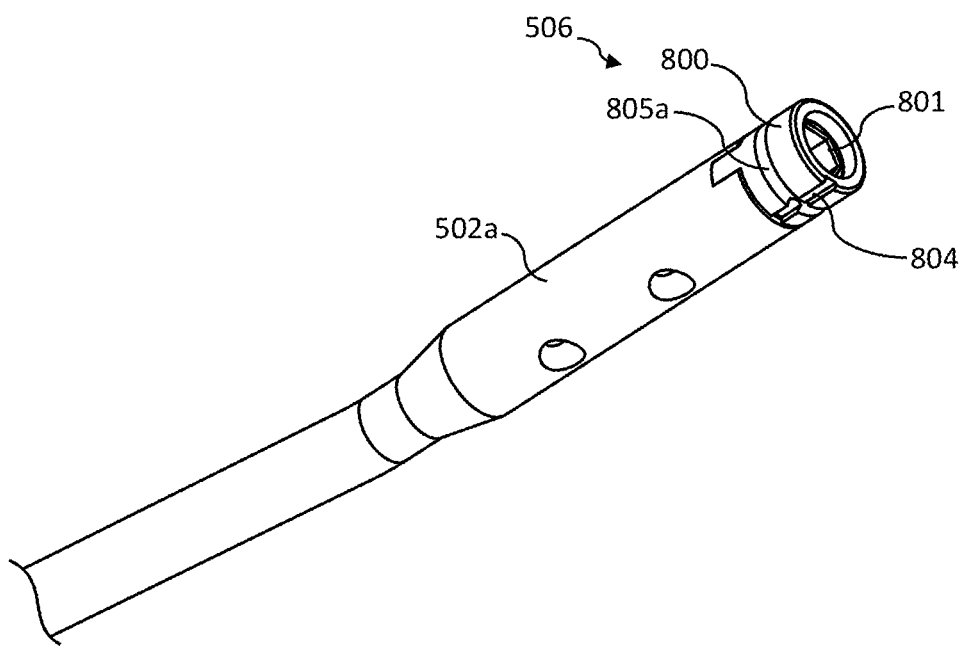

FIGS. 8A-8B illustrate the assembly of implant adapter 506 onto the proximal end of intramedullary nail 502a, according to an embodiment of the present invention. In this example, implant adapter 506 is designed to enable positioning coupler 515a (not shown) to be removably and rigidly coupled to the proximal end of intramedullary nail 502a, and comprises a coupling barrel 800 and a cannulated bolt 801. Coupling barrel 800 is a tubular body having a key 802 extending from one end designed to engage with a slot 803 on intramedullary nail 502a, and is affixed to intramedullary nail 502a using bolt 801. A lengthwise slot 804 and a circumferential groove 805a are formed in coupling barrel 800 serving as locating features to enable positioning coupler 515a to be rigidly coupled thereto. Bolt 801 is connectable to thread features formed in intramedullary nail 502a having a aperture 806 allowing objects to access lumen 509. As shown in FIG. 8B, implant adapter 506 is assembled onto the proximal end of intramedullary nail 502a. In this configuration, slot 804 and groove 805a are in rigid communication with no degrees of freedom of motion with respect to the proximal end of intramedullary nail 502a.

Figure 9A:
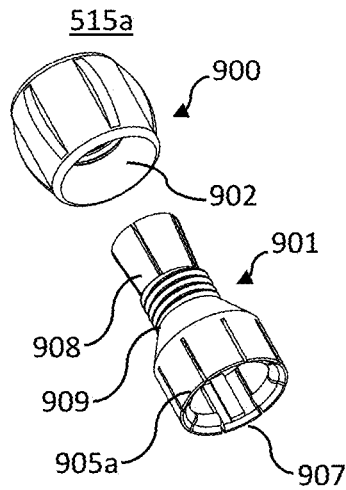
FIGS. 9A-9C are exploded, front, and section views, respectively, of the adjustable positioning coupler of FIG. 5, in accordance with the disclosure.
Figure 9B:
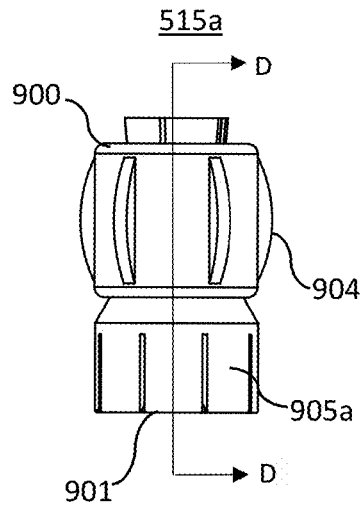
Figure 9C:
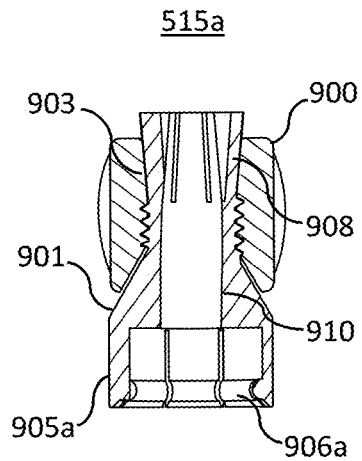

FIGS. 9A-9C illustrate exploded, front, and section views, respectively, of positioning coupler 515a, in accordance with the disclosure. Positioning coupler 515a is designed to removably couple with implant adapter 506 (illustrated in FIGS. 8A-8B) and adjustably couple with probe 605 (illustrated in FIG. 6B) and comprises a compression ring 900 and a coupler 901. Coupler 901 is a tubular body having a proximal end comprising a collet 908 and a distal end comprising a clip 905a. Collet 908 has an aperture 910 formed along its central long axis with an inner diameter sufficient to allow probe 605 to slide axially through the body when configured in an open position, and secure probe 605 from sliding axially or rotationally with respect to the proximal end of intramedullary nail 502a when in a closed position as determined by the user by rotating compression ring 900 on a thread form 909. Compression ring 900 is a tubular body having a ramp 903 operable to actuate collet 908 from an open position to a closed position. A thread form 902 in the inner diameter which engages with thread form 909 in a screw-type fashion to operate collet 908. A gripping feature 904 may also be provided to reduce slippage during operation. Clip 905a is designed to removably engage with coupling barrel 800 (illustrated in FIGS. 8A-8B) and comprises a series of elastic tangs extending from the distal end and arranged around the circumference to enable removable connection. Formed in the inner diameter of clip 905a is an axial key 906a, designed to engage with groove 805a of coupling barrel 800, and a rotational key 907, designed to engage with slot 804 of coupling barrel 800. When assembled onto coupling barrel 800, positioning coupler 515a is fixed in all degrees of freedom with respect to implant adapter 506.

Figure 10:
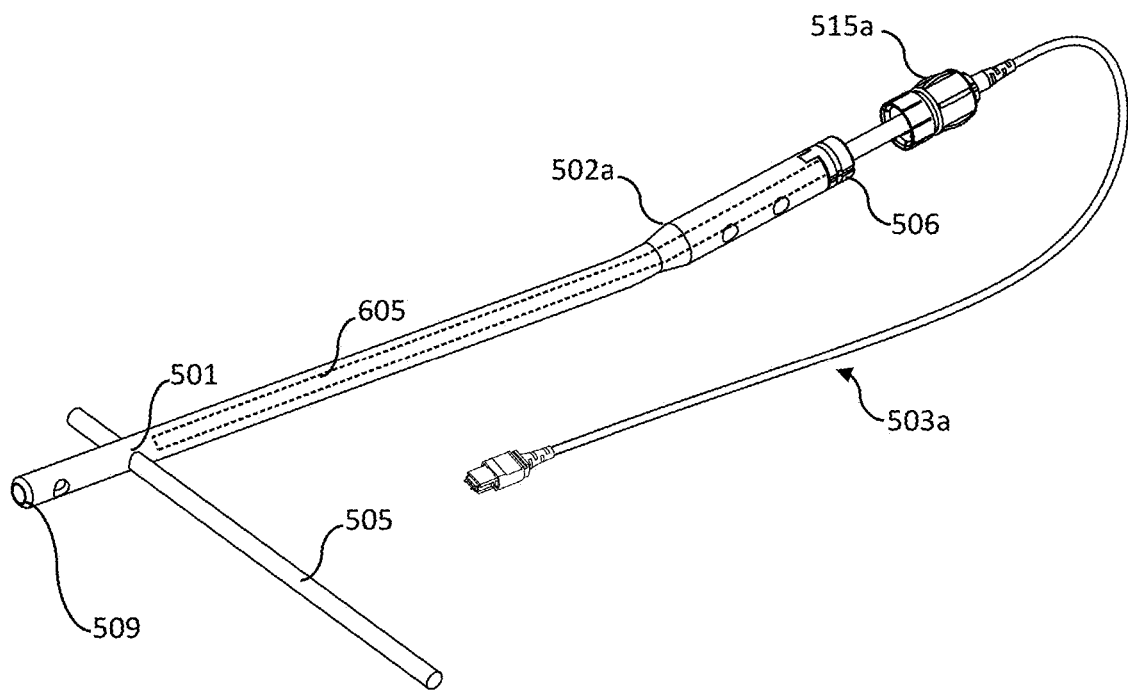
FIG. 10 illustrates an exemplary step of coupling the targeting sensor of FIG. 5 to an intramedullary nail, according to an embodiment of the present invention.

FIGS. 10-11 illustrate exemplary steps of coupling targeting sensor 503a to intramedullary nail 502a, according to an embodiment of the present invention. With implant adapter 506 assembled onto to the proximal end of intramedullary nail 502a and positioning coupler 515a adjustable at the proximal end of probe 605 as shown in FIG. 10, the distal portion of probe 605 is inserted into lumen 509 and adjusted such that its end of arrives immediately proximal to and not obscuring distal fixation hole 501. Optionally, calibration pin 505 may be inserted into distal fixation hole 501 to ensure that no portion of targeting sensor 503a is exposed to distal fixation hole 501 thereby preventing damage from drilling. As shown in FIG. 11, drill guide 504a is placed over calibration pin 505 aligning tool axis 513a colinear with target axis 512. Patch cable 402 and targeting sensor 503a are coupled by connecting their respective male multicore connectors 507 to multicore fiber coupler 510 on drill guide 504a enabling the interrogation of the cores of targeting sensor 503a. With the position of probe 605 with respect to distal fixation hole 501 remaining as described in FIG. 10, positioning coupler 515a is then adjusted to connect with coupling barrel 800. Compression ring 900 is then rotated to rigidly couple positioning coupler 515a to probe 605. In this configuration, target node 603 is located in rigid communication with distal fixation hole 501 and distal fixation hole 514. Thus, target reference frame 604 is located in lumen 509 of intramedullary nail 502a in a fixed position and orientation with respect to target axis 511 and target axis 512.

Figure 12A:
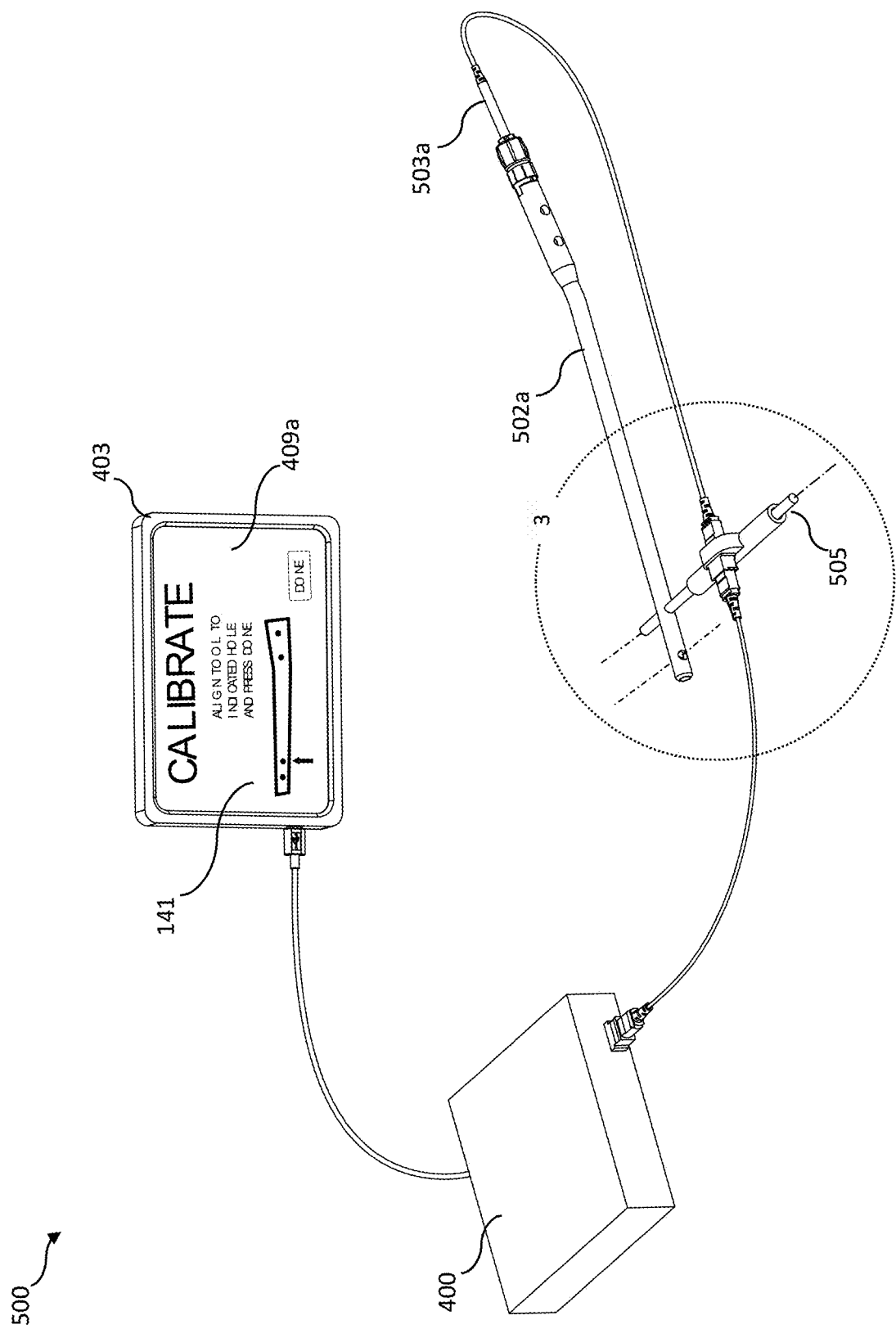
FIG. 12A is a perspective view of the targeting system of FIG. 5 coupled to an intramedullary nail and configured for calibrating the targeting sensor to a targeted feature, according to an embodiment of the present invention.
Figures 12A, 12B:
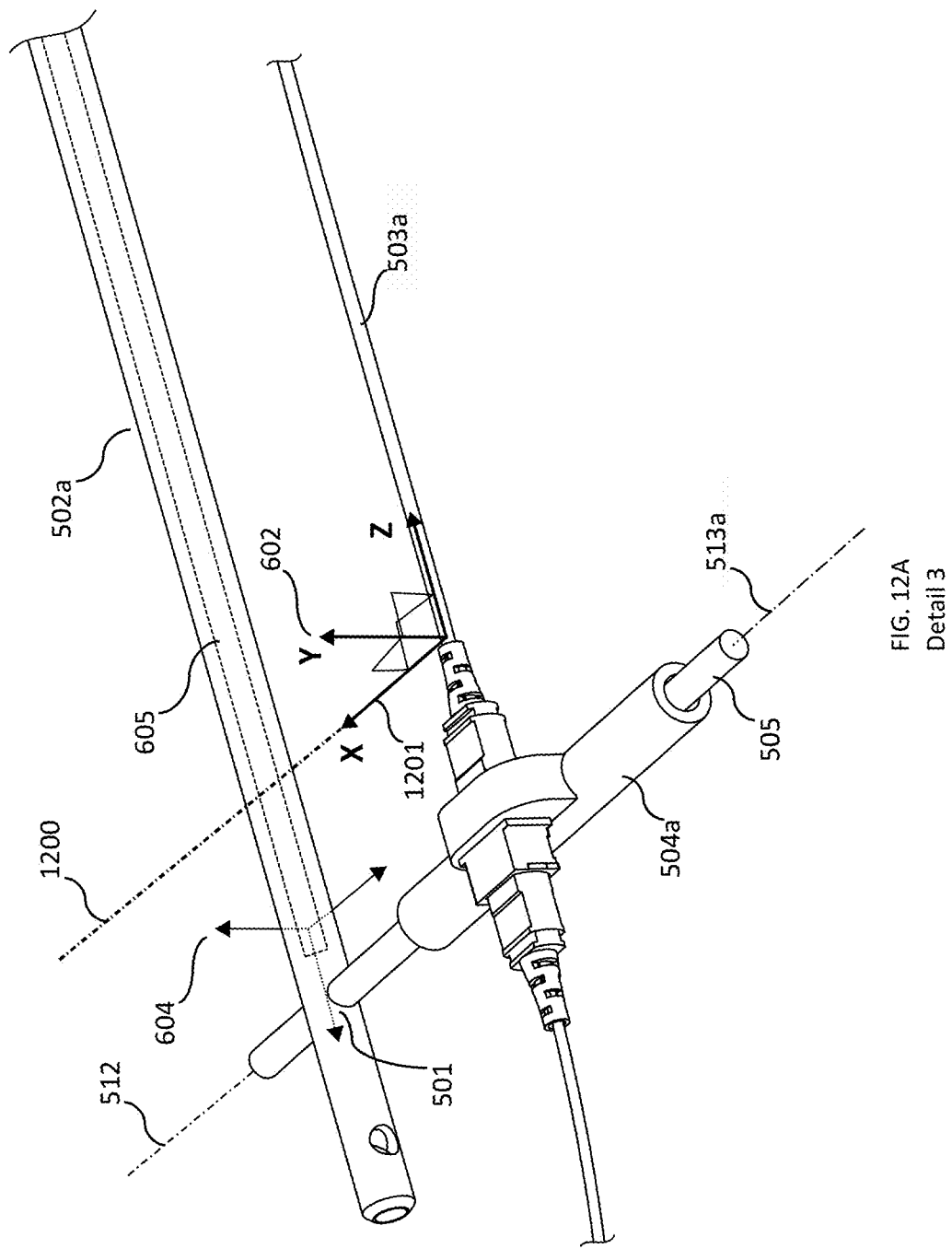
FIG. 12B is a detail view of a portion of the assembly of FIG. 12A, in accordance with the disclosure.

FIGS. 12A-12B are perspective and detail views, respectively, illustrating targeting system 500 configured for calibrating the position of distal fixation hole 501a drill guide to a feature on an intramedullary nail, according to an embodiment of the present invention. As shown in FIG. 12A, targeting sensor 503a coupled to intramedullary nail 502a as described heretofore. Targeting sensor 503a is operable to receive an interrogation signal provided by interrogator 400 and return a modified signal to interrogator 400 to generate positional data of each node, which may be referred to as interrogation information. A calibration program 141 is loaded into the operating system of control unit 403 with instructions provided to the user on display 409a. The user may select the targeted hole corresponding to the placement of calibration pin 505 in intramedullary nail 502a. In the example shown in detail in FIG. 12B, drill guide 504a is aligned with distal fixation hole 501, with tool axis 513a aligned with target axis 512 using calibration pin 505. A target datum 1200 is then defined as an axis in target reference frame 604 which corresponds to a tool datum 1201 which is an axis defined in base reference frame 602. In this illustration, target datum 1200 is defined in target reference frame 604 as an axis colinear with the X-axis of base reference frame 602 when tool axis 513a is colinear with target axis 512. It should be noted, however, that any axis definable in base reference frame 602 may be used as the reference to define target datum 1200. Once target datum 1200 is defined and its location in target reference frame 604 is assigned as targeting information associated with distal fixation hole 501, the user may select and calibrate other fixation holes distal to the end of targeting sensor 503a using the aforementioned steps, or complete the calibration and load a targeting program in the operating system of control unit 403.

Figure 13A:
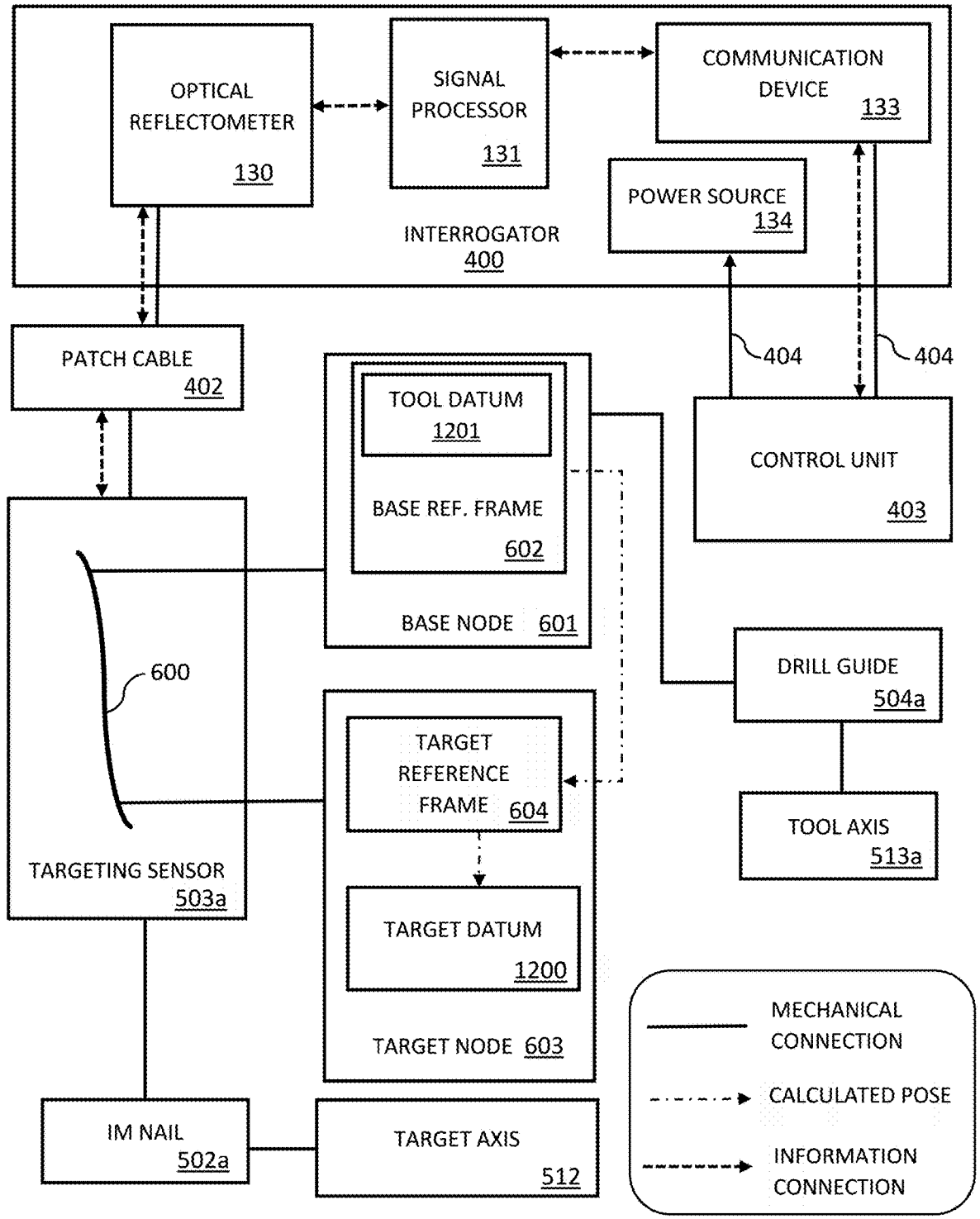
FIG. 13A is a schematic diagram of the targeting system of FIG. 5, according to an embodiment of the present invention.
Figure 13B:
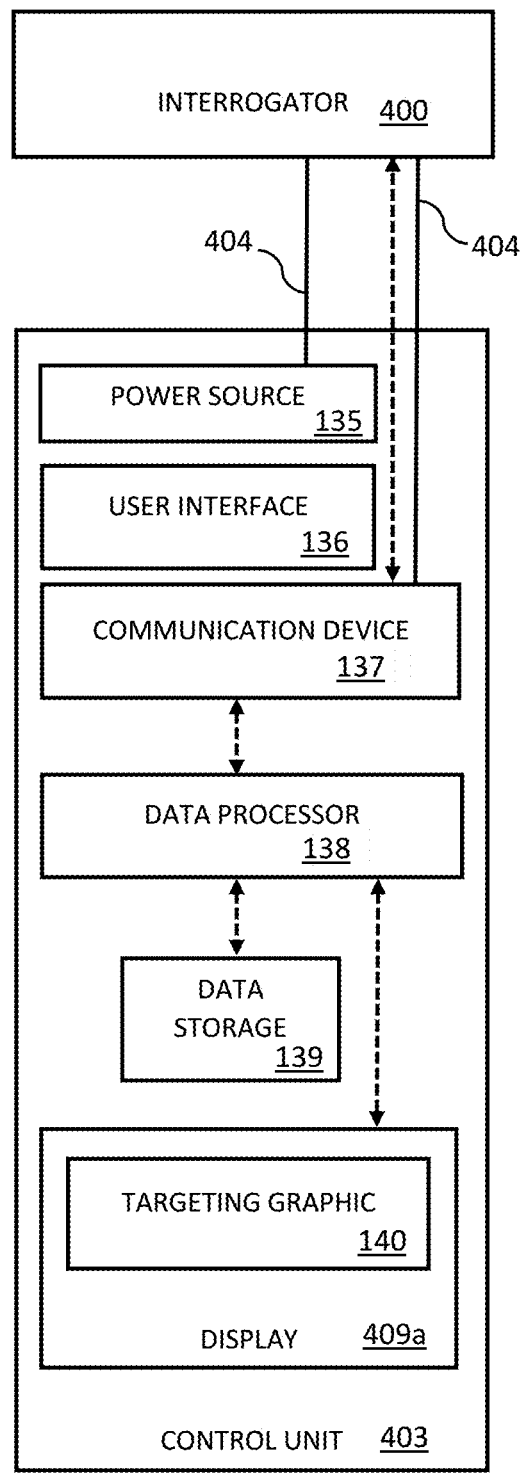
FIG. 13B is a schematic diagram of the control unit of FIG. 13A, according to an embodiment of the present invention.

Referring now to FIGS. 13A-13B where diagrams of the major components and connections of targeting system 500, as described heretofore, are illustrated in schematic form, in accordance with the disclosure. In this example, interrogator 400 is provided comprising an optical reflectometer 130 operable to send and receive light signals transmitted though patch cable 402 to the multiple cores of shape sensing cable 600. Using Optical Time Domain Reflectometry (OTDR), Optical Frequency Domain Reflectometry (OFDR), Wavelength Division Multiplexing (WDM), or other suitable interrogation technique capable of providing information relating to the localized strain of a core of an optical fiber, the light signals are processed for the calculation of positional data of each node by a signal processor 131 and transmitted by a communication device 133 to control unit 403 where the computation steps needed for shape reconstruction and node pose of targeting sensor 503a in base reference frame 602 are performed by a data processor 138. Data connection cable 404 provides electrical power to a power source 134 and a data connection link between interrogator 400 and control unit 403. Control unit 403 further comprises a power source 135 and a communication device 137 operable to provide power to and transfer data to and receive data from interrogator 400 via data connection cable 404. A user interface 136 is provided to enable the user to communicate with control unit 403 which may include but are not limited to a wired or wireless keyboard, mouse or other pointing device, a touchscreen display, voice recognizing interface or other interface enabling the user to send commands to control unit 403. A device for data storage 139 accessible by data processor 138 may be provided as random access memory (RAM), read-only memory (ROM), flash memory, erasable program read-only memory (EPROM), or a combination thereof. The positional comparison of a target axis to a tool axis in the base reference frame can be calculated by data processor 138 and rendered for a visual presentation to the user as a targeting graphic 140 on display 409*a*. It should be noted that the computation, communication, and interrogation devices and techniques described heretofore are well-known to a skilled artisan with further details of subcomponents or operation omitted for brevity.

Figure 14:
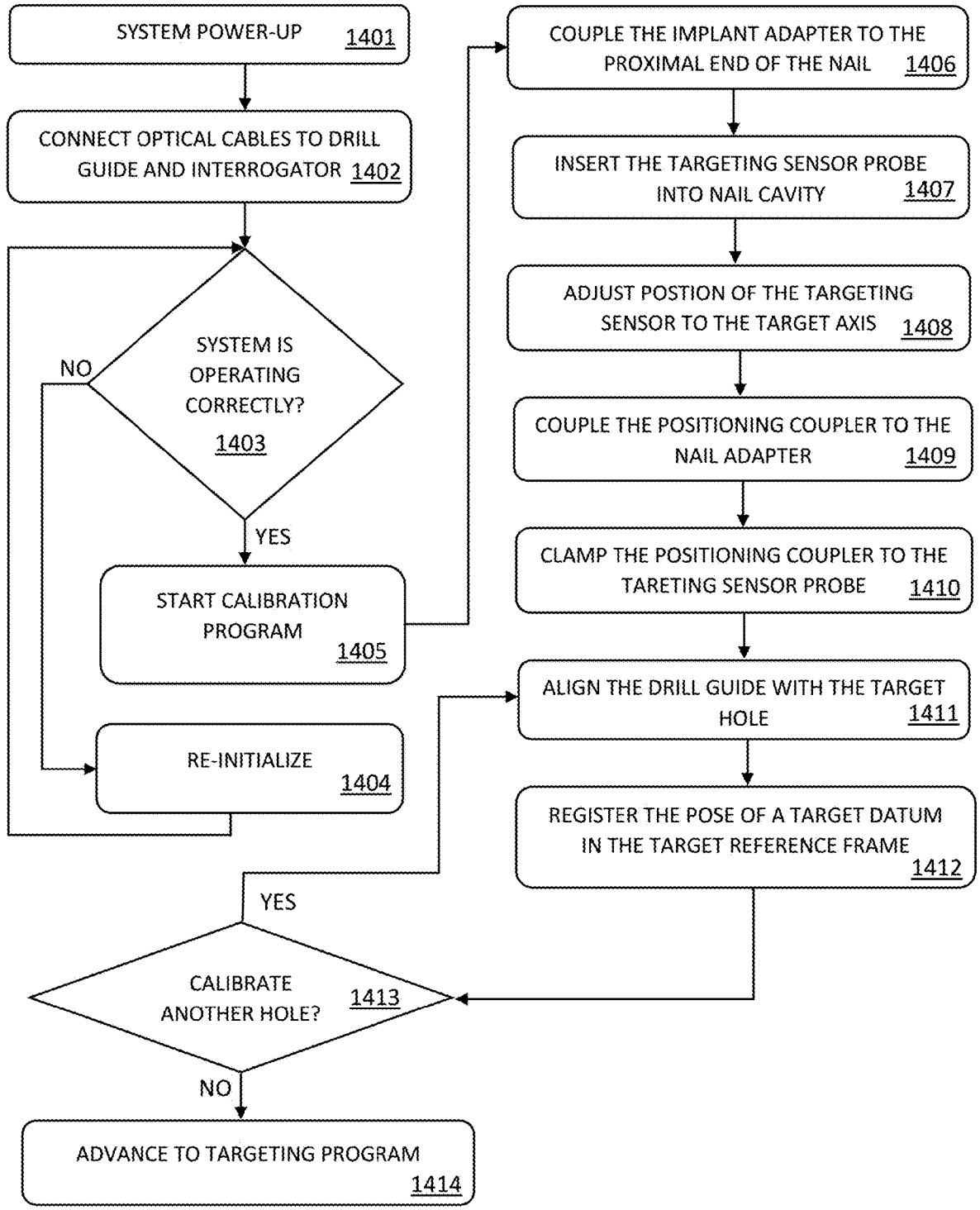
FIG. 14 is a workflow diagram of a calibration process, according to an embodiment of the present invention.

A workflow diagram is presented in schematic form in FIG. 14 to illustrate one method for calibrating drill guide 504*a* to a distal fixation hole in an intramedullary nail, according to an embodiment of the present invention. The method begins with step 1401 where the electrical power and communication connections are made, and the system power is turned on. In step 1402, the user connects a first end of patch cable 402 to interrogator 400. The remaining end of patch cable 402 and the connecting end of targeting sensor 503*a* are connected to drill guide 504*a* as shown in FIG. 12A. In step 1403, a system check is performed to ensure all power and optical connections are correct and the system is performing the necessary activities for shape-reconstruction of the targeting sensor. If the system is not performing normally, a re-initialization step 1404 is needed where the user would troubleshoot the problem and perform a subsequent system check step 1403. If the system is operating normally, the user may then proceeed to step 1405 where a calibration program is loaded into system memory. In step 1406, implant adapter 506 is affixed to the proximal end of intramedullary nail 502*a* as described in FIGS. 8A-8B. In step 1407, probe 605 is inserted into lumen 509 of intramedullary nail 502*a* as shown in FIG. 10. In step 1408, the end of probe 605 is adjusted in proximity to distal fixation hole 501 as shown in FIG. 10. In step 1409, positioning coupler 515*a* is coupled to coupling barrel 800 without changing the location of probe 605 in lumen 509 as shown in FIG. 11. In step 1410, the user secures positioning coupler 515*a* to probe 605 by rotating compression ring 900 causing target node 603 to be located in a fixed pose with respect to distal fixation hole 501 as shown in FIG. 11. In step 1411, the user will mechanically align the drill guide to the fixation hole selected in the calibration software and indicated on display 409*a*. In this example, calibration pin 505 is placed in distal fixation hole 501 and drill guide 504*a* is placed over calibration pin 505 which aligns drill guide 504*a* to distal fixation hole 501 as shown in FIG. 11. In step 1412, target datum 1200 is defined in target reference frame 604 as shown in FIG. 12 and stored in the system memory assigned to distal fixation hole 501. In step 1413, the user may either choose to calibrate the system to target another feature, such as distal fixation hole 514. If this option is chosen, the user will select a different fixation hole in the software and reposition calibration pin 505 and drill guide 504*a* appropriately, and continue to register another axis associated with the position of the alternate feature. Once the user has completed the calibration for all desired fixation holes, the process is advanced to step 1414 where the user commands the system to exit the calibration program and load a targeting program into system memory.

Figure 15:
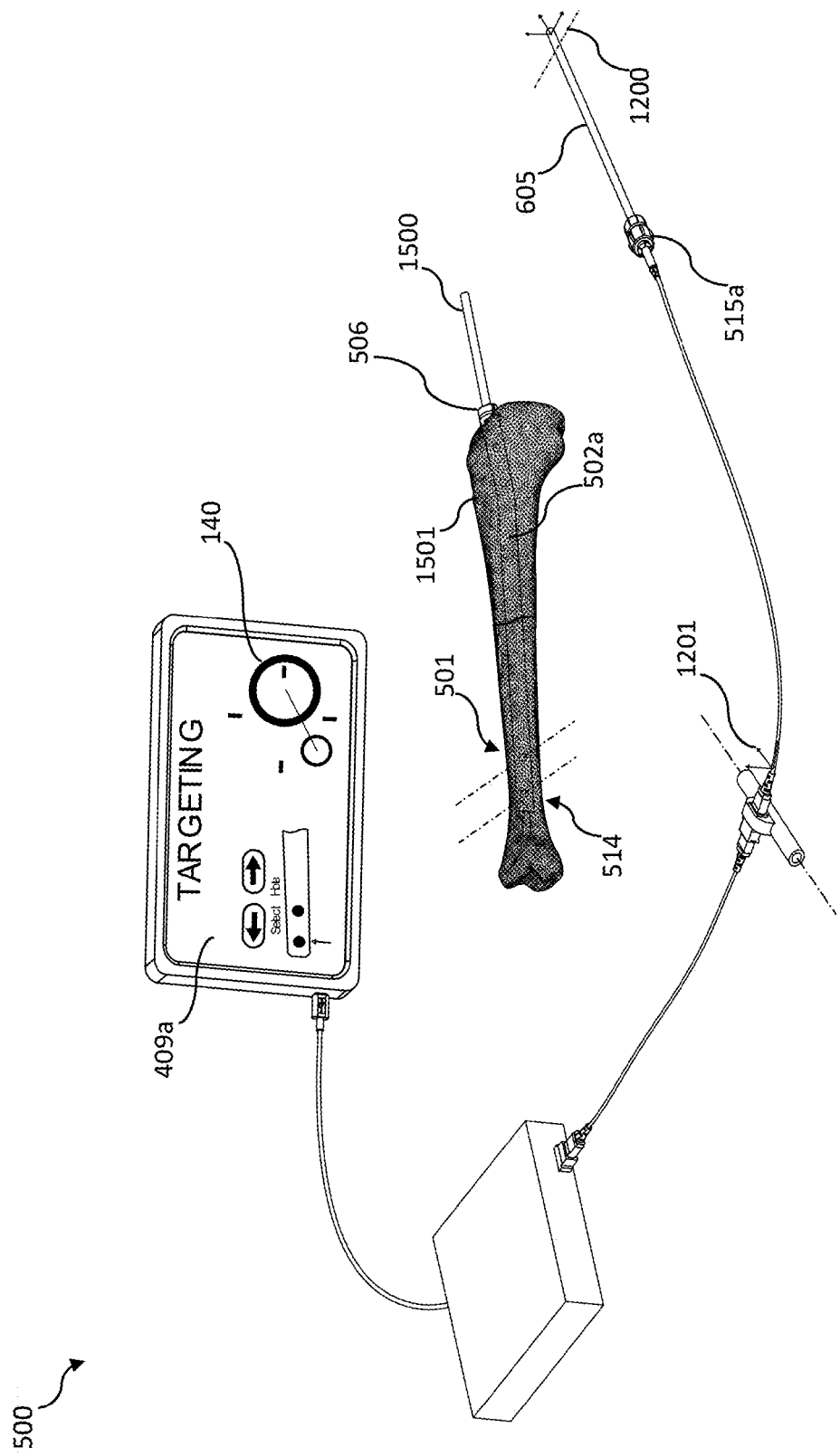
FIG. 15 illustrates the implantation step of a fixation device during a surgical procedure employing the targeting system of FIG. 5, according to an embodiment of the present invention.

With the calibration process is complete, the user may then implant the nail. Referring now to FIG. 15, positioning coupler 515*a* is disconnected from implant adapter 506 enabling probe 605 to be removed from intramedullary nail 502*a*, which may then be introduced over a guidewire 1500 that has been positioned spanning the fracture line in a prepared intramedullary canal of a tibia 1501. In this illustration, distal fixation hole 501 and distal fixation hole 514 are obscured from view by the cortex of tibia 1501 as well as the surrounding soft tissue of the lower leg. It should also be appreciated that a targeting graphic 140, a gunsight type reference image shown on display 409*a*, is indicating that target datum 1200 is not colinear with tool datum 1201.

Figure 16A:
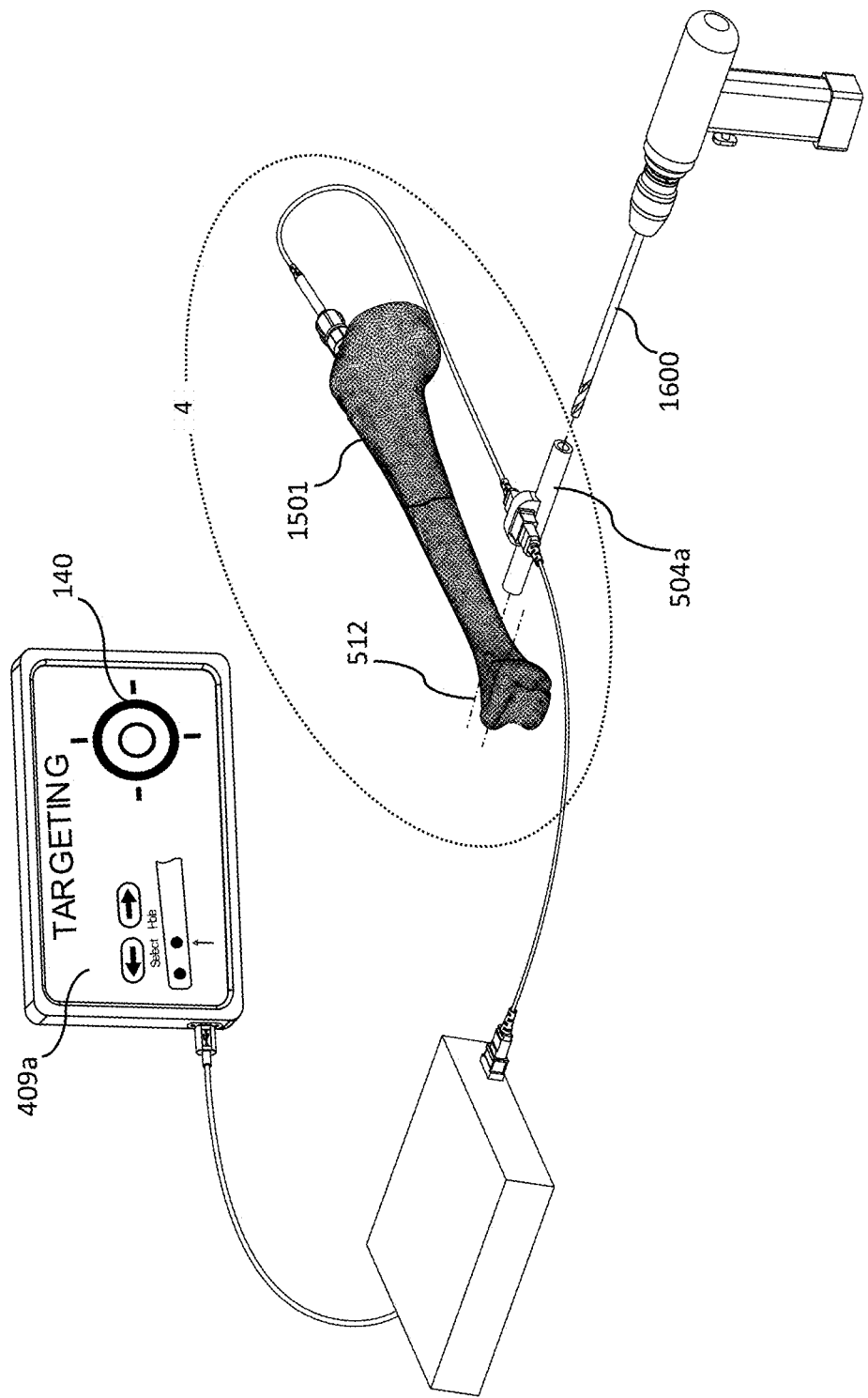
FIG. 16A illustrates the feature targeting step of a surgical procedure employing the targeting system of FIG. 5, according to an embodiment of the present invention.
Figures 16A, 16B:
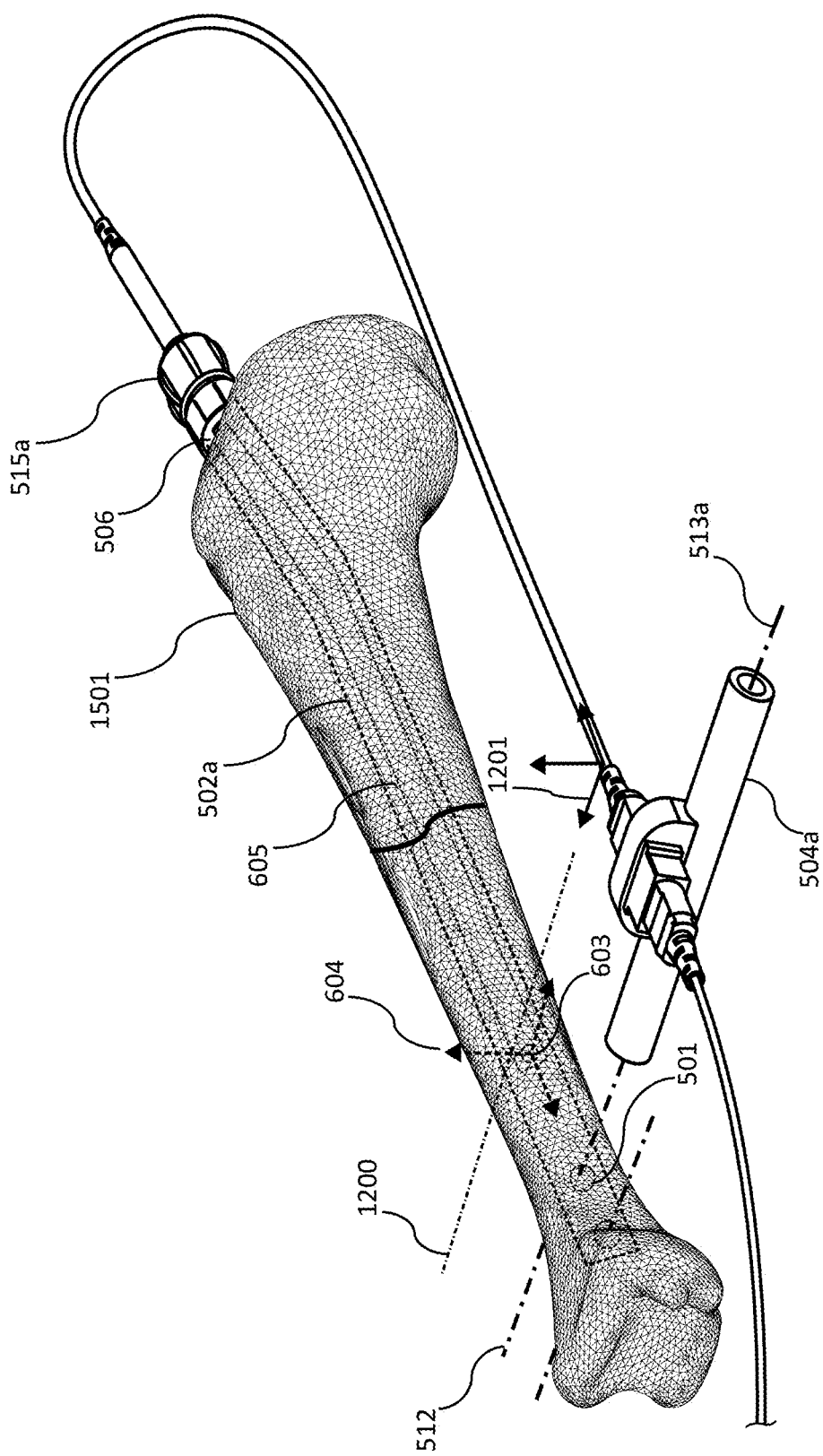
FIG. 16B is a detail view of a portion of the assembly of FIG. 16A, in accordance with the disclosure.

FIGS. 16A-16B illustrate the targeting of distal fixation hole 501 using targeting system 500, according to a embodiment of the present invention. In this view, probe 605 is re-introduced into the lumen of the implanted intramedullary nail 502*a* after guidewire 1500 (not shown) is removed. The user may then reconnect positioning coupler 515*a* onto implant adapter 506, thereby returning target node 603, target reference frame 604, and target datum 1200 to the previously calibrated position and orientation with respect to distal fixation hole 501. In this configuration, the user may select in the targeting program software which fixation hole to target, and refer to the active targeting graphic 140 for tool/hole alignment and drilling. With distal fixation hole 501 as the selected feature for targeting in this example, targeting graphic 140 is assigned to represent the trajectory of tool axis 513*a* with respect to target axis 512 by calculating the degree of offset and skew angle of tool datum 1201 with respect to target datum 1200. With target reference frame 604 returned and fully constrained to its position with respect to distal fixation hole 501 as fixed during the calibration step, the skew angle and offset of tool axis 513*a* with respect to target axis 512 is equivalent to the skew angle and offset of tool datum 1201 with respect to target datum 1200 by definition. In this example, tool datum 1201 is in a position of collinearity with target datum 1200, and may be observed by the user as a fully aligned targeting graphic 140 on display 409*a*, enabling drill 1600 to be passed through drill guide 504*a* to drill a bicortical fixation hole in tibia 1501 colinear with distal fixation hole 501. Once drilling is complete, the user may select to target alternate fixation holes registered in the calibration step.

Figure 17:
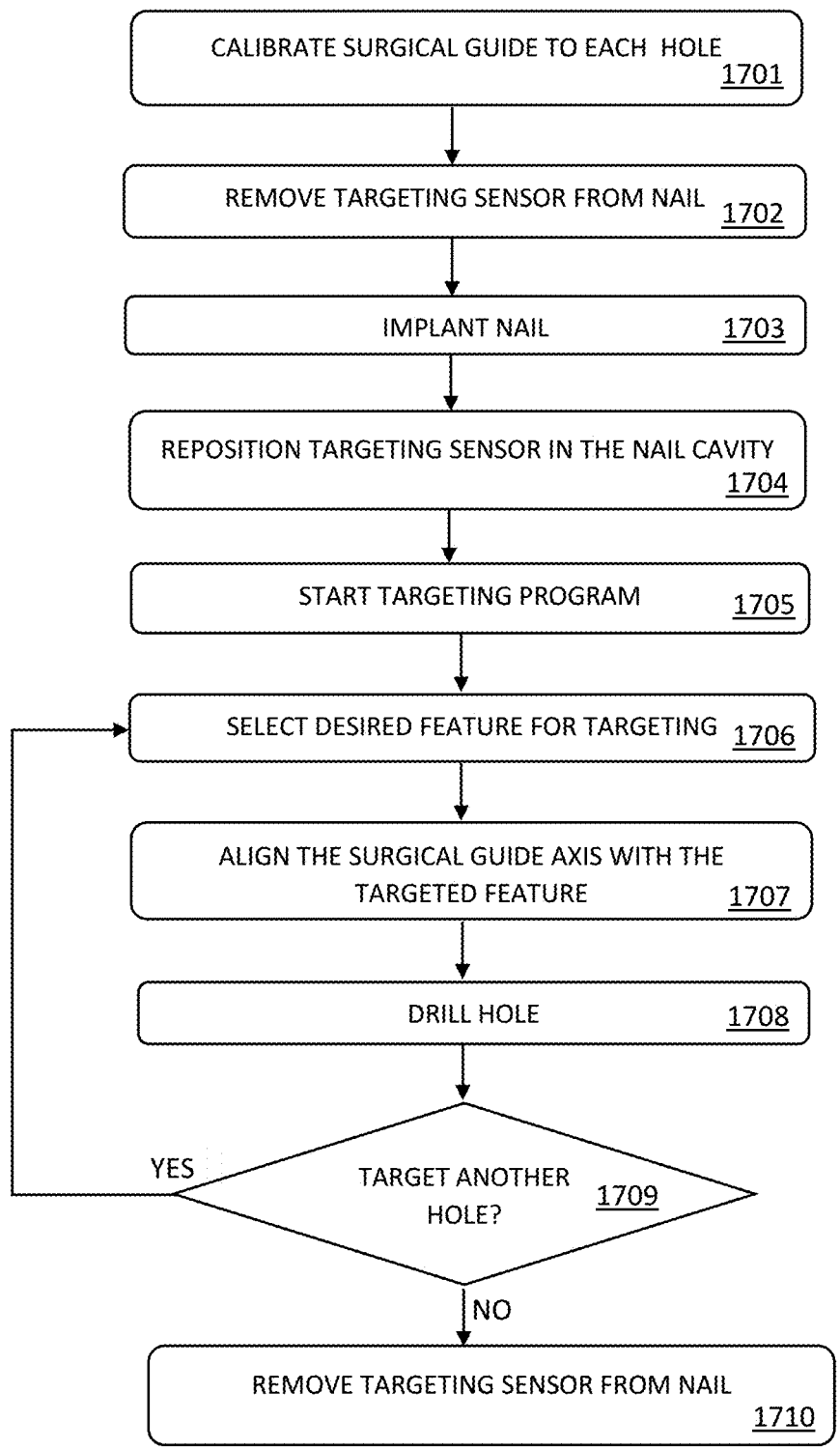
FIG. 17 is a workflow diagram of a targeting process, according to an embodiment of the present invention.

A workflow diagram is presented in schematic form in FIG. 17 to illustrate one method for aligning a surgical tool to a distal fixation hole in an intramedullary nail, according to an embodiment of the present invention. The method begins with step 1701 where a surgical guide is calibrated to at least one target feature. In this example, drill guide 504*a* is calibrated to distal fixation hole 501 as described in FIG. 14. In step 1702, the targeting sensor is removed from the central cavity of the implant to provide space for the implant to be passed over a guidewire. In step 1703, the surgical fixation device is implanted. In this example, intramedullary nail 502*a* is implanted antegrade into tibia 1501 over guidewire 1500 as shown in FIG. 16. In step 1704, the targeting sensor is repositioned in the central cavity of the implant and located in the same position and orientation as the calibration step. In step 1705, the targeting program is selected to be operational to provide the user targeting information that compares the pose of the surgical tool with respect to a targeted feature. In step 1706, the user selects the feature from a list of features calibrated in step 1701 for targeted drilling. In step 1707, the user manipulates the position of the surgical tool while referencing the targeting graphic to align the tool axis to the target axis. In this example, drill guide 504a is aligned to distal fixation hole 501 as described in FIGS. 16A-16B. In step 1708, the user maintains the aligned condition as described in the previous step while advancing a drill, guided by the surgical tool, through the bone and targeted feature. In step 1709, the user chooses to target another calibrated feature and return to step 1706 to select a different fixation hole, or complete the targeting process by advancing to step 1710 and removing the targeting sensor from the nail.

Referring now to FIG. 18, a perspective view of a targeting system 1800 is shown, according to a second embodiment of the present invention, comprising a shape sensing intramedullary nail 1801a connectable to interrogator 400. In this example, calibration information is provided to the user on a portable memory device 1803 which is connectable to a portable control unit 403a. An augmented reality device 1802 is provided as a wearable, head-mounted display enabling the user to view the operative scene, to include the anatomy and surgical instruments in their targeting positions, as well as the targeting graphic targeting selection, or other information useful during the surgical procedure. Augmented reality device 1802 and interrogator 400 may be provided with wireless data transfer equipment to transfer information to and from control unit 403a. Non-limiting examples include but no such as Bluetooth or wireless local area network protocols such as IEEE 802. Control unit 403a, interrogator 400, and augmented reality device 1802 may each be provided with an onboard power supply, such as a rechargeable or replaceable battery, to enable each device mobility and advantageous placement in the operating theater. Portable memory device 1803 may be provided as flash memory, RAM, ROM, EPROM, optical storage, or other computer storage media connectable and operable to transfer electronic data to control unit 403a.

Figure 19A:
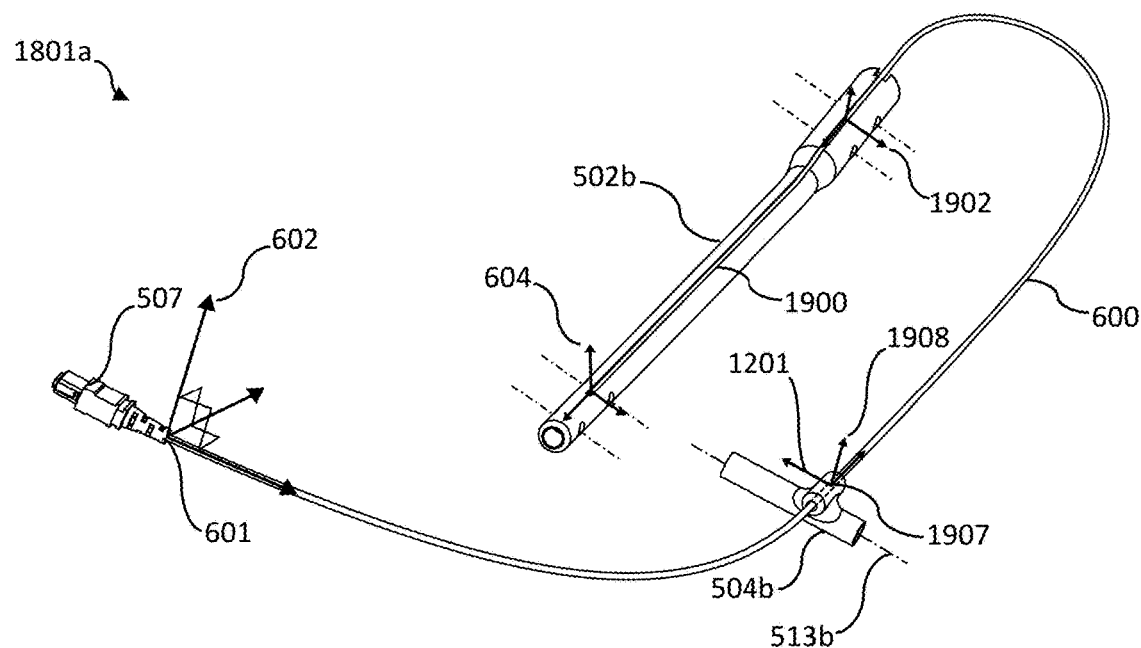
FIG. 19A is a perspective view of an intramedullary nail integrated with a targeting sensor and drill guide, according to an embodiment of the present invention.
Figure 19B:
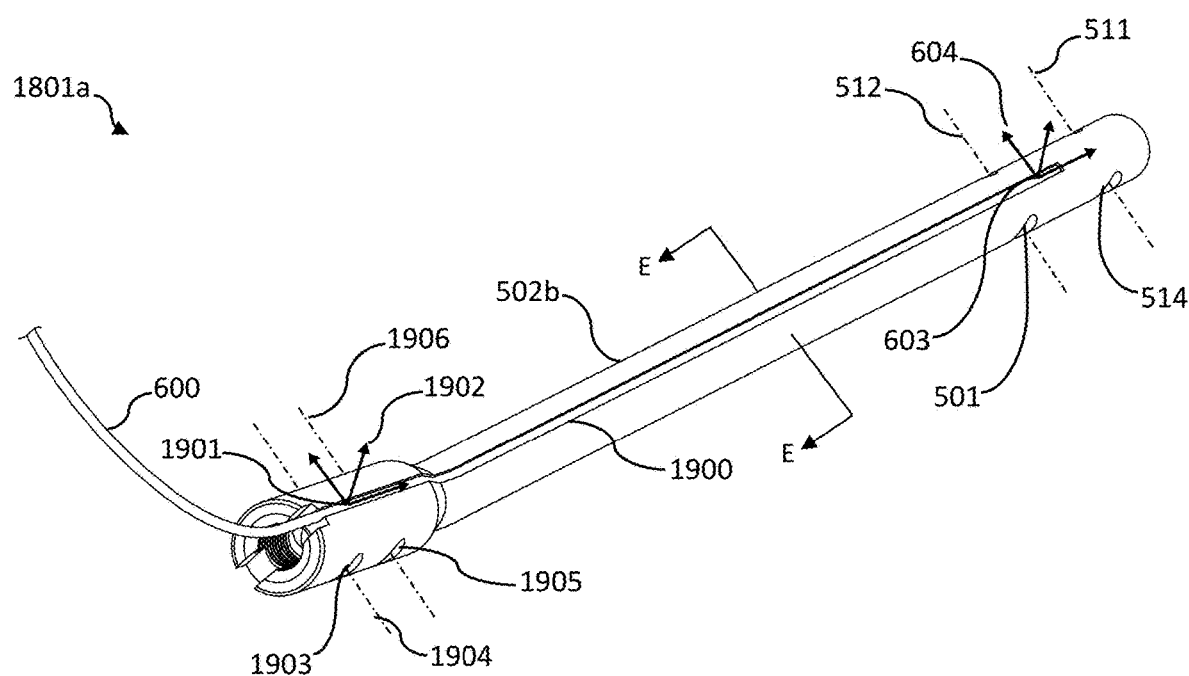
FIG. 19B is a detail view of a portion of the assembly of FIG. 19A, in accordance with the disclosure.

FIGS. 19A-19B are perspective views of shape sensing intramedullary nail 1801a. In this example, an intramedullary nail 502b is integrated with shape sensing cable 600 during the manufacturing process, and the assembly may be packaged sterile to arrive at the user ready for implantation. The first end of shape sensing cable 600 is provided with a male multicore connector 507 for operative connection to interrogator 400, establishing base reference frame 602 at base node 601. A drill guide 504b is attached by injection over-moulding or mechanical means to a middle portion of shape sensing cable 600 having tool axis 513b oriented substantially perpendicular to the central axis of the optical fiber bundle at a tool node 1907. The position and orientation of a tool reference frame 1908, associated with the pose of tool node 1907, is definable in base reference frame 602 by the interrogation and shape reconstruction techniques described heretofore. With tool axis 513b coupled to shape sensing cable 600 at fixed in position with respect to tool node 1907, datums definable in tool reference frame 1908 may be associated thereto. Furthermore, a portion of the distal end of shape sensing cable 600 is fixed in a slot 1900 formed in the outer surface of intramedullary nail 502b, bonding a target node 1901, associated with a target reference frame 1902, to a fixed location with respect to a first proximal fixation hole 1903 having a target axis 1904, and a second proximal fixation hole 1905 having a target axis 1906. A portion near the end of shape sensing cable 600, including target node 603, is bonded in a fixed location with respect to distal fixation holes 501 and 514, as well as target axes 511 and 512, respectively. When interrogated, shape sensing cable 600 is operable to provide the strain information enabling the computation equipment provided in control unit 403a (not shown) to determine the pose of tool reference frame 1908, target reference frame 1902, and target reference frame 604 in base reference frame 602. A skilled artisan will recognize that when multiple child reference frames and datums defined within those reference frames are definable in a common parent reference frame, a first datum defined in a first child reference frame is comparable in position with respect to a second datum defined in a second child reference frame. For example, since the X-axis of tool reference frame 1908 and the X-axis of target reference frame 1902 are both definable in base reference frame 602, the offset and skew angle between the first and second datums are calculable.

FIG. 20A illustrates section and detail views of shape sensing intramedullary nail 1801a, according to the disclosure. In this embodiment, shape sensing cable 600 is pressed into slot 1900 with a fixed fit tolerance during the manufacturing process. Slot 1900 may have depth enabling shape sensing cable 600 to be fully recessed from the outer surface of intramedullary nail 502b. Portions of shape sensing cable 600 extending beyond the outer diameter of intramedullary nail 502b may experience compressive forces between the nail and the inner surface of the canal when implanted, causing strain forces not corresponding to a shape change to be measured and included in the shape reconstruction calculation, which could negatively affect positional accuracy and should be avoided. The portion of shape sensing cable 600 contained in slot 1900 may remain in position during the implantation, and may be removed from intramedullary nail 502b with a modest axial force after all targeted holes have been drilled. It should be noted that with shape sensing cable 600 bonded to intramedullary nail 502b in this configuration, lumen 509 remains accessible for other instrumentation for the duration of the procedure. In an alternative implementation, shape sensing cable 600 may be further secured in slot 1900 of shape sensing intramedullary nail 1801a using a suitable implant grade adhesive 2000 as shown in FIG. 20B. Adhesive 2000 may be any thermoset, thermoplastic or ultraviolet cured polymer or other adhesive approved for long-term residence in tissue. After implantation and hole targeting, shape sensing cable 600 may be cut near the proximal end of intramedullary nail 502b and the remnant discarded. FIG. 20C illustrates a cross section view of a shape sensing intramedullary nail 1801b, according to another embodiment. In this example, an intramedullary nail 502c is manufactured as a composite material consisting of a high-tensile fiber and a thermoplastic, thermoset or ultraviolet-cured polymer matrix where shape sensing cable 600 is embedded in the composite during the layup process.

Figure 21:
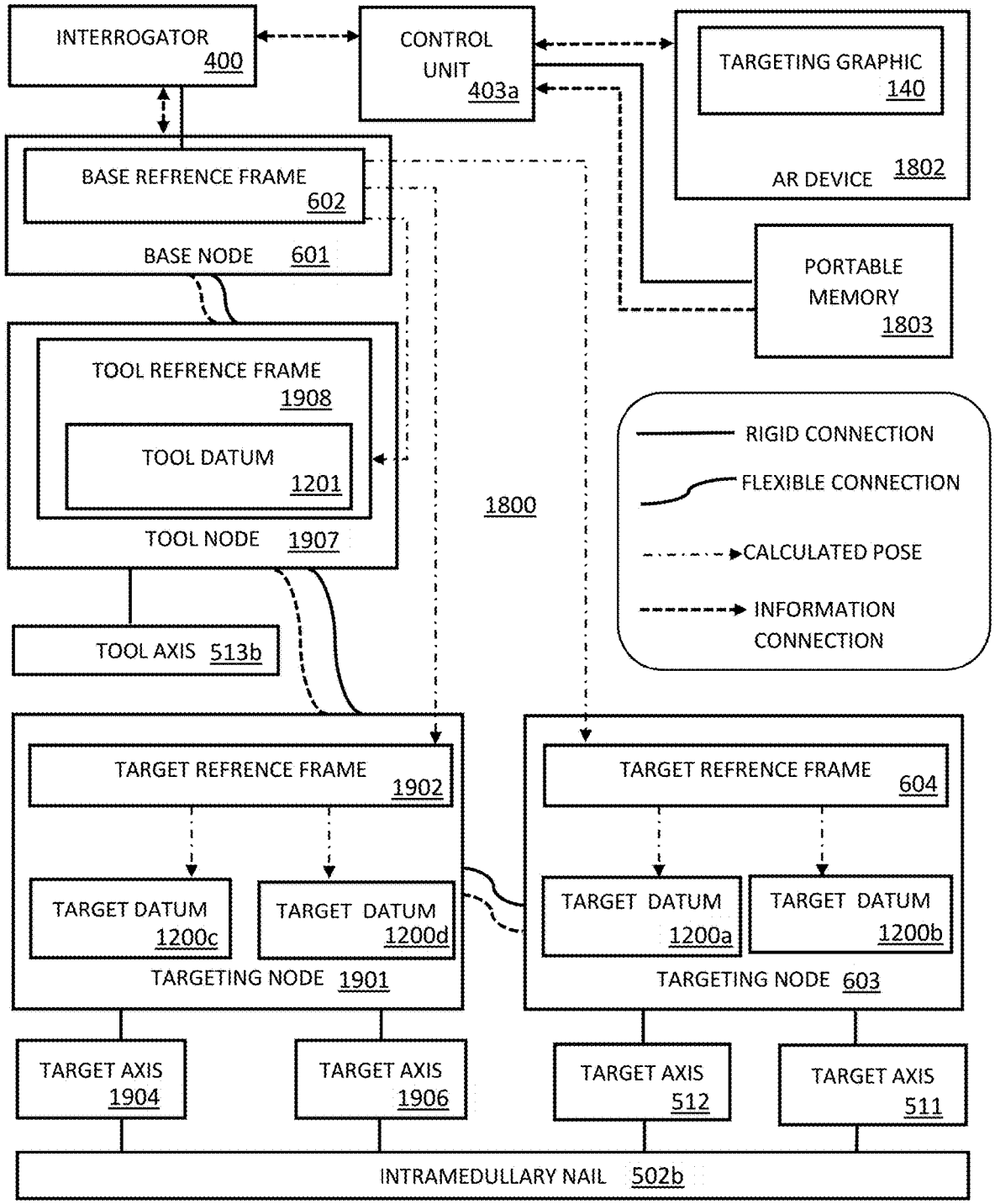
FIG. 21 is a schematic diagram of the targeting system of FIG. 18, according to an embodiment of the present invention.

Referring now to FIG. 21 where a diagram of the major components and connections of targeting system 1800 are illustrated in schematic form. Targeting system 1800 is designed to provide the implant with an integrated targeting sensor where the registered datums associated with targeting each fixation hole are calibrated during manufacturing and supplied with the implant on a portable memory device. This example eliminates the need for the surgical staff to perform the calibration steps prior to implanting the nail saving surgical time. Prior to packaging, a target datum 1200a, associated with target axis 512, and a target datum 1200b, associated with target axis 511, may be defined in target reference frame 604 with respect to tool datum 1201 using the calibration method described in FIG. 14. Similarly, a set of target datums 1200c and 1200d, associated with target axes 1904 and 1906, respectively, are defined in target reference frame 1902. Calibration data is saved on portable memory device 1803 and may be packaged and shipped with the implant. It should be noted that since shape sensing cable 600 is embedded in the outer surface of intramedullary nail 502b and does not occupy the central cavity for calibration or targeting, any screw hole, both in the proximal and distal ends, of intramedullary nail 502b, provided shape sensing cable 600 is routed in a manner to avoid occluding the targeted hole.

Figure 22A:
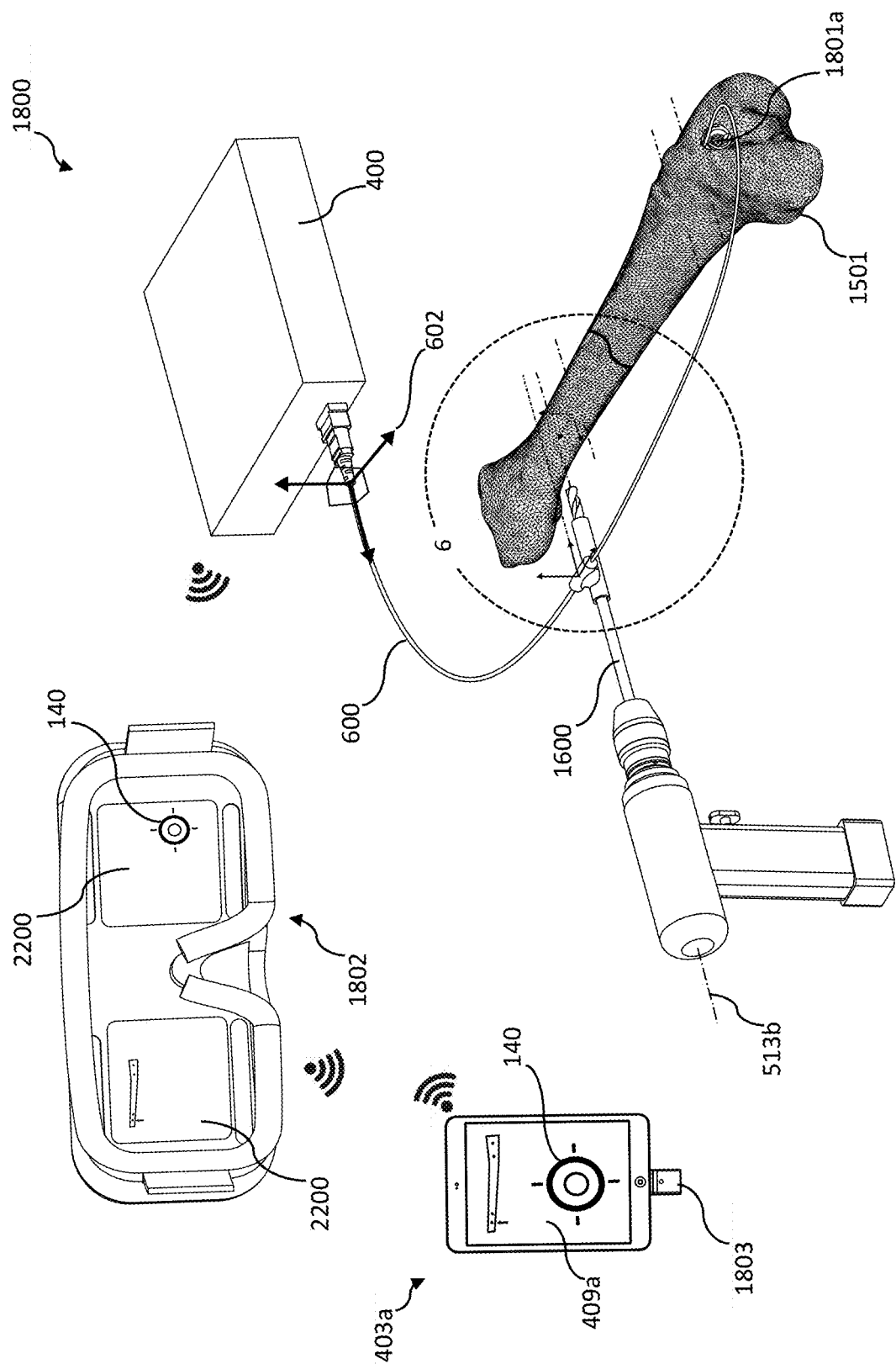
FIG. 22A is a perspective view of the targeting system of FIG. 18 configured for targeting a feature on an implanted intramedullary nail, according to an embodiment of the present invention.
Figures 22A, 22B:
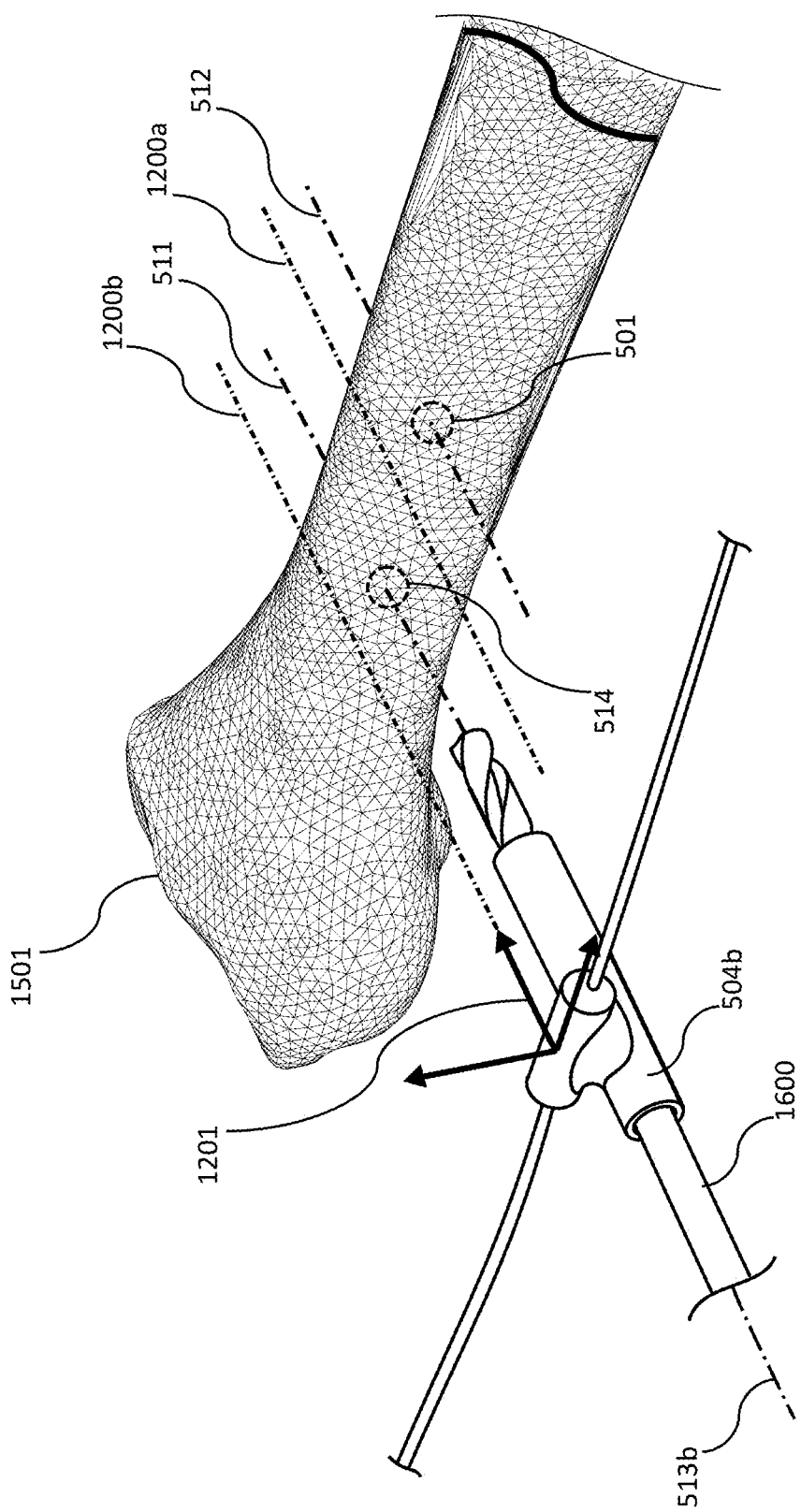
FIG. 22B is a detail view of a portion of the assembly of FIG. 22A, in accordance with the disclosure.

FIGS. 22A-22B are perspective and detail views, respectively, illustrating targeting system 1800 configured for the targeted drilling of a hole in tibia 1501 colinear with distal fixation hole 514. After implanting shape sensing intramedullary nail 1801a into the prepared canal of tibia 1501, the user may connect shape sensing cable 600 to interrogator 400 and initialize the system by confirming communication between interrogator 400, augmented reality device 1802, and control unit 403a. Calibration data may be uploaded to the targeting software by connecting the provided portable memory device 1803 to control unit 403a. In this example, distal fixation hole 514 is selected for targeting, enabling targeting graphic 140 to represent the alignment state of tool axis 513b to target axis 511 by comparing the pose of target datum 1200b with respect to tool datum 1201 in base reference frame 602 as described heretofore. Targeting graphic 140 may be available on display 409a as well as on a screen 2200 mounted on augmented reality device 1802 enabling drill guide 504b, drill 1600, and targeting graphic 140 to be in the user's field of view at the same time. The user may then opt to target distal fixation hole 501 by changing the hole selection in the targeting program. This will change targeting graphic 140 to display the relationship between the pose of drill guide 504b with respect to distal fixation hole 501 by calculating the pose of tool datum 1201 with respect to target datum 1200a, therefore representing the pose of tool axis 513b with respect to target axis 512.

Figure 23:
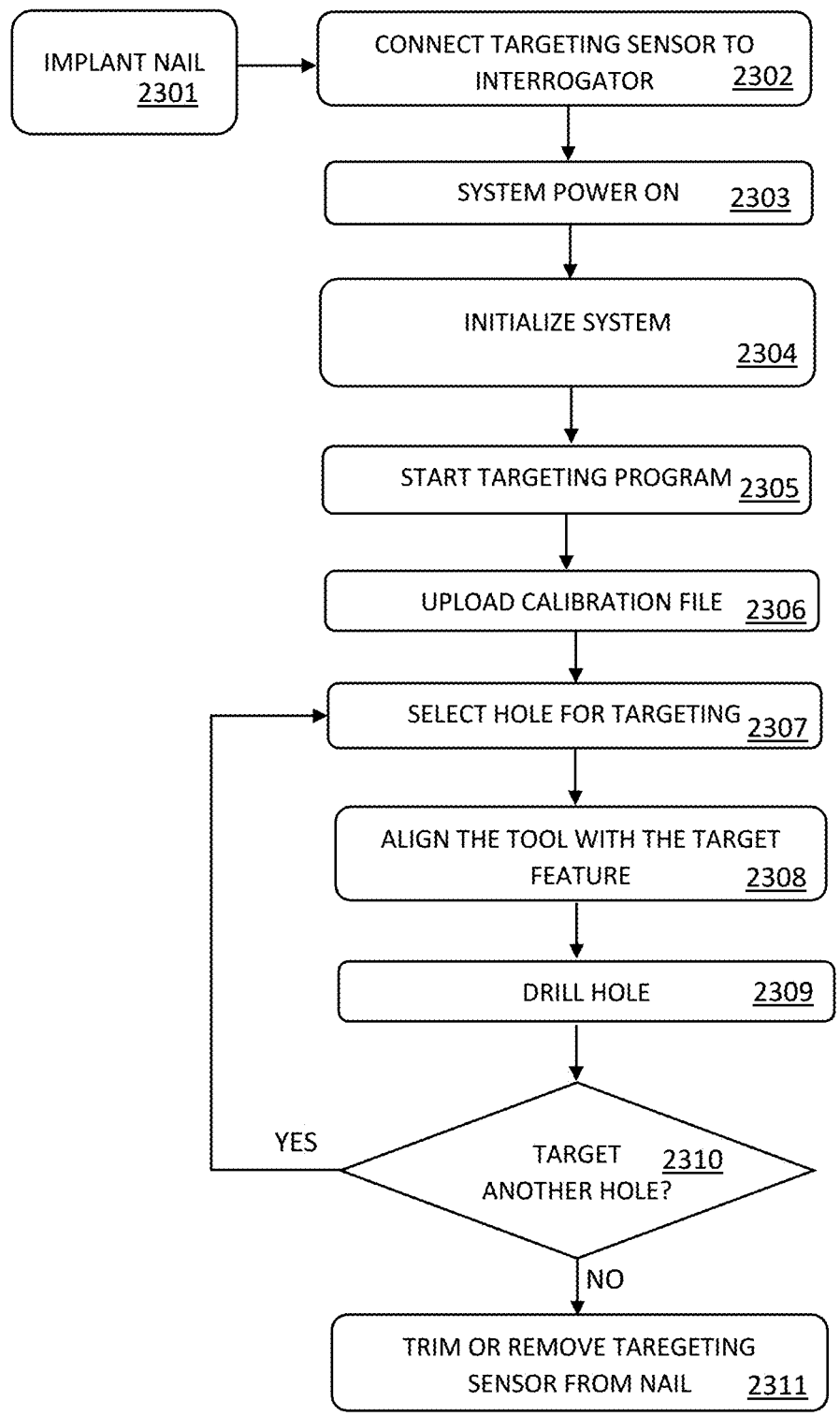
FIG. 23 is a workflow diagram of a targeting process, according to an embodiment of the present invention.

A workflow diagram is presented in schematic form in FIG. 23 to illustrate a method for aligning a surgical tool to a distal fixation hole in an intramedullary nail, according to an embodiment of the present invention. In step 2301, shape sensing intramedullary nail 1801a is removed from the sterile packaging and implanted into the intramedullary canal to reduce the fracture as shown in FIG. 22A. In step 2302, the available end of the targeting sensor is connected to the interrogator. In step 2303, the components of the system are powered on. In step 2304, shape sensing and wireless communication functions are initialized and confirmed operable. In step 2305, the targeting program is loaded into system memory. In step 2306, the portable memory device provided with the implant is connected to the control unit and the calibration file containing the positional information relating the registered axes to the reference datum is uploaded. In step 2307, the user selects the desired hole for targeted drilling. In step 2308, the user manipulates the position of the surgical tool while referencing the targeting graphic to align the tool to the target feature. In this example, drill guide 504b is aligned to distal fixation hole 514 as described in FIGS. 22A-22B. In step 2309, the user maintains the aligned condition as described in the previous step while advancing a drill, guided by the surgical tool, through the bone and targeted feature. In step 2310, the user chooses to target another calibrated feature and return to step 2307 to select a different fixation hole, or complete the targeting process by advancing to step 2311 and remove or trim the targeting sensor from the nail.

Figure 24:
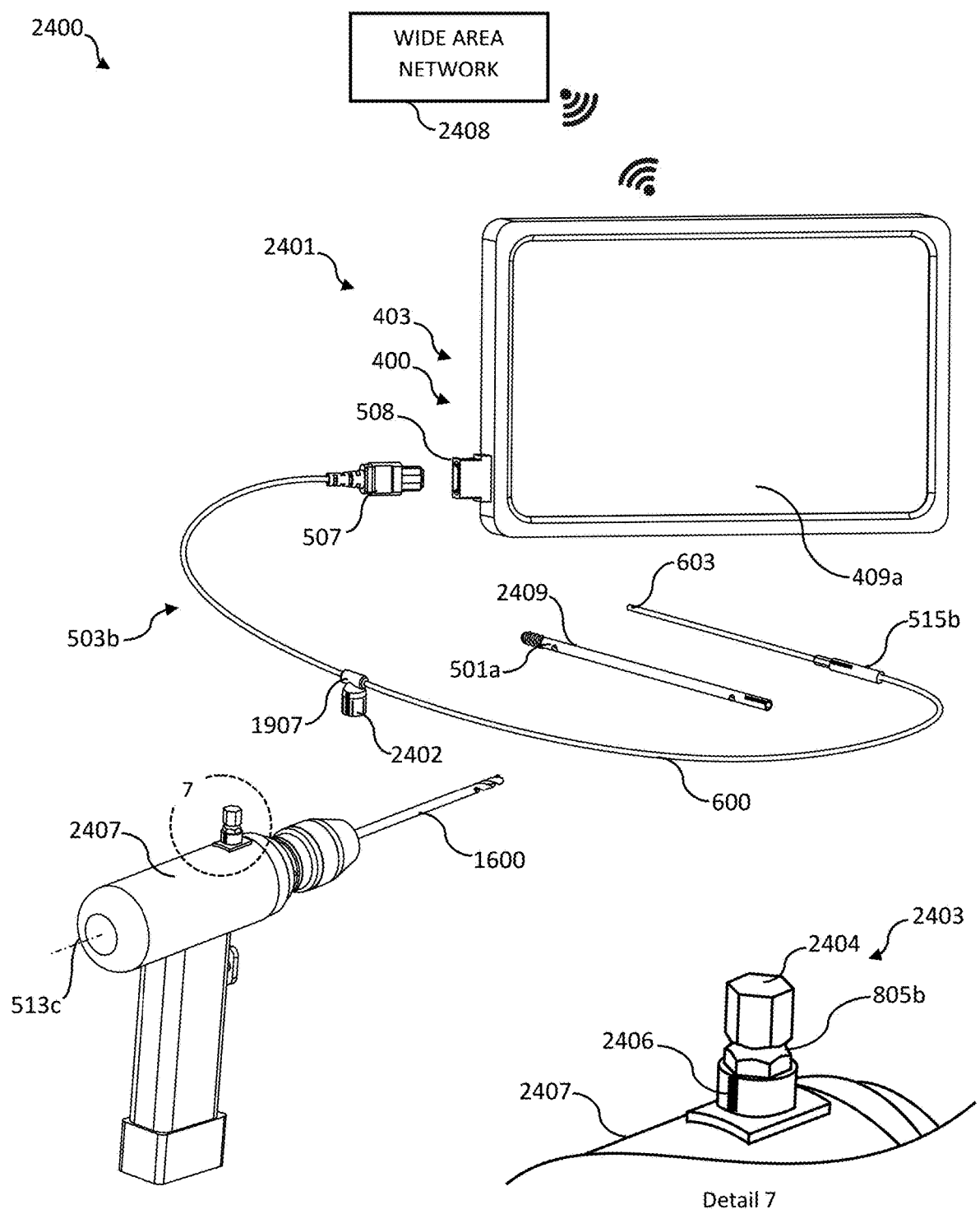
FIG. 24 is a perspective view of a targeting system for aligning a tool to a feature on a surgical device comprising a shape sensing element, according to a third embodiment of the present invention.

FIG. 24 is a perspective view of a targeting system 2400 for aligning a tool to a distal fixation hole 501a formed at the distal end of an intramedullary nail 2409, according to a third embodiment of the present invention. In this example, a control system 2401 is provided comprising interrogator 400, control unit 403, and display 409a in a common housing and operable to connect and interrogate a targeting sensor 503b via female multicore connector 508. Targeting sensor 503b is connectable to interrogator 400 via male multicore connector 507 at a first end of shape sensing cable 600. A tool connector 2402 is rigidly coupled to tool node 1907, and is designed to removably couple to the housing of a drill power 2407 via a mount 2403 to affixed thereto. Mount 2403 is placed at a fixed location with respect to drill 1600, enabling a tool axis 513c, colinear with the long axis of drill 1600, to be coupled in rigid communication with tool node 1907. Mount 2403 is designed having a hexagonal alignment body 2404 and a groove 805b to provide a means to removably connect and locate tool connector 2402. An alignment indicator 2406 is provided as a reference mark to assist the user in connecting tool connector 2402 at a repeatable clock position. A positioning coupler 515b is fixed to shape sensing cable 600 to enable target node 603 to be placed, removed, and reintroduced into the lumen of intramedullary nail 2409 at a repeatable location with respect to a distal fixation hole. Control system 2401 may be connected to a computer network 2408 via a wireless data communication protocol enabling the retrieval of calibration information from a remote library.

Figure 25:
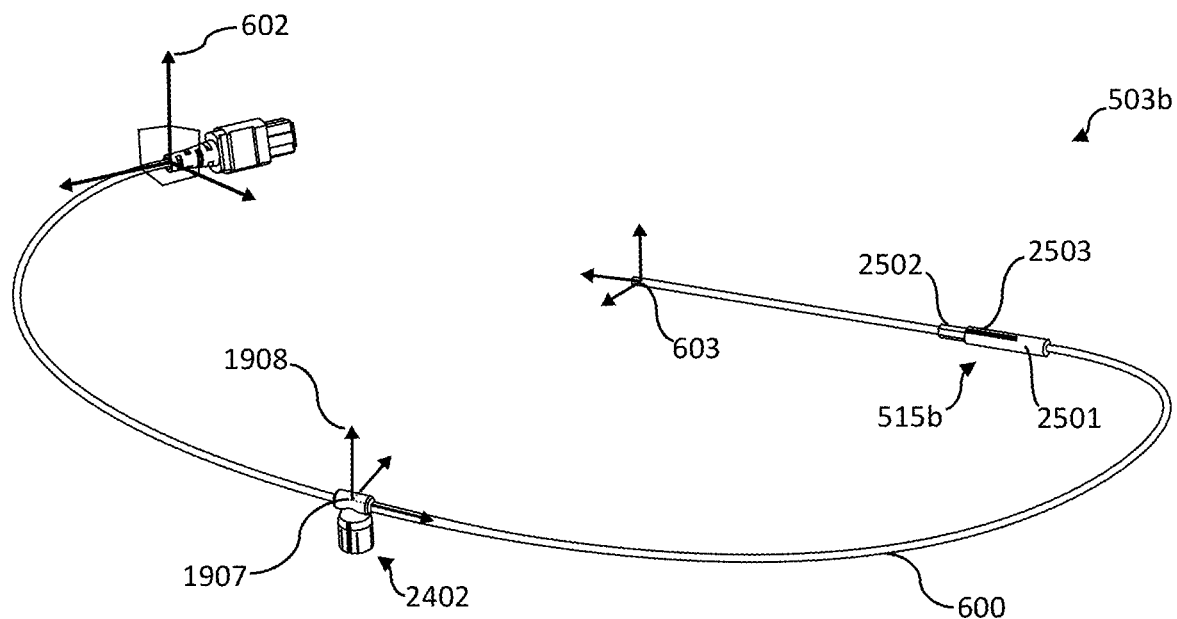
FIG. 25 is a perspective view of the targeting sensor of FIG. 24, according to an embodiment of the present invention.

Referring now to FIG. 25, where targeting sensor 503b is illustrated in perspective view, in accordance with the disclosure. Targeting sensor 503b is designed such that a variety of surgical tools may connect to tool connector 2402 with the tool's operative axis coupled in rigid communication with tool node 1907 and datums defined in tool reference frame 1908 and its pose with respect to target node 603 tracked in base reference frame 602. It may be advantageous to disconnect the surgical tool from targeting sensor 503b after calibration for use in other surgical tasks, and then reconnect for hole targeting. A portion of shape sensing cable 600 is designed to be insertable in the lumen of an intramedullary nail with target node 603 oriented with the aid of positioning coupler 515b mated with features formed in the proximal end of the implant. In this example, positioning coupler 515b is injection over-moulded onto shape sensing cable 600 having a hexagonal alignment body 2502 which extends toward target node 603 from a cylindrical handle 2501. An alignment indicator 2503 is inscribed on handle 2501 as a reference mark to assist the user in connecting positioning coupler 515b to the proximal end of the implant at a repeatable clock position.

Figure 26:
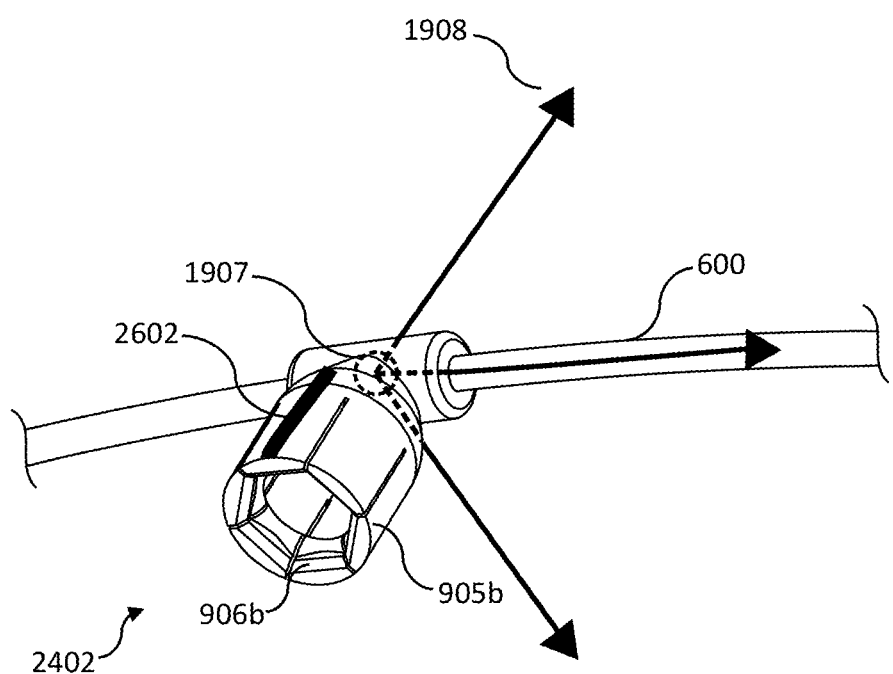
FIG. 26 is a perspective view of the tool connector of FIG. 25, according to an embodiment of the present invention.

FIG. 26 is a perspective view of tool connector 2402 rigidly coupled to tool node 1907 of shape sensing cable 600. Tool connector 2402 may be coupled to shape sensing cable 600 by an injection over-moulding process with a clip 905b extending perpendicularly from one side of the cable. Clip 905b is designed to removably engage with mount 2403 (illustrated in FIG. 24) and comprises a series of elastic tangs extending from the distal end and arranged around the circumference to enable removable connection. Formed in the inner hexagonally-shaped cavity of clip 905b is an axial key 906b, designed to engage with groove 805b on mount 2403. An alignment indicator 2602 is formed on the exterior of clip 905b to server as a reference mark to assist the user in connecting tools to targeting sensor 503b at a repeatable clock position with respect to tool node 1907. When assembled, datums in rigid communication with mount 2403 are fixed in position with respect to tool node 1907 and tool reference frame 1908.

Figures 27A, 27B:
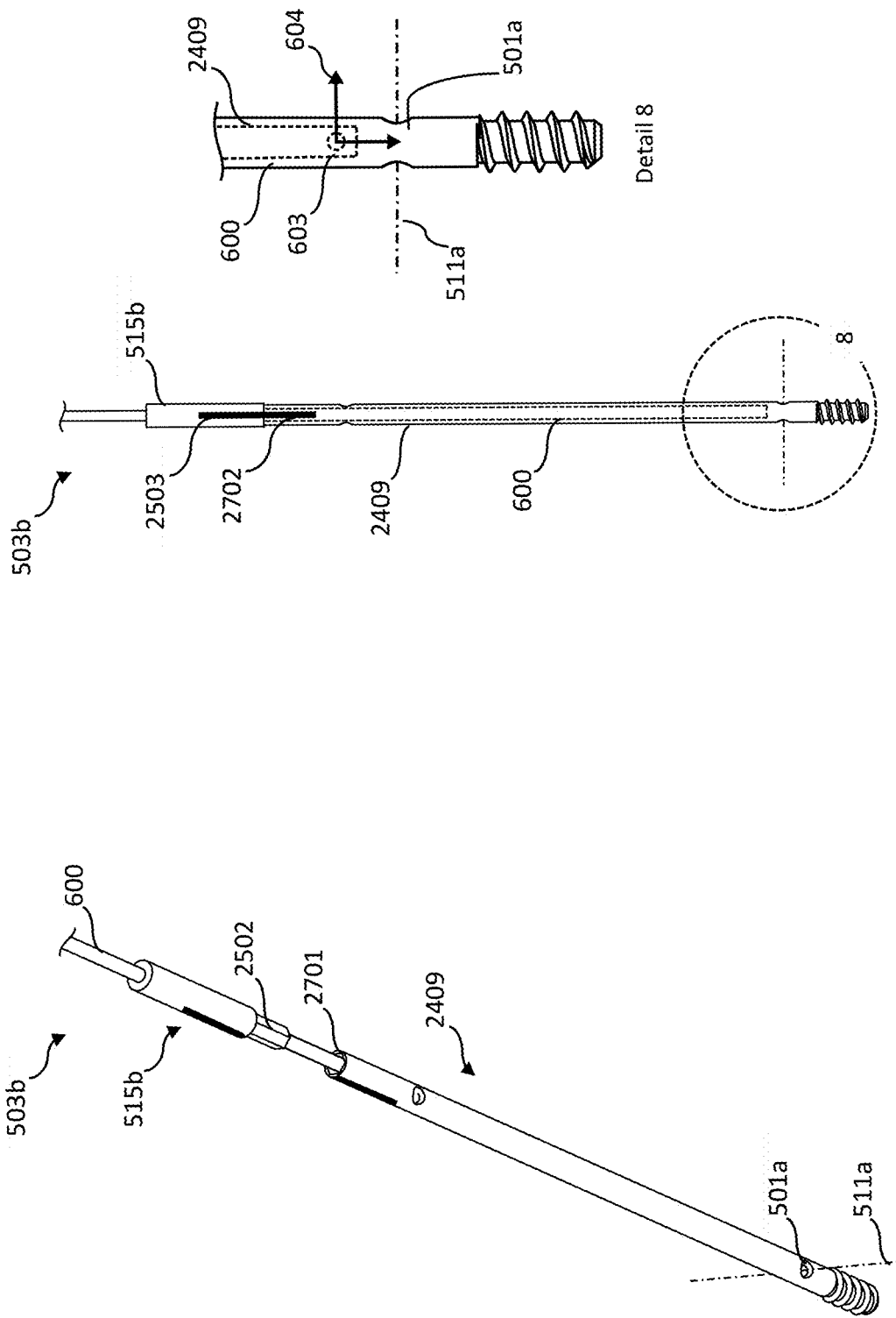
FIG. 27A is a perspective view of the targeting sensor of FIG. 24 coupled to an intramedullary nail, according to an embodiment of the present invention.
FIG. 27B is a front view of the targeting sensor of FIG. 24 coupled to an intramedullary nail, according to an embodiment of the present invention.

As shown in FIGS. 27A-27B, targeting sensor 503b is placed in the lumen of intramedullary nail 2409. The diameter of shape sensing cable 600 is designed to have a close sliding fit with the lumen of intramedullary nail 2409. It should be noted that careful consideration be given to the combination of the material choice for coating 700 (illustrated in FIG. 7A) and sliding fit tolerance. Coating 700 should provide the necessary stiffness and elastic properties to allow minor torsional stresses from the rotational alignment of shape sensing cable 600 to distal fixation hole 501a during insertion to be dissipated, allowing the rotational orientation of target node 603 with respect to alignment indicator 2503 to be consistent and repeatable. In addition, a close sliding fit, where mating components clearances are minimized while allowing sliding or rotation, should be used between shape sensing cable 600 and cavity wall of intramedullary nail 2409 to maximize targeting accuracy by reducing the available positional variation of target node 603 with respect to distal fixation hole 501a having a target axis 511a. Alignment body 2502 is designed to have a fixed fit with a hexagonal shaped hex drive 2701 formed in the proximal end of intramedullary nail 2409 to enable a secure connection between positioning coupler 515b and intramedullary nail 2409, and removable with light pressure. Placing targeting sensor 503b with alignment indicator 2503 and an alignment indicator 2702, formed at the proximal end of intramedullary nail 2409, aligned as illustrated locates target node 603 and target reference frame 604 in rigid communication with target axis 511a.

Figure 28:
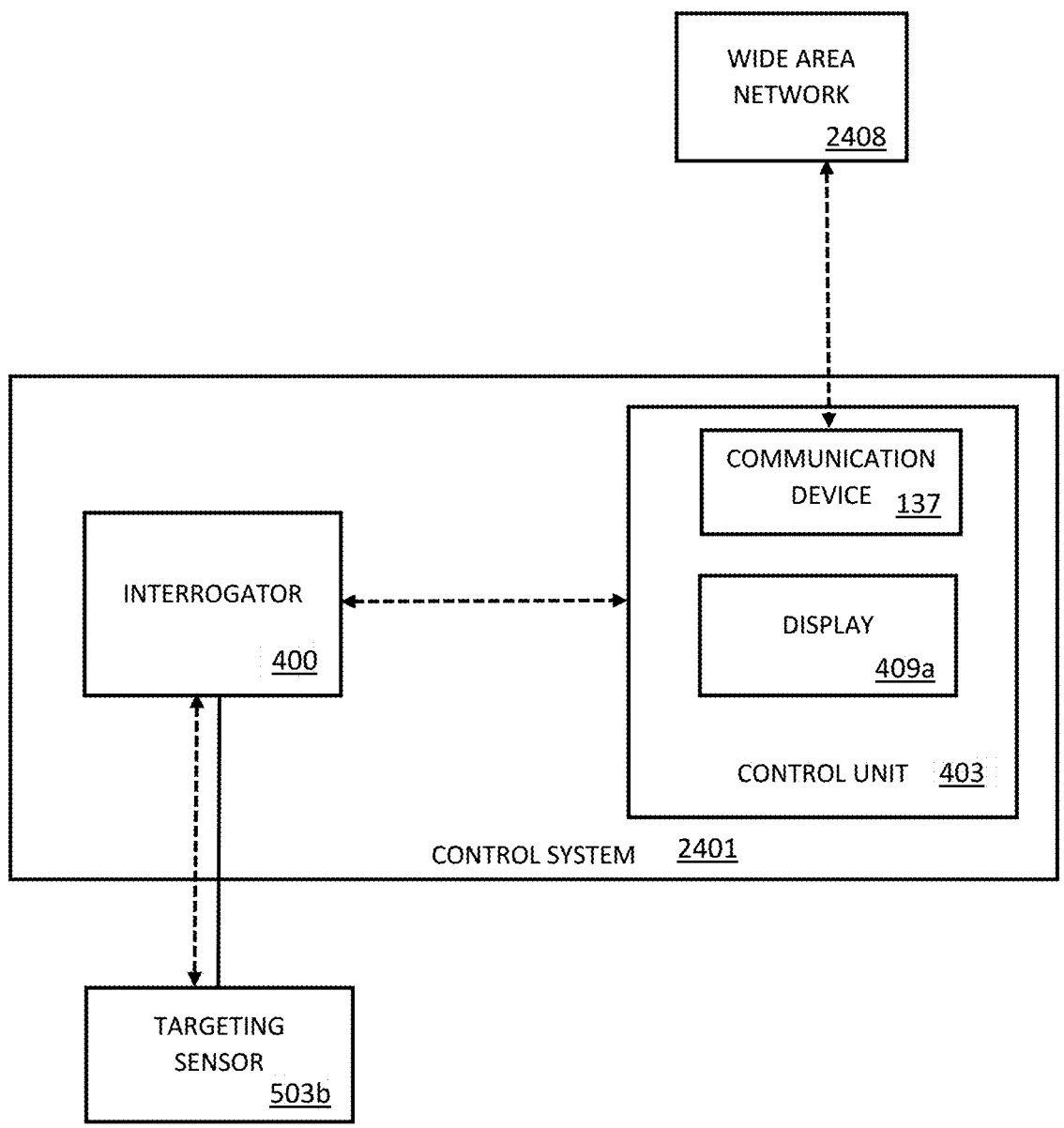
FIG. 28 is a schematic diagram of the control system of FIG. 24, according to an embodiment of the present invention.

Referring now to FIG. 28 where diagrams of the major components and connections of control system 2401 are illustrated in schematic form, in accordance with the disclosure. In some implementations it may be advantageous to combine the electronic components that remain located outside the sterile field of an operating theater into one unit to reduce the number of components for cost reduction. A single housing having a larger display 409a is also possible, enabling control system 2401 to be set father away from the sterile field while remaining viewable to the user.

Figure 29:
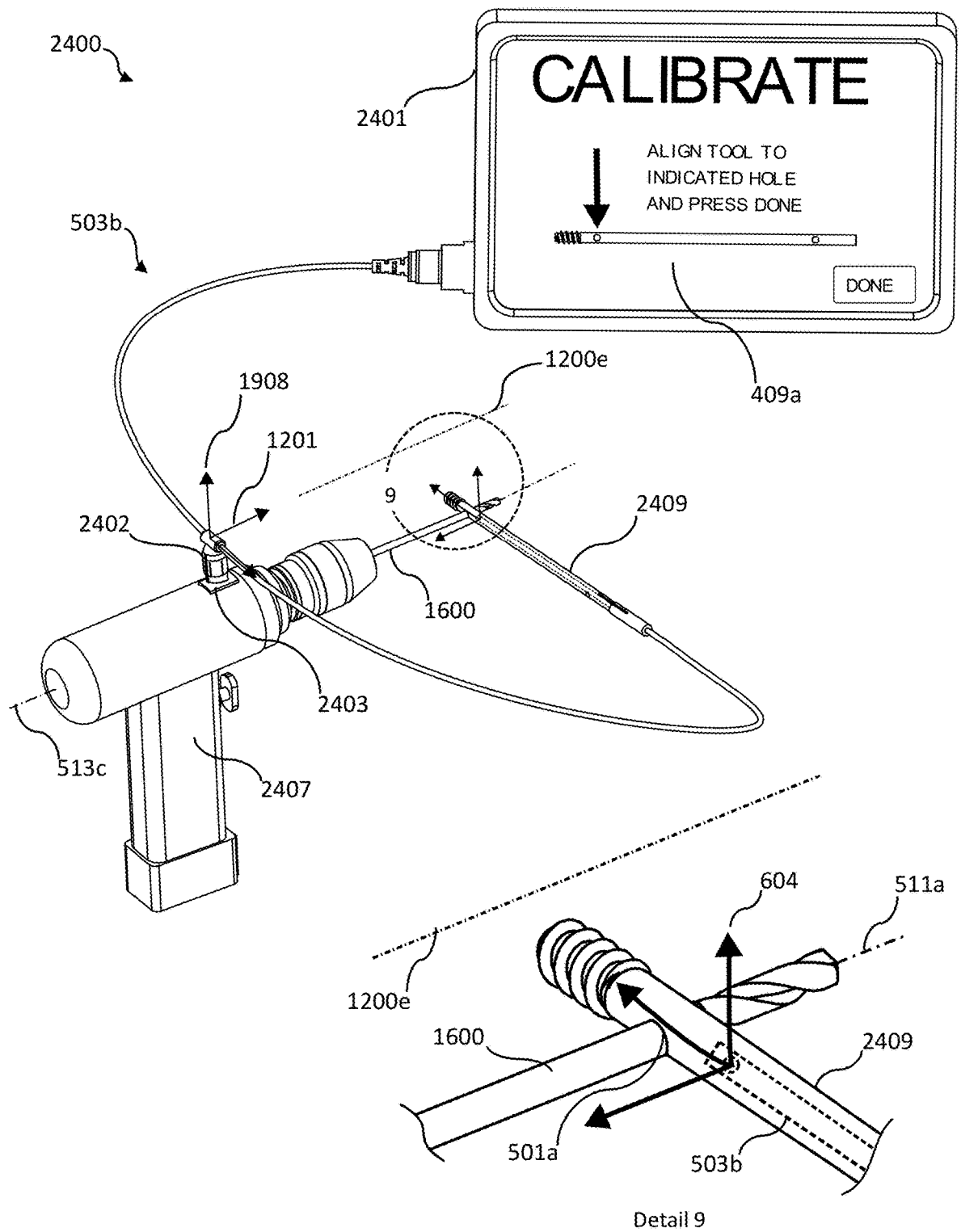
FIG. 29 is a perspective view of the targeting system of FIG. 24 coupled to an intramedullary nail and configured for calibrating the targeting sensor to a targeted feature, according to an embodiment of the present invention.

One useful advantage provided by targeting system 2400 is the capability for the user to connect a variety of surgical tools to targeting sensor 503b. In the cases where a calibration of the tool axis to the targeted feature is not available for remote retrieval from computer network 2408, the system may be configured for impromptu calibration as shown in FIG. 29. Targeting sensor 503b is connected to control system 2401 and a calibration program is loaded into system memory after initialization with instructions viewable on display 409a. Once the interrogation and shape reconstruction functions are confirmed operable, drill power 2407 is connected to targeting sensor 503b by coupling tool connector 2402 to mount 2403 with indicating marks aligned to establish tool axis 513c at a fixed pose with respect to tool reference frame 1908. Targeting sensor 503b is the coupled to intramedullary nail 2409 as described in FIGS. 27A-27B to establish target reference frame 604 at a fixed pose with respect to target axis 511a. Tool axis 513c is aligned colinear with target axis 511a by placing drill 1600 in distal fixation hole 501a. A target datum 1200e is then defined in target reference frame 604 colinear to tool datum 1201. The user may then save the calibration and load the targeting program into system memory.

After completing the calibration, targeting sensor 503b is removed from the cannulation of intramedullary nail 2409 and tool connector 2402 may be removed from mount 2403, as shown in FIG. 30. A hex driver 3001 is coupled to drill power 2407, operable to connect and provide torque to the proximal end of intramedullary nail 2409 for implantation in a clavicle 3000. It may be appreciated in this illustration that targeting graphic 140, shown on display 409a, is indicating that target datum 1200e is not colinear with tool datum 1201.

Figure 31:
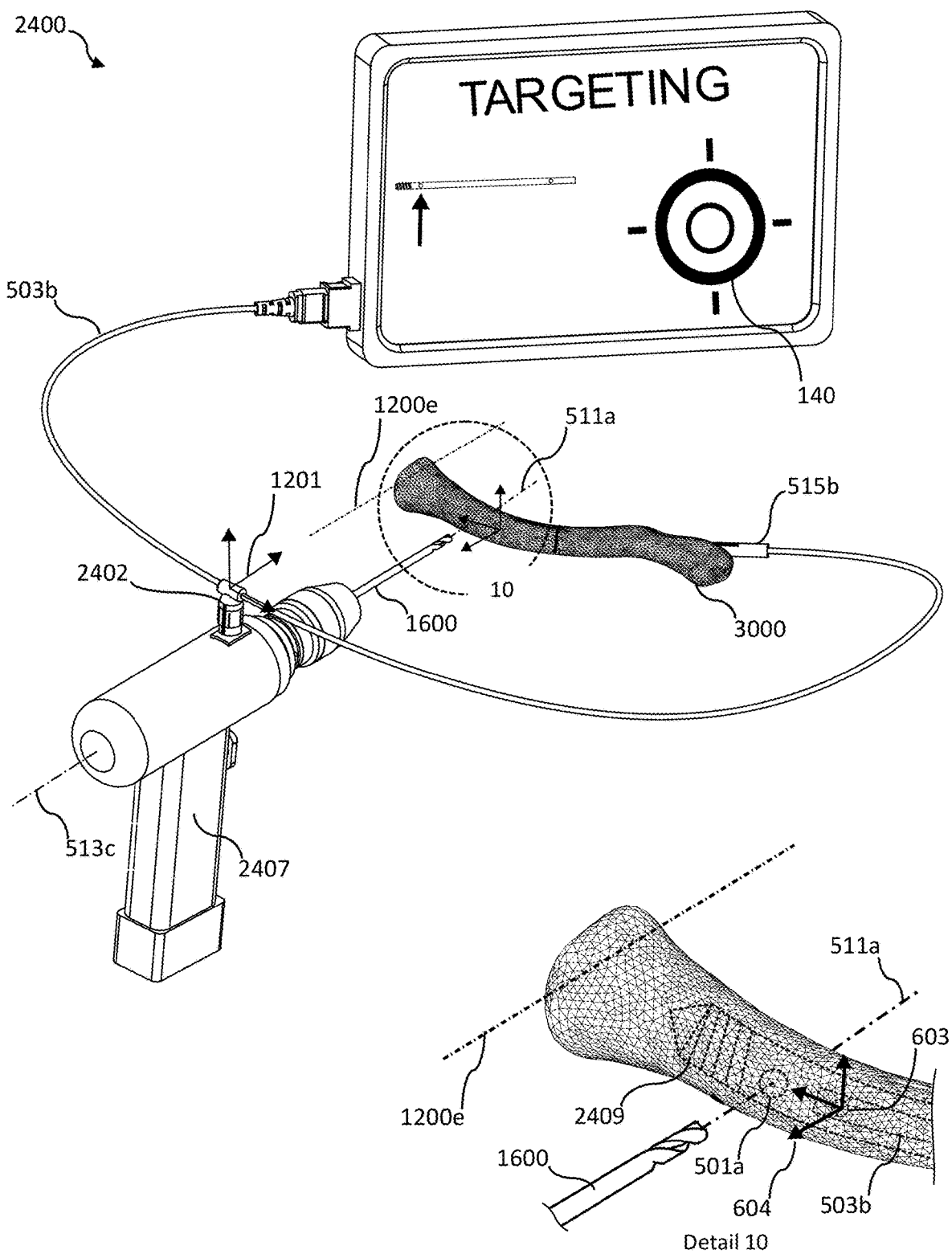
FIG. 31 illustrates the targeting step of a surgical procedure employing the targeting system of FIG. 24, according to an embodiment of the present invention.

FIG. 31 illustrates a perspective view of targeting system 2400 configured for the targeting distal fixation hole 501a, according to an embodiment of the present invention. With tool connector 2402 reconnected to drill power 2407 and targeting sensor 503b reintroduced into the lumen of intramedullary nail 2409 in their calibrated positions, target node 603 and target reference frame 604 are returned to their calibrated positions with respect to tool axis 513c, which is colinear with drill 1600. Targeting graphic 140 is assigned to represent the trajectory of tool axis 513c with respect to target axis 511a by calculating the degree of offset and skew angle of tool datum 1201 with respect to target datum 1200e. As previously described, the skew angle and offset of tool axis 513c with respect to target axis 511a is equivalent to the skew angle and offset of tool datum 1201 with respect to target datum 1200e by definition. In this illustration, tool datum 1201 is shown in a position of collinearity with target datum 1200e, and may be observed by the user as a fully aligned targeting graphic 140, enabling a bicortical fixation hole in clavicle 3000 colinear with distal fixation hole 501a to be drilled.

Figure 32:
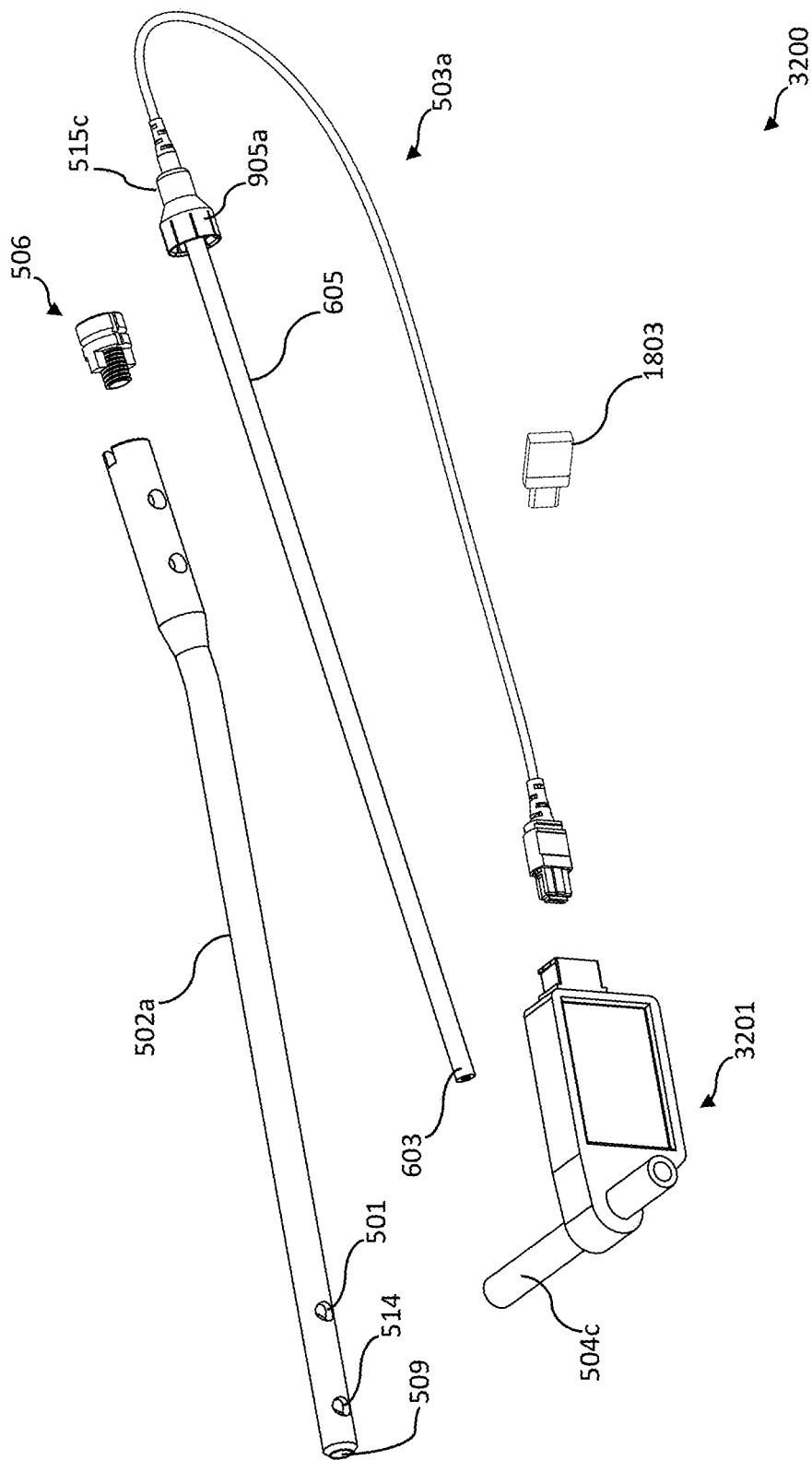
FIG. 32 is a perspective view of a targeting system for aligning a tool to a feature on a surgical device comprising a shape sensing element, according to a fourth embodiment of the present invention.

FIG. 32 is a perspective view of a targeting system 3200 for aligning a surgical tool to a distal fixation hole formed in intramedullary nail 502a, according to a fourth embodiment of the present invention. In this example, targeting sensor 503a is connected to a handheld control system 3201 which has an integrated drill guide 504c. A positioning coupler 515c may be fixed onto probe 605 with clip 905a operative to engage implant adapter 506, enabling target node 603 to be positioned in lumen 509 and removably coupled in rigid communication with distal fixation holes 501 and 514 as described in the first embodiment of this discussion. Calibration information may be generated prior to packaging and provided to the user on portable memory device 1803 for upload to control system 3201.

Figure 33A:
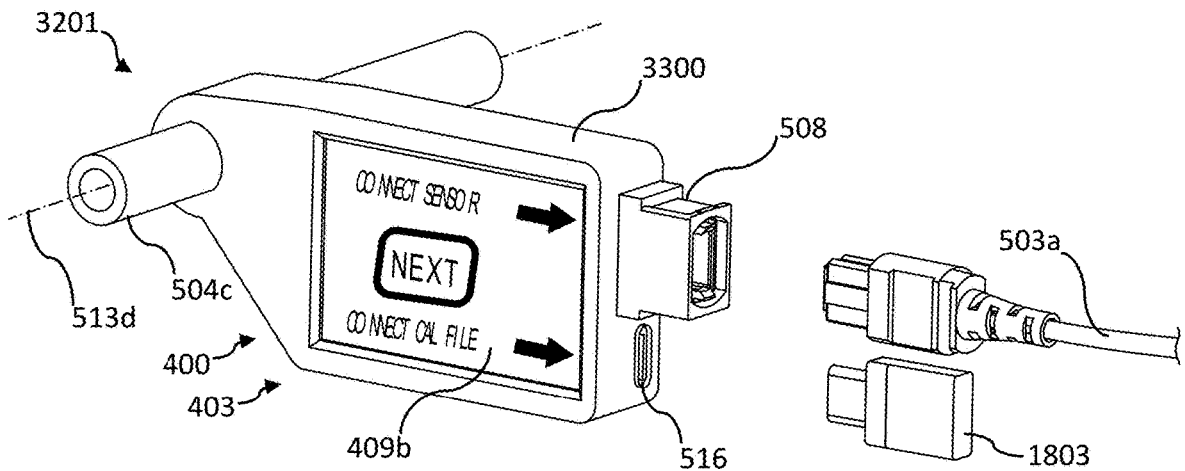
FIG. 33A is a perspective view of the handheld control system of FIG. 32, according to an embodiment of the present invention.
Figure 33B:
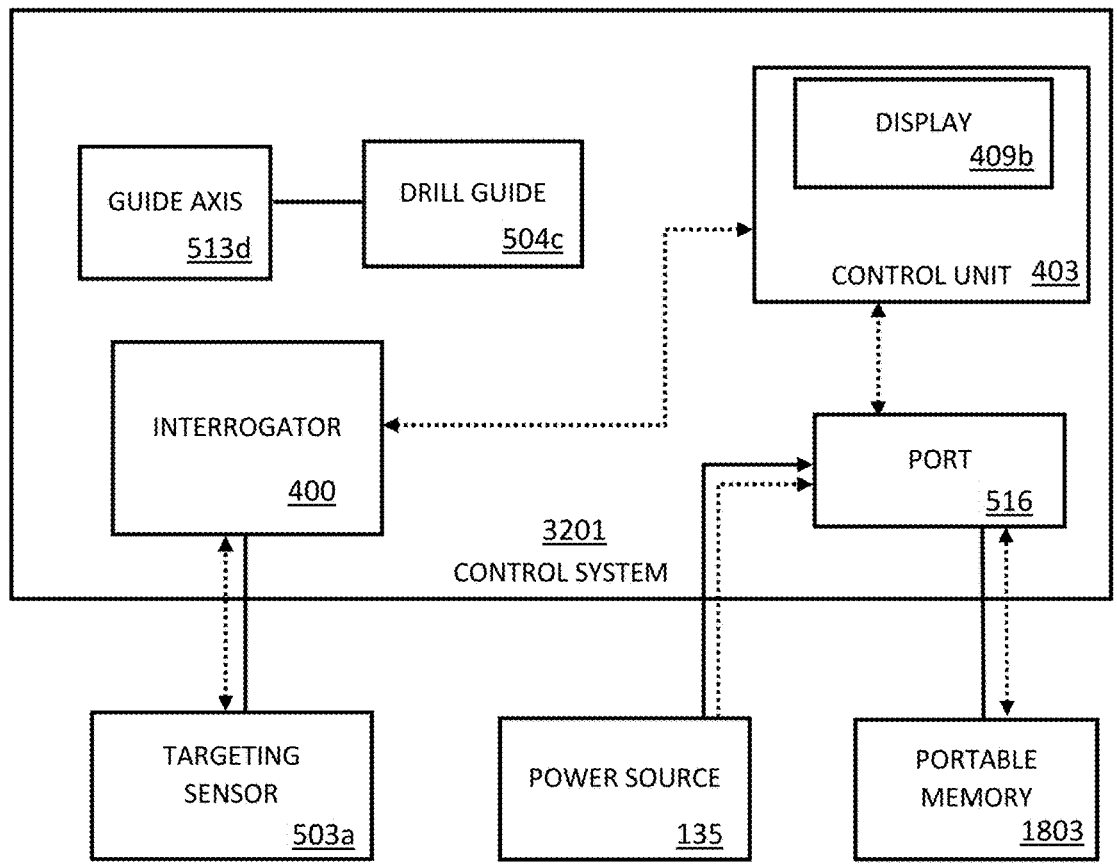
FIG. 33B is a schematic diagram of the handheld control system of FIG. 32, according to an embodiment of the present invention.

FIG. 33A illustrates a perspective view of control system 3201, which is intended to be a stand-alone component used inside the sterile field at the drilling site with interrogator 400, control unit 403, and a display 409b arranged in a common housing 3300. Control system 3201 may be provided to the user as a packaged, single-use, sterile component which may be presented into the sterile field for use and returned to the manufacturer for reconditioning and repackaging, or designed to tolerate autoclave steam sterilization processes commonly available at surgical centers. Targeting sensor 503a is operatively connected to control system 3201 via female multicore connector 508 and port 516 may be provided to connect portable memory device 1803 for uploading calibration information to control unit 403 or to connect to a power source 135 (shown in FIG. 33B) for operation or to recharge an onboard battery. In this example, drill guide 504c, with a tool axis 513d, is shown fixed in position in housing 3300 as an injection moulded assembly, but may also be provided as a separate component connectable to housing 3300 in rigid communication with female multicore connector 508. A diagram of the major components of control system 3201 is provided in schematic form in FIG. 33B for appreciation.

Figure 34:
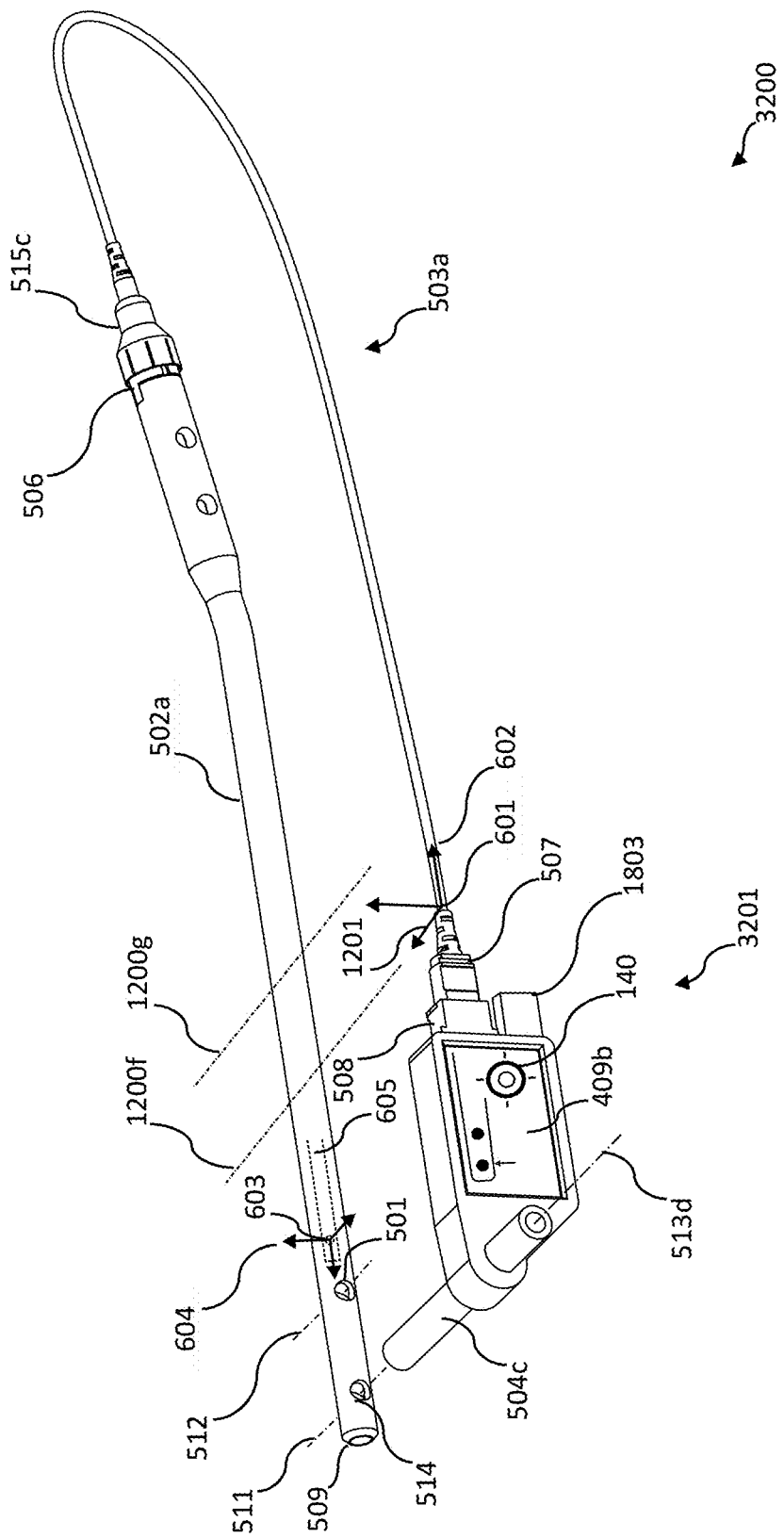
FIG. 34 illustrates the targeting step of a surgical procedure employing the targeting system of FIG. 32, according to an embodiment of the present invention.

Referring now to FIG. 34, where targeting system 3200 is shown configured for aligning drill guide 504c to distal fixation hole 514. In this view, implant adapter 506 is assembled onto the proximal end of intramedullary nail 502a with probe 605 inserted into lumen 509. With positioning coupler 515c connected to implant adapter 506, target node 603 and target reference frame 604 are therefore located at a calibrated position with respect to distal fixation holes 501 and 514. Targeting sensor 503a is then connected to control system 3201 and the system may be initialized. Calibration data uploaded to control system 3201 from portable memory device 1803 enable the definition of a target datum 1200f corresponding to target axis 511, and a target datum 1200g corresponding to target axis 512. With male multicore connector 507 rigidly connected to female multicore connector 508, tool axis 513d is rigidly fixed with respect to base node 601 and base reference frame 602. In this illustration, distal fixation hole 514 is selected for targeting and indicated on display 409b. Targeting graphic 140 is assigned to represent the trajectory of tool axis 513d with respect to target axis 511 by calculating the degree of offset and skew angle of tool datum 1201 with respect to target datum 1200f. As previously described, the skew angle and offset of tool axis 513d with respect to target axis 511 is equivalent to the skew angle and offset of tool datum 1201 with respect to target datum 1200f by definition from the calibration. Tool datum 1201 is shown here in a position of collinearity with target datum 1200f, and may be observed by the user as a fully aligned targeting graphic 140 on display 409b.

Figure 35:
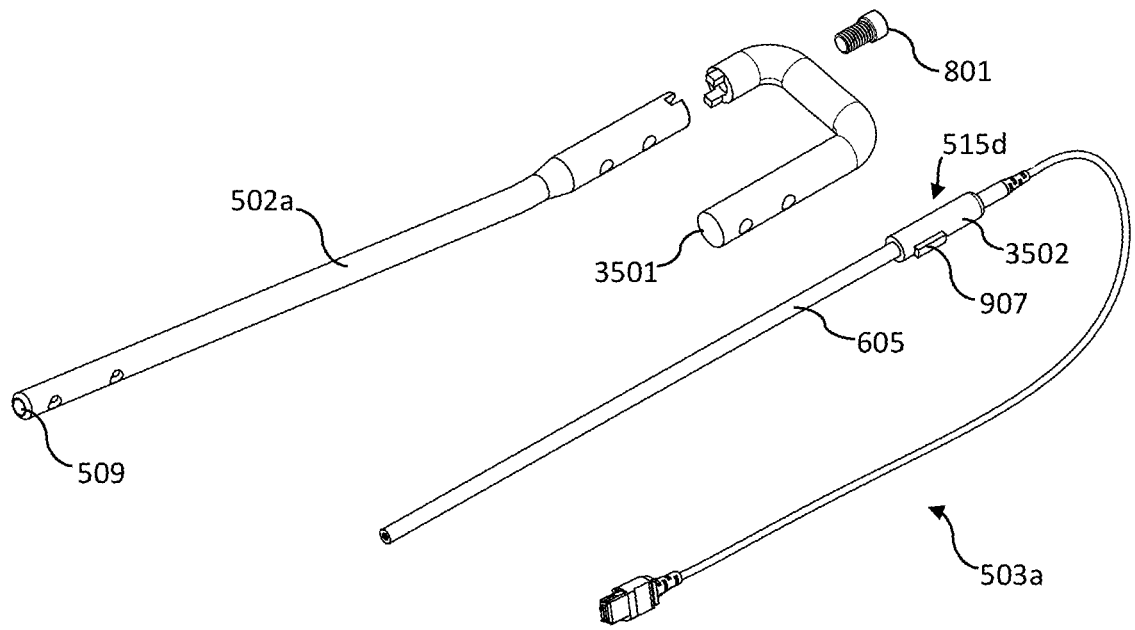
FIG. 35 is an exploded view of an alternate configuration of the targeting sensor and coupler of the targeting system of FIG. 32, according to an embodiment of the present invention.

In certain situations, the surgeon may elect to attach guiding or other instrumentation to the proximal end of an intramedullary nail to aid in insertion into the bone or other fracture reduction steps. As shown in FIG. 35, an insertion handle 3501 may be provided which is secured to intramedullary nail 502a using bolt 801. In this example, a positioning coupler 515d, comprising a cylindrical probe handle 3502 having rotational key 907, is affixed to probe 605 designed to couple with insertion handle 3501 for the localization of targeting sensor 503a in lumen 509.

Figure 36A:
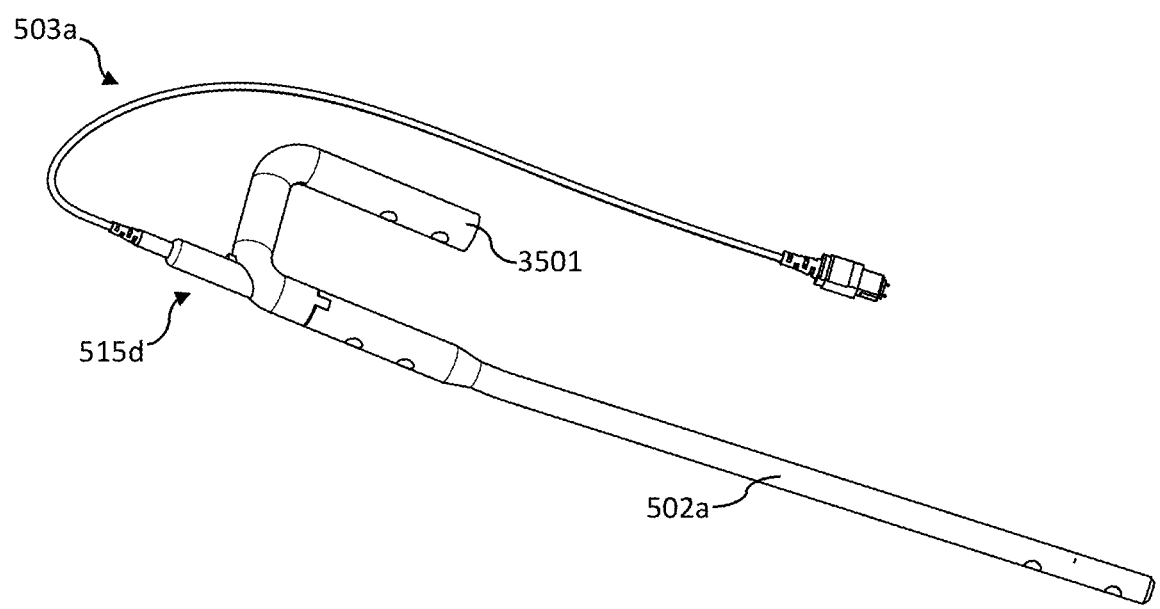

Referring now to FIGS. 36A-36C, where a perspective, top, side and section views are shown to illustrate the coupling of insertion handle 3501 and targeting sensor 503a to intramedullary nail 502a. In this example, insertion handle 3501 is designed to provide the user with a means to control the rotation of intramedullary nail 502a in the bone during implantation, as well as provide guide apertures 3600 and 3601 for the targeted drilling of proximal fixation holes 1903 and 1905, respectively. Insertion handle 3501 is also designed to enable the rigid and removable connection of positioning coupler 515d to place target node 603, located at the end of probe 605 as previously described, in rigid and removable connection with respect to target axes 511 and 512 as shown in FIG. 36B. Referring now to the section view F-F of FIG. 36C, where the assembly is further illustrated. Probe handle 3502 is designed to be secured by the user with a fixed fit in a locating aperture 3602, formed in insertion handle 3501 and removable with light pressure. Axial location and rotational position of positioning coupler 515d are limited by the engagement of rotational key 907 in slot 804.

Figure 37:
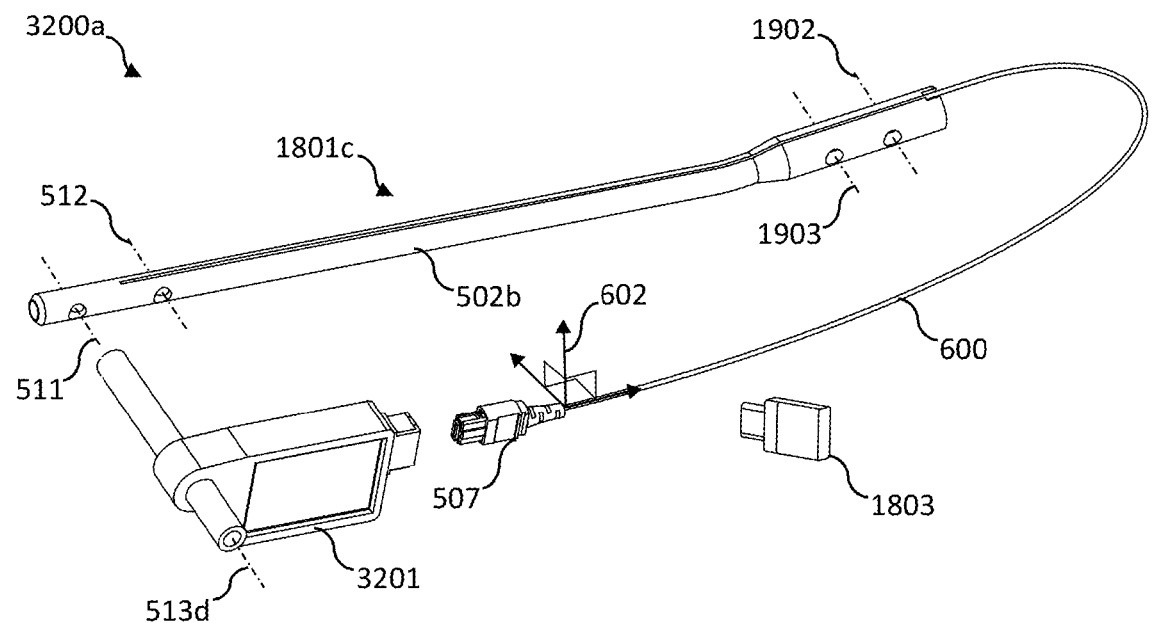
FIG. 37 is a perspective view of a targeting system for aligning a tool to a feature on a surgical device comprising a shape sensing element, according to a fifth embodiment of the present invention.
Figure 38:
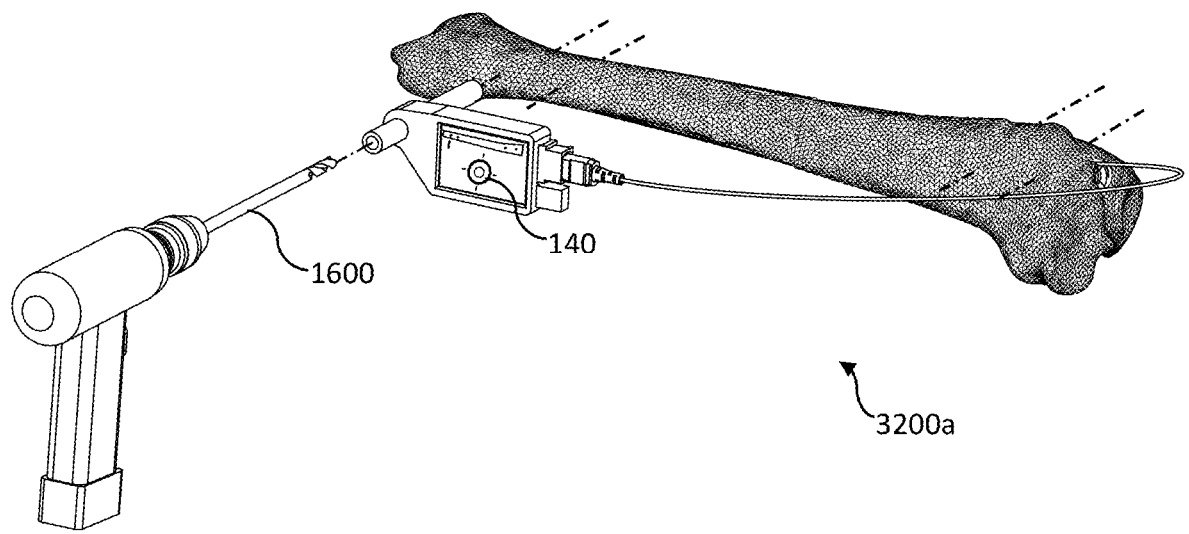
FIG. 38 illustrates the targeting step of a surgical procedure employing the targeting system of FIG. 37, according to an embodiment of the present invention.

FIG. 37 is a perspective view of a targeting system 3200a for aligning a surgical tool to a distal fixation hole formed in intramedullary nail 502b, according to a fifth embodiment of the present invention. A shape sensing intramedullary nail 1801c is provided to the user having shape sensing cable 600 coupled to intramedullary nail 502b in similar fashion as shown in FIGS. 19A-19B with the pose of targeting nodes and targeting reference frames trackable in base reference frame 602, connectable to control system 3201 via male multicore connector 507 for interrogation, as described in the second embodiment of this discussion. Portable memory device 1803 may be supplied with the implant where the calibration information may be stored and uploaded to handheld control system 3201 to enable the pose of tool axis 513d to be compared to target axes 511, 512, 1902, and 1903 as previously described. As shown in FIG. 38, targeting system 3200a provides the user with the ability to target blind fixation holes in both the proximal and distal segments of the nail with both drill 1600 and targeting graphic 140 in the field of view simultaneously.

Though this discussion has disclosed embodiments of the invention relating to the targeting of features on an intramedullary rod, the type of implant should not be limiting to the scope of the invention. For example, fixation holes or other features in bone fixation plates, holes or features in intramedullary stems relating to joint arthroplasty or targeting other blind features in bone or other tissues for the connection to or retrieval of surgical instruments of implants.

What is claimed is:

1. A system for targeting a feature on a surgical device, comprising:
   a shape sensing element having a first element end and a second element end and a plurality of nodes dispersed therein, the first element end coupled to an interrogator, wherein the shape sensing element is operable to receive an interrogation signal from the interrogator and return a modified signal to the interrogator related to the position and orientation of each node in a coordinate system, wherein a first node is coupled in communication with a surgical tool and at least a second node is coupled in communication with at least one target feature on a surgical device, wherein the position and orientation of the first node in the coordinate system defines a tool reference frame and the position and orientation of the at least second node in the coordinate system defines a target reference frame;
   an interrogator operable to provide the interrogation signal to and receive the modified signal from said shape sensing element to generate interrogation information related to the position and orientation of the nodes in the coordinate system, and provide the interrogation information to a data processing system; and
   a data processing system operable to: a) receive the interrogation information from the interrogator, b) interpret the interrogation information to determine the position and orientation of the nodes in the coordinate system, c) compare the pose of a tool datum definable in the tool reference frame with respect to at least one target datum definable in the at least one target reference frame, and d) provide information related to the comparison to a display;
   wherein the surgical tool comprises a first tool end and a second tool end and a tool axis therebetween,
   wherein the at least one target feature has a first feature end and a second feature end and a target axis therebetween,
   wherein the pose of the tool datum with respect to the at least one target datum is related to the pose of the tool axis with respect to the target axis of the at least one target feature.

2. The targeting system of claim 1, wherein the shape sensing element comprises at least one optical fiber, wherein the at least one optical fiber comprises at least one core, wherein the at least one core is operable to conduct the interrogation signal and the modified signal therethrough, wherein the interrogation signal comprises at least one wavelength of light.

3. The targeting system of claim 2, wherein at least one core is provided in a helical shape.

4. The targeting system of claim 2, wherein the at least one optical fiber includes a plurality of Fiber Bragg Gratings dispersed in the at least one core.

5. The targeting system of claim 1, wherein the shape sensing element is removably coupled in communication with the target feature.

6. The targeting system of claim 1, wherein the position of the second node with respect to the target feature is adjustable.

7. The targeting system of claim 1, wherein the surgical tool is removably coupled in communication with the first node of the shape sensing element.

8. The targeting system of claim 1, wherein the display is coupled in communication with the surgical tool.

9. The targeting system of claim 1, the display further comprising a touch-sensitive screen operable for the user to communicate with the data processor.

10. The targeting system of claim 1, wherein the shape sensing element is removably coupled to the interrogator.

11. The targeting system of claim 1, further comprising a calibration file containing information related to the position of the target datum in the target reference frame, wherein the calibration file is provided as digital information stored on a portable memory device, or as digital information accessible by the data processing system via a network data connection, or a combination thereof.

12. The targeting system of claim 1, wherein the origin of the coordinate system defines the first node.

13. The targeting system of claim 1, wherein the display is incorporated into a device wearable by the user.

14. The targeting system of claim 1, wherein the surgical device is an intramedullary nail, a fixation plate, an intramedullary extension of a joint reconstruction implant, a second surgical tool, or a combination thereof.

15. The targeting system of claim 1, wherein the interrogation information is provided to the data processing system via a wireless data transmission system.

16. The targeting system of claim 1, wherein the information related to the comparison is provided to the display via a wireless data transmission system.

17. A medical apparatus, comprising:
a surgical device having at least one target feature, wherein the at least one target feature has a first feature end and a second feature end and a target axis therebetween; and
a shape sensing element having a first element end and a second element end and a plurality of nodes dispersed therein, the first element end connectable to an interrogator, wherein the shape sensing element is operable to receive an interrogation signal from the interrogator and return a modified signal to the interrogator related to the position and orientation of each node in a coordinate system;
wherein a first node is coupled in communication with a surgical tool and least a second node is coupled in communication with the at least one target feature, wherein the surgical tool comprises a first tool end and a second tool end and a tool axis therebetween,
wherein the position and orientation of the first node in the coordinate system defines a tool reference frame and the position and orientation of the at least second node in the coordinate system defines a target reference frame,
wherein a tool datum is definable in the tool reference frame and at least one target datum is definable in the target reference frame,
wherein the pose of the tool datum with respect to the at least one target datum is related to the pose of the tool axis with respect to the target axis of the at least one target feature.

18. The medical apparatus of claim 17, wherein the shape sensing element comprises at least one optical fiber, wherein the at least one optical fiber comprises at least one core, wherein the at least one core is operable to transmit an interrogation signal therethrough, wherein the interrogation signal comprises at least one wavelength of light.

19. The medical apparatus of claim 18, wherein at least one core is provided in a helical shape.

20. The medical apparatus of claim 18, wherein the at least one optical fiber includes a plurality of Fiber Bragg Gratings dispersed in the at least one core.

21. The medical apparatus of claim 17, wherein the surgical tool is removably coupled in communication with the first node of the shape sensing element.

22. The medical apparatus of claim 17, further comprising a calibration file containing information related to the position of the target datum in the target reference frame, wherein the calibration file is provided as digital information stored on a portable memory device, or as digital information accessible by the data processing system via a network data connection, or a combination thereof.

23. The medical apparatus of claim 17, wherein the surgical device is an intramedullary nail, a fixation plate, an intramedullary extension of a joint reconstruction implant, a second surgical tool, or a combination thereof.

24. The medical apparatus of claim 17, wherein at least a portion of the shape sensing element is recessed below the outer surface of the surgical device.

25. The medical apparatus of claim 17, wherein the surgical device is constructed from a composite material, wherein the composite material includes a high modulus fiber.

26. The medical apparatus of claim 17, wherein the surgical tool is removably coupled in rigid communication with the first node of the shape sensing element.

27. The medical apparatus of claim 17, wherein the origin of the coordinate system defines the first node.

28. A method of aligning a tool to a target feature on a surgical device, comprising:
coupling a first node of a shape sensing element in communication with a surgical tool, the surgical tool having a first tool end and a second tool end and a tool axis therebetween, the shape sensing element having a first element end and a second element end and a plurality of nodes therebetween, the first element end coupled to an interrogator, the interrogator operable to provide an interrogation signal to the shape sensing element and receive a modified signal from the shape sensing element to provide information related to the position and orientation of each node in a coordinate system and transmit the interrogation information to a data processing system, the data processing system operable to interpret the interrogation information and compare the pose of the first node with respect to at least a second node in a coordinate system, wherein the position and orientation of the first node in the coordinate system defines a tool reference frame, wherein a tool datum is definable in the tool reference frame;
coupling a second node of the shape sensing element in communication with at least one target feature on a surgical device, the at least one target feature having a first feature end and a second feature end and a target axis therebetween, wherein the position and orientation of the second node in the coordinate system defines a target reference frame, wherein a target datum is definable in the target reference frame; and providing information to the user comparing the pose of the tool axis with respect to the target axis;

wherein the pose of the tool axis with respect to the target axis is related to the pose of the tool datum with respect to the target datum.

29. The method of claim 28, wherein the shape sensing element comprises at least one optical fiber, the at least one optical fiber comprising at least one core, wherein the at least one core is operable to transmit the interrogation signal therethrough, wherein the interrogation signal comprises at least one wavelength of light.

30. The method of claim 29, wherein at least one core is provided in a helical shape.

31. The method of claim 29, wherein the at least one optical fiber includes a plurality of Fiber Bragg Gratings dispersed in the at least one core.

32. The method of claim 28, further comprises providing a calibration file to the data processing system, wherein the calibration file comprises information relating to the pose of the target datum in the target reference frame, wherein the calibration file is provided as digital information stored on a portable memory device, or as digital information accessible by the data processing system via a network data connection, or a combination thereof.

* * * * *